United States Patent
Androphy et al.

(10) Patent No.: US 11,628,158 B2
(45) Date of Patent: Apr. 18, 2023

(54) SMALL MOLECULE ANTIVIRAL DRUG TREATMENT FOR HUMAN PAPILLOMAVIRUS INFECTIONS

(71) Applicants: THE TRUSTEES OF INDIANA UNIVERSITY, Bloomington, IN (US); KOVINA THERAPEUTICS, INC., Indianapolis, IN (US)

(72) Inventors: Elliot J. Androphy, Indianapolis, IN (US); Samy Meroueh, Carmel, IN (US); Zhijian Lu, Indianapolis, IN (US)

(73) Assignees: THE TRUSTEES OF INDIANA UNIVERSITY, Bloomington, IN (US); KOVINA THERAPEUTICS, INC., Indianapolis, IN (US)

( * ) Notice: Subject to any disclaimer, the term of this patent is extended or adjusted under 35 U.S.C. 154(b) by 0 days.

(21) Appl. No.: 17/579,069

(22) Filed: Jan. 19, 2022

(65) Prior Publication Data
US 2022/0142973 A1    May 12, 2022

Related U.S. Application Data

(63) Continuation of application No. PCT/US2021/027746, filed on Apr. 16, 2021.

(60) Provisional application No. 63/011,811, filed on Apr. 17, 2020.

(51) Int. Cl.
| | |
|---|---|
| A61K 31/381 | (2006.01) |
| A61P 31/20 | (2006.01) |
| A61K 9/00 | (2006.01) |
| C07D 215/06 | (2006.01) |
| C07D 487/04 | (2006.01) |
| C07D 495/04 | (2006.01) |
| A61K 38/10 | (2006.01) |

(52) U.S. Cl.
CPC .......... *A61K 31/381* (2013.01); *A61K 9/0002* (2013.01); *A61K 38/10* (2013.01); *A61P 31/20* (2018.01); *C07D 215/06* (2013.01); *C07D 487/04* (2013.01); *C07D 495/04* (2013.01)

(58) Field of Classification Search
None
See application file for complete search history.

(56) References Cited

U.S. PATENT DOCUMENTS

| | | | |
|---|---|---|---|
| 7,019,000 B1 | 3/2006 | Bernard | |
| 2009/0274621 A1* | 11/2009 | Wegrzyn | A61K 47/54 514/765 |
| 2010/0105722 A1 | 4/2010 | Kuehnert | |
| 2016/0214994 A1 | 7/2016 | Yingli | |
| 2020/0197369 A1* | 6/2020 | Tang | A61K 31/4162 |

OTHER PUBLICATIONS

STN registry compound RN#1048824-05-0 (Entry date Sep. 12, 2008).*
Krist et al. "Catalytically Important Residues of E6AP Ubiquitin Ligase Identified Using Acid-Cleavable Photo-Cross-Linkers". Biochemistry. 2015. 54(29): pp. 4411-4414.
Scheffner et al. "Identification of a human ubiquitin-conjugating enzyme that mediates the E5-AP-dependent ubiquitination of p53", Proc. Natl. Acad. Sci. USA. 1994. vol. 91, pp. 8797-8801.
PubChem-SID-132887069, Modify Date: May 31, 2019 (May 31, 2019).
International Search Report for PCT/US21/27746.

* cited by examiner

*Primary Examiner* — Bong-Sook Baek
(74) *Attorney, Agent, or Firm* — Barnes & Thornburg LLP

(57) ABSTRACT

Compositions and methods are provided for treating HPV infections including pre-malignant and cancers. Compounds that specifically bind to the HPV E6 protein and inactivate the protein are disclosed.

10 Claims, 6 Drawing Sheets

Specification includes a Sequence Listing.

1                                                              51
MFQDPQERPRKLPQLCTELQTTIHDIILECVYCKQQLLRREVYDFAFRDLCIVYRDGNPYAVCD

KCLKFYSKISEYRHYCYSLYGTTLEQQYNKPLCDLLIRCINCQKPLCPEEKQRHLDKKQRFHNI
                              151
RGRWTGRCMSCCRSSRTRRETQL

Fig.7

SEQUENCE LISTING

<160> NUMBER OF SEQ ID NOS: 2

<210> SEQ ID NO 1
<211> LENGTH: 151
<212> TYPE: PRT
<213> ORGANISM: Homo sapiens

<400> SEQUENCE: 1

```
Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150
```

```
<210> SEQ ID NO 2
<211> LENGTH: 19
<212> TYPE: PRT
<213> ORGANISM: Homo sapiens

<400> SEQUENCE: 2

Lys Glu Lys Glu Glu Tyr Asn Ser Asn Cys Ser Cys Ile Ala Cys Ile
1               5                   10                  15

Gly Leu Ile
```

SMALL MOLECULE ANTIVIRAL DRUG TREATMENT FOR HUMAN PAPILLOMAVIRUS INFECTIONS

CROSS REFERENCE TO RELATED APPLICATIONS

This application is a continuation of International Application no. PCT/US2021/027746, filed on Apr. 16, 2021 which claims priority to U.S. Provisional Patent Application No. 63/011,811 filed on Apr. 17, 2020, the disclosures of which are expressly incorporated herein.

GOVERNMENT RIGHTS

This invention was made with government support under TR001108 awarded by the National Institutes of Health. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 2 kilobytes ASCII (text) file named "334140_ST25.txt", created on Jan. 12, 2022.

BACKGROUND OF THE DISCLOSURE

Human papillomavirus (HPV) is an exceedingly common infection. While most infections are benign, standard destructive remedies are painful and have potential complications and co-morbidities. Moreover, persistent infections with specific HPV types can evolve into invasive and metastatic cancers. These malignancies progress slowly over several years from benign to pre-malignant to invasive lesions, so there is a suitable interval for antiviral treatment.

HPV type 16 (HPV16) is the prototype of "high-risk" HPV for neoplastic transformation and accounts for about 50% of all cervical cancers across the world and is also present in the majority of anal, vulvar, and vaginal pre-cancers (dysplasias) and cancers. Globally, 600,000 cases of cervical cancer are diagnosed each year, from which an estimated 380,000 women die annually. In the United States about 12,000 cases for cervical cancer caused by HPV infection are newly diagnosed annually. It is predicted that 44 million cases of cervical cancer will arise worldwide over the next 50 years, which would be reduced by only 15% with robust vaccination programs (K. T. Simms et al Lancet Oncol. 2019; 20(3):394-407). A subset of vulvar, vaginal and penile cancers and the majority of anal squamous cell cancers are caused by HPV infection.

It has been recently found that many oropharyngeal cancers (OPC) are caused by HPV and this malignancy now exceeds the incidence of cervical cancers in the USA (MMWR Aug. 23, 2019, Vol 68 p 724). HPV16 can be detected in oral swabs but clinical identification of precursor lesions is not reliable and surgical field approaches carry major morbidity in the oropharynx. HPV associated OPC develop over one or more decades and are largely asymptomatic until patients have advanced tumors. Destructive surgical remedies, radiation, and chemotherapy are routinely used, carry high morbidity, and are a significant financial burden.

While the existing HPV capsid is highly effective as a prophylactic vaccine, it is expensive and has not had sufficient uptake to achieve herd immunity in the USA. More importantly, this vaccine is not therapeutic for women and men with existing HPV infection, including those who have progressed to pre-malignant or malignant disease. This vaccine does not change the clinical course after virus infection has been established.

Studies have suggested HPV E6 protein is essential for stable viral genome replication and epithelial cell transformation. E6 binds to the ubiquitin ligase E6AP (UBE3A), but will not bind to p53 in the absence of E6AP. E6AP is the founding member of the HECT domain ubiquitin ligases and transfers ubiquitin onto the tumor suppressor protein p53, resulting in its destruction by the proteasome. A subsequent conformational change in E6AP-bound E6 exposes a large p53 interaction surface to generate the E6•E6AP•p53 trimeric complex. The region of E6AP that complexes with HPV E6 contains an HPV E6 binding motif with the consensus sequence LxxLL, where L is leucine and x any amino acid that folds within an α-helix.

Travé and co-workers solved the trimeric crystal structure of HPV16 E6 in complex with peptides containing the LxxLL E6 binding motif and the core domain of p53. The LxxLL motif adopts an α-helical structure that docks into a well-defined large pocket. Replacement of any of the leucines within the helix disrupts binding to E6. This E6AP binding pocket on E6 acts as a 'hot spot' for association with cellular proteins encoding the LxxLL motif. The compounds disclosed herein covalently bind within this pocket, or 'hot spot' in HPV E6, such as HPV16 E6, and irreversibly block its interactions with E6AP and will interfere with other binding partners that encode the HPV E6 binding motif.

High-risk HPV E7 inhibits the Rb tumor suppressor pathway, causing continuous stimulation of cell division and induction of the p53 pathway. Both HPV16 E6 and E7 are expressed in HPV induced tumors. HPV E6 counteracts p53 activation by forming a complex with E6AP as well as binding to its other cellular partners through the same binding pocket. Studies have shown inhibiting E6 restores wild-type p53 protein levels and function (E. Cukuroglu, et al., Prog. Biophys. Mol. Biol. 116, 165-173 (2014)). Abrogation of HPV E6 activity leads to growth arrest or cell death of HPV cervical cancer cell lines.

There is great medical need for treatment of HPV infections. Our strategy was to use structure-based drug design to select drug-like molecules that specifically and covalently bind to E6 and disrupt its protein-protein interactions (PPI). Applicants anticipate that administration of medication that blocks HPV E6 functions including one topically applied to the cervix, anus, penis, vulva, vagina or oropharynx will effectively eliminate HPV DNA and serve to treat pre-malignant infected tissues and treat HPV induced cancers. In one embodiment a medication is provided that blocks HPV E6 functions and is topically applied to the cervix, anus, penis, vulva, vagina or oropharynx to treat pre-malignant infected tissues. In one embodiment a systemically delivered E6 binding compound is used to treat HPV induced cancers as well as pre-malignant HPV infections.

SUMMARY

In one aspect, the disclosure relates to a compound of the formula I

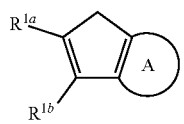

wherein ring A is

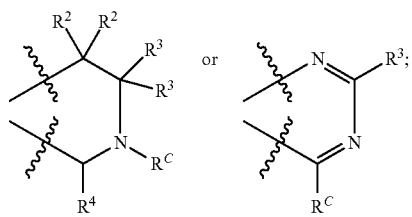

$R^{1a}$ and $R^{1b}$ are independently H, deuterium, or $C_1$-$C_6$ alkyl, or $R^{1a}$ and $R^{1b}$ together with the carbon atoms to which they are attached combine to form a $C_3$-$C_8$ cycloalkyl, wherein each hydrogen atom in $C_1$-$C_6$ alkyl and $C_3$-$C_8$ cycloalkyl is optionally substituted with $R^D$;

each $R^2$ is H;

each $R^3$ is independently H, deuterium, $C_1$-$C_6$ alkyl, $C_3$-$C_6$ cycloalkyl, $C_6$-$C_{10}$ aryl, —NH($R^A$), or —N($R^A$)($R^B$), wherein each hydrogen atom in $C_6$-$C_{10}$ aryl is optionally substituted by $R^D$, and wherein each hydrogen atom in $C_1$-$C_6$ alkyl and $C_3$-$C_6$ cycloalkyl is optionally substituted by $C_6$-$C_{10}$ aryl optionally substituted with at least one $R^D$;

$R^4$ is $C_6$-$C_{10}$ aryl, wherein each hydrogen atom is $C_6$-$C_{10}$ is optionally substituted with $R^D$;

$R^A$ and $R^B$ are independently $C_1$-$C_6$ alkyl, wherein each hydrogen atom in $C_1$-$C_6$ alkyl is optionally substituted by $C_6$-$C_{10}$ aryl, wherein each hydrogen atom is $C_6$-$C_{10}$ aryl is optionally substituted with $R^D$;

$R^C$ is $C_1$-$C_6$ alkyl, $C_3$-$C_8$ heterocycloalkyl, or —$C_1$-$C_6$ alkyl-$C_3$-$C_8$ heterocycloalkyl, wherein each hydrogen atom in $C_1$-$C_6$ alkyl and $C_3$-$C_8$ heterocycloalkyl is optionally substituted with $C_1$-$C_6$ alkyl, oxo, $C_3$-$C_8$ heterocycloalkyl, or $R^E$, provided $R^C$ includes at least one $R^E$;

each $R^D$ is independently deuterium, halogen, $C_1$-$C_6$ alkyl, or —$OC_1$-$C_6$ alkyl, wherein each hydrogen atom in $C_1$-$C_6$ alkyl is optionally substituted with deuterium, halogen, or oxo;

$R^E$ is $C_1$-$C_6$ alkyl, $C_2$-$C_6$ alkenyl, or $C_3$-$C_6$ alkynyl, wherein each hydrogen atom in $C_1$-$C_6$ alkyl, $C_2$-$C_6$ alkenyl, and $C_3$-$C_6$ alkynyl is optionally substituted with halogen, oxo, or —N($C_1$-$C_6$ alkyl)$_2$, provided at least one hydrogen atom in $C_1$-$C_6$ alkyl, $C_2$-$C_6$ alkenyl, and $C_3$-$C_6$ alkynyl is substituted with halogen, oxo, or —N($C_1$-$C_6$ alkyl)$_2$ or a pharmaceutically acceptable salt thereof, and the use of such a compound in treating HPV infections in a patient, including non-malignant infections and HPV related cancer.

In one embodiment the present disclosure is directed to an HPV E6 binding compound of Formula II:

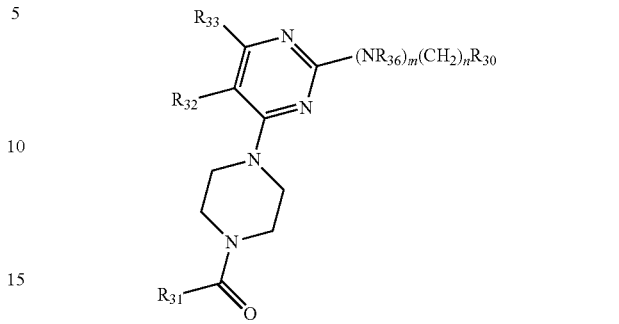

wherein $R_{30}$ is selected from the group consisting of H, halo, cyclopropyl, and

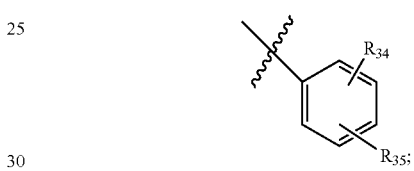

wherein $R_{34}$ is selected from the group consisting of H, —$OCH_3$, —$OCF_3$, F, —O-cyclopropyl and cyclopropyl;

$R_{35}$ is selected from the group consisting of H and —$OCH_3$;

n is an integer selected from 0-4;

m is 0 or 1;

$R_{31}$ is selected from the group consisting of —CH=$CH_2$, —$CR_{60}$=$CH_2$—CH=$CHCH_2N(CH_3)_2$, —$CR_{60}$=$CH_2$—$N(CH_3)_2$, —CH≡$CHCH_3$, $CH_2$(halo) and $CH_3$, wherein $R_{60}$ is H or F;

$R_{32}$ and $R_{33}$ together with the atoms to which they are bound form a cyclic or bicyclic ring selected from the group consisting of

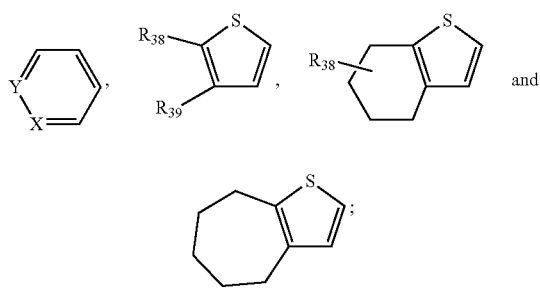

$R_{36}$ is selected from the group consisting of H and $CH_3$;

$R_{38}$ and $R_{39}$ are independently H, halo or $CH_3$; and

X and Y are independently N or C, and the use of such a compound in treating HPV infections in a patient, including non-malignant infections and HPV related cancer.

In one embodiment the present disclosure is directed to an HPV E6 binding compound of Formula III:

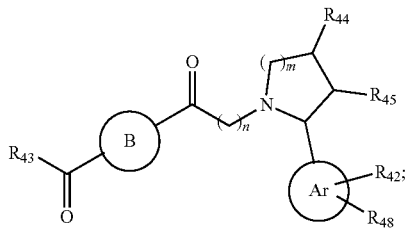

wherein n=1-5; m=1-4;

ring Ar is benzene ring or a heterocycle;

$R_{42}$ and $R_{48}$ are independently selected from the group consisting of H, —$OCH_3$, —$OCF_3$, halo and $C_1$-$C_4$ alkyl or $R_{42}$ and $R_{48}$ together with the atoms of ring Ar to which they are bound form a 9 or 10 membered bicyclic aryl or heteroaryl;

$R_{43}$ is selected from the group consisting of —CH=$CH_2$, —$CR_{51}$=$CH_2$, and $CH_2$(halo), wherein $R_{51}$ is H or halo, optionally where $R_{51}$ is H or F;

ring B is selected from the group consisting of

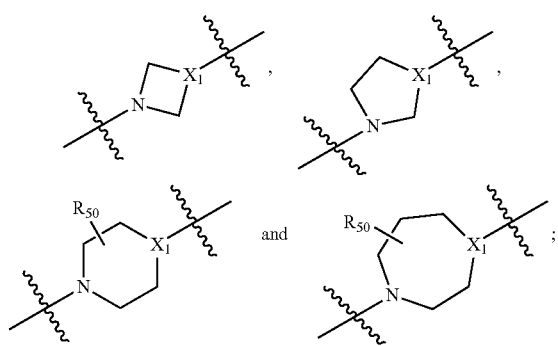

wherein $X_1$ is N or C; and $R_{50}$ is H or $CH_3$, optionally wherein ring B is selected from the group consisting of

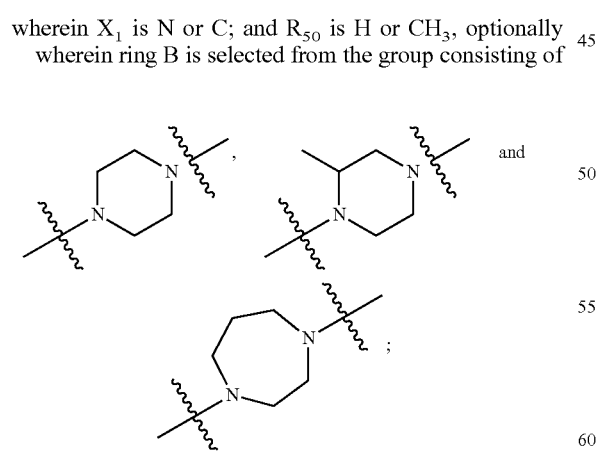

$R_{44}$ and $R_{45}$ are independently H, —$OCH_3$, —$OCF_3$, halo, $C_1$-$C_4$ alkyl, $N(R_{47})(R_{49})$, $SR_{47}$, or $P(R_{47})(R_{49})$, wherein $R_{47}$ and $R_{49}$ are independently H or $C_1$-$C_4$ alkyl, or $R_{44}$ and $R_{45}$ together with the atoms to which they are bound form a cyclic ring selected from the group consisting of

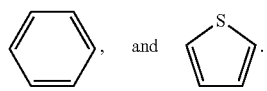 [SMILES: c1ccccc1 ; c1ccsc1]

The present disclosure further includes the use of such a compound in treating HPV infections in a patient, including non-malignant infections and HPV related cancer.

In one embodiment, the present disclosure is directed to an HPV E6 binding compound having the general structure of:

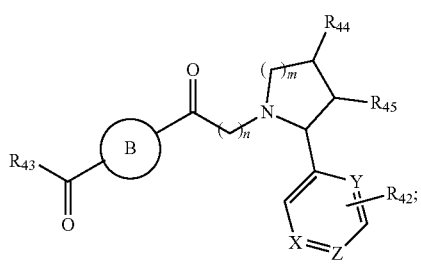

wherein n=1 or 2; m=1 or 2; $X_1$, $Y_1$ and $Z_1$ are independently C or N;

$R_{42}$ is selected from the group consisting of H, —$OCH_3$, —$OCF_3$, halo and $C_1$-$C_4$ alkyl;

$R_{43}$ is selected from the group consisting of —CH=$CH_2$, —$CR_{51}$=$CH_2$, and $CH_2$(halo), wherein $R_{51}$ is H or halo, optionally where $R_{51}$ is H or F;

ring B is selected from the group consisting of

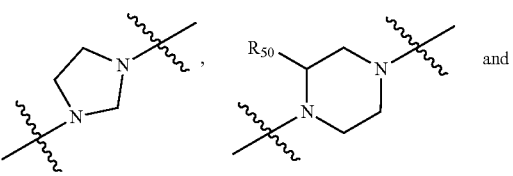

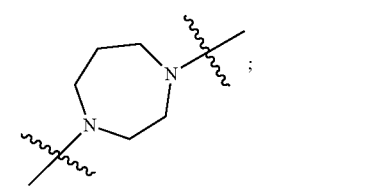

wherein $R_{50}$ is H or $CH_3$; and $R_{44}$ and $R_{45}$ are independently H, —$OCH_3$, —$OCF_3$, halo, $C_1$-$C_4$ alkyl, $N(R_{47})(R_{49})$, $SR_{47}$, or $P(R_{47})(R_{49})$, wherein $R_{47}$ and $R_{49}$ are independently H or $C_1$-$C_4$ alkyl, or $R_{44}$ and $R_{45}$ together with the atoms to which they are bound form a 5 or 6 membered aryl or heteroaryl ring, optionally wherein $R_{44}$ and $R_{45}$ together with the atoms to which they are bound form a cyclic ring selected from the group consisting of

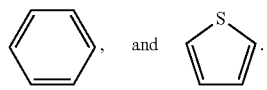

The present disclosure further includes the use of such a compound in treating HPV infections in a patient, including non-malignant infections and HPV related cancer.

In one embodiment, the present disclosure is directed to an HPV E6 binding compound having the general structure of

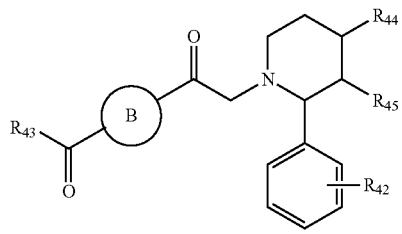

wherein $R_{42}$ is selected from the group consisting of H, —OCH$_3$, —OCF$_3$, halo and CH$_3$;

$R_{43}$ is selected from the group consisting of —CH=CH$_2$, —CF=CH$_2$, and CH$_2$(halo);

ring B is selected from the group consisting of

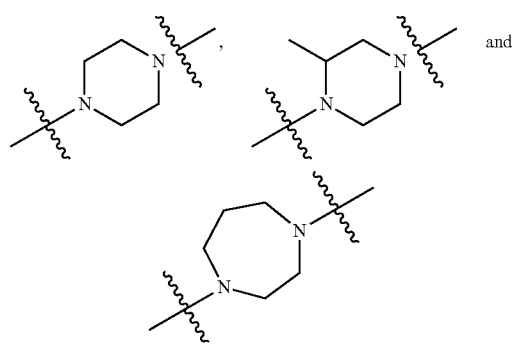

and $R_{44}$ and $R_{45}$ together with the atoms to which they are bound form a cyclic ring selected from the group consisting of

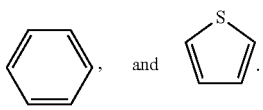 [SMILES: c1ccccc1 ; c1ccsc1]

The present disclosure further includes the use of such a compound in treating HPV infections in a patient, including non-malignant infections and HPV related cancer.

In one embodiment, the present disclosure is directed to an HPV E6 binding compound having the structure of

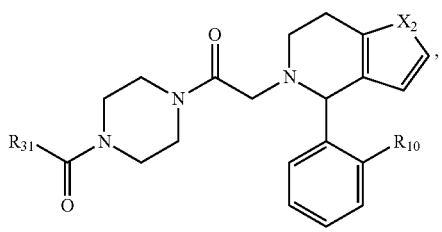

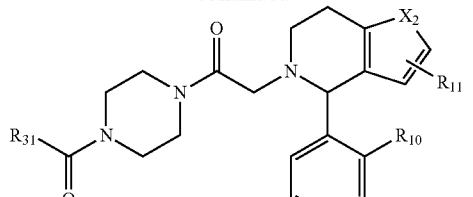

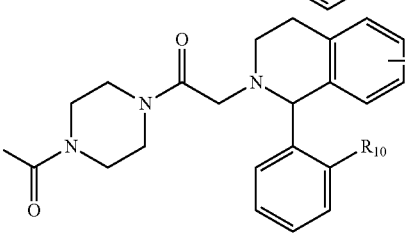

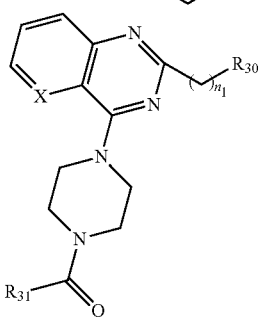

wherein

X$_2$ is N, S or C $R_{10}$ is H, CH$_3$, CF$_3$, OCH$_3$, OCF$_3$, CN or halo;

$R_{11}$ is H or OCH$_3$;

$R_{30}$ is selected from the group consisting of H, halo, cyclopropyl, and

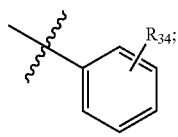

$n_1$ is an integer selected from 1 to 4;

X is N or C;

$R_{31}$ is selected from the group consisting of —CH=CH$_2$, —CR$_{51}$=CH$_2$, —CH=CHCH$_2$N(CH$_3$)$_2$, —CH=CHCH$_3$, CH$_2$(halo) and CH$_3$ wherein $R_{51}$ is H or halo, optionally where $R_{51}$ is H or F, optionally wherein $R_{31}$ is —CH=CHCH$_2$N(CH$_3$)$_2$, —CH=CH$_2$, or —CH=CHCH$_3$, optionally wherein $R_{31}$ is —CH=CH$_2$; and $R_{34}$ is selected from the group consisting of H, —OCH$_3$, —OCF$_3$, and cyclopropyl, and the use of such a compound in treating HPV infections in a patient, including non-malignant infections and HPV related cancer.

In accordance with one embodiment any of the HPV E6 binding compounds disclosed herein can be used to treat an HPV infection, including the treatment of non-malignant, pre-malignant and HPV induced tumors. In one embodiment the HPV E6 binding compounds disclosed herein are used to inhibit E6 binding to ubiquitin ligase E6AP. In one embodiment the HPV E6 binding compounds disclosed herein are used to inhibit E6 activity and restore wild-type p53 protein levels and function.

Additional embodiments, features, and advantages of the disclosure will be apparent from the following detailed description and through practice of the disclosure. The compounds of the present disclosure can be described as embodiments in any of the following enumerated clauses. It will be understood that any of the embodiments described herein can be used in connection with any other embodiments described herein to the extent that the embodiments do not contradict one another.

BRIEF DESCRIPTION OF THE DRAWINGS

FIG. 7 provides the amino acid sequence of the HPV-16 E6 protein (SEQ ID NO: 1) and indicates the position of cysteine 51 in the HPV-16 E6 protein sequence as referenced herein.

DETAILED DESCRIPTION

Figure 1A:
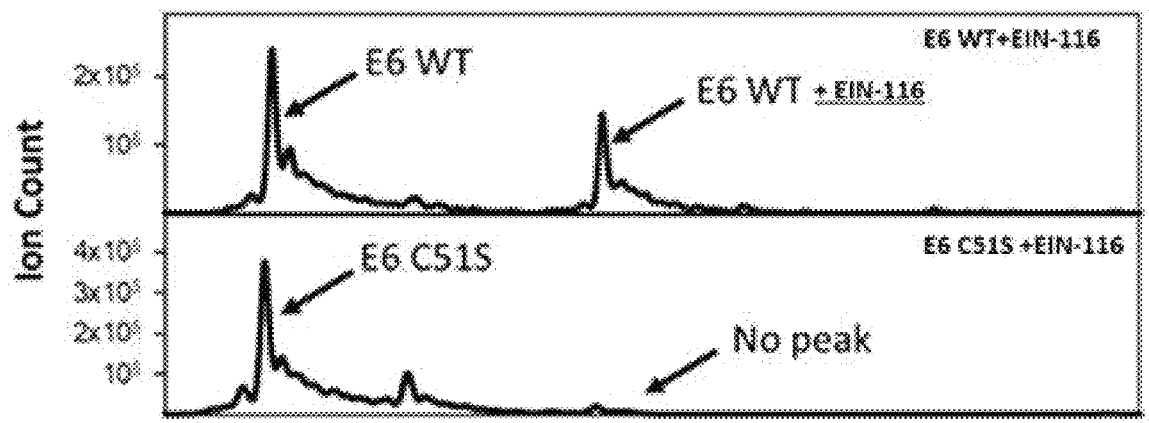
FIG. 1A is a depiction of electrospray ionization (ESI) mass spectrometry of E6 wild-type (WT), incubated with DMSO or 100 μM EIN-116 for 16 hr at 4° C. (top). ESI mass spectrometry of E6 C51S in which the HPV mutant, incubated with DMSO or 100 μM EIN-116 for 16 hr at 4° C. (bottom).

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Chemical nomenclature for compounds described herein has generally been derived using the commercially available ACD/Name 2014 (ACD/Labs) or ChemBioDraw Ultra 19.0 (Perkin Elmer).

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

DEFINITIONS

In describing and claiming the invention, the following terminology will be used in accordance with the definitions set forth below.

As used herein, the terms "including," "containing," and "comprising" are used in their open, non-limiting sense.

The term "about" as used herein means greater or lesser than the value or range of values stated by 10 percent but is not intended to limit any value or range of values to only this broader definition. Each value or range of values preceded by the term "about" is also intended to encompass the embodiment of the stated absolute value or range of values.

As used herein, the term "purified" and like terms relate to the isolation of a molecule or compound in a form that is substantially free of contaminants normally associated with the molecule or compound in a native or natural environment. As used herein, the term "purified" does not require absolute purity; rather, it is intended as a relative definition.

As used herein, the term "treating" includes alleviation of symptoms associated with a specific disorder or condition and/or preventing or eliminating said symptoms.

As used herein an "effective" amount or a "therapeutically effective amount" of a drug refers to a nontoxic but enough of the drug to provide the desired effect. The amount that is "effective" will vary from subject to subject or even within a subject overtime, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

As used herein the term "patient" without further designation is intended to encompass any warm blooded vertebrate domesticated animal (including for example, but not limited to livestock, horses, cats, dogs and other pets) and humans and includes individuals not under the direct care of a physician.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$. Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroalicyclic, alkoxy, halo, carbonyl, oxo, (=O), C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with an "aryl" group may be referred to as an "alkylaryl" group.

As used herein, the term "alkenyl" includes a chain of carbon atoms, which is optionally branched, and contains from 2 to 20 carbon atoms, and also includes at least one carbon-carbon double bond (i.e., C=C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Alkenyl may be unsubstituted or substituted as described for alkyl or as described in the various embodiments provided herein. The at least one carbon-carbon double bond may be internal or terminal. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e., C≡C). It will be understood that in certain embodiments, alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Alkynyl may be unsubstituted, or substituted as described for alkyl or as described in the various embodiments provided herein. The at least one carbon-carbon triple bond may be internal or terminal. Illustrative alkynyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthylenyl and anthracenyl. The aryl group may be unsubstituted or substituted as described for alkyl or as described in the various embodiments provided herein.

As used herein, the term "cycloalkyl" refers to a 3 to 15 member all-carbon monocyclic ring, including an all-carbon 5-member/6-member or 6-member/6-member fused bicyclic ring, or a multicyclic fused ring (a "fused" ring system means that each ring in the system shares an adjacent pair of carbon atoms with each other ring in the system) group, or a carbocyclic ring that is fused to another group such as a heterocyclic, such as ring 5- or 6-membered cycloalkyl fused to a 5- to 7-membered heterocyclic ring, where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_9$, $C_3$-$C_6$ and $C_4$-$C_6$. Cycloalkyl may be unsubstituted or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, and the like. Illustrative examples of cycloalkyl groups shown in graphical representations include the following entities, in the form of properly bonded moieties:

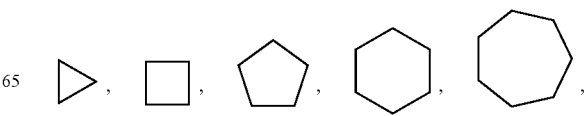

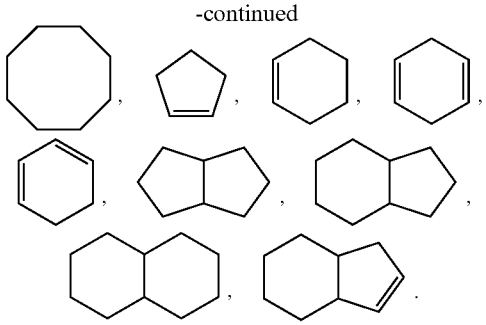

As used herein, the term "heterocycloalkyl" or "heterocyclic" defines a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. A heterocycloalkyl group may be fused to another group such as another heterocycloalkyl, or a heteroaryl group. Heterocycloalkyl may also have one of more double bonds, including double bonds to nitrogen (e.g., C=N or N=N) but does not contain a completely conjugated pi-electron system. It will be understood that in certain embodiments, heterocycloalkyl may be advantageously of limited size such as 3- to 8-membered heterocycloalkyl, 5- to 7-membered heterocycloalkyl, 3-, 4-, 5-, 6-, or 7-membered heterocycloalkyl, and the like. Heterocycloalkyl may be unsubstituted or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1, 2, 3, 4-tetrahydropyridinyl, and the like. Illustrative examples of heterocycloalkyl groups shown in graphical representations include the following entities, in the form of properly bonded moieties:

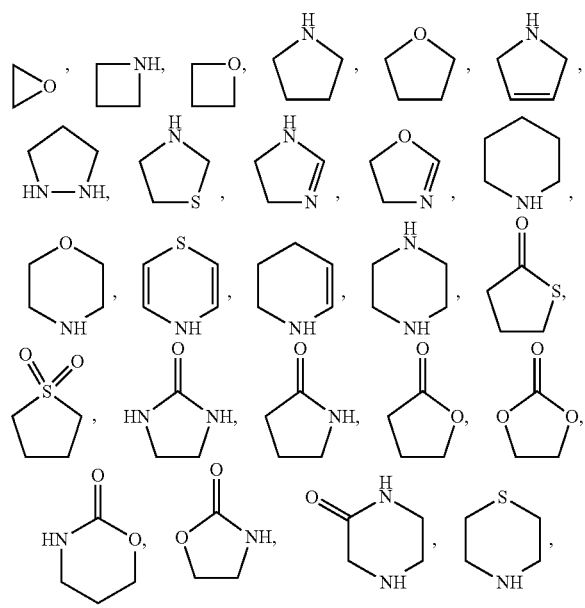

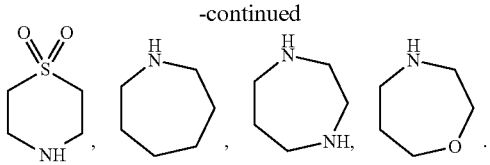

As used herein, "halo" or "halogen" refers to fluorine, chlorine, bromine, or iodine.

The term "oxo" represents a carbonyl oxygen. For example, a cyclopentyl substituted with oxo is cyclopentanone.

As used herein, "bond" absent further characterization refers to a covalent bond.

The term "substituted" means that the specified group or moiety bears one or more substituents. The term "unsubstituted" means that the specified group bears no substituents. Where the term "substituted" is used to describe a structural system, the substitution is meant to occur at any valency-allowed position on the system. In some embodiments, "substituted" means that the specified group or moiety bears one, two, or three substituents. In other embodiments, "substituted" means that the specified group or moiety bears one or two substituents. In still other embodiments, "substituted" means the specified group or moiety bears one substituent.

As used herein, "optional" or "optionally" means that the subsequently described event or circumstance may but need not occur, and that the description includes instances where the event or circumstance occurs and instances in which it does not. For example, "wherein each hydrogen atom in $C_6$-$C_{10}$ aryl is optionally substituted by $R^D$," means that an $R^D$ may be but need not be present on any of the $C_6$-$C_{10}$ aryl by replacement of a hydrogen atom for each $R^D$ group, and the description includes situations where the $C_6$-$C_{10}$ aryl is not substituted with the $R^D$ group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, the phrase "taken together with the atoms to which they are attached" or "taken together with the carbon atom to which they are attached" or "combine to form" means that two substituents (e.g., $R^{1a}$ and $R^{1b}$) each attached to additional atoms to form the structure defined by the claim, such as $C_3$-$C_8$ cycloalkyl. For example, in the context of the compound of Formula I, the phrase "Ria and $R^{1b}$ together with the atoms to which they attached form a $C_3$-$C_8$ cycloalkyl" includes, but is not limited to the compounds represented as follows:

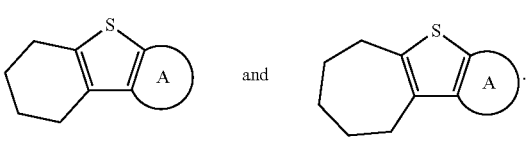

As used herein, the term "pharmaceutically acceptable salt" refers to those salts which counter ions which may be used in pharmaceuticals. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

Pharmaceutically acceptable salts are well known to those skilled in the art, and any such pharmaceutically acceptable salt may be contemplated in connection with the embodiments described herein. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound of Formula I, Ia, Ib, II, III and IIIa that contain a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The disclosure also relates to pharmaceutically acceptable prodrugs of the compounds of Formula I, Ia, Ib, II, III and IIIa, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula I, Ia, Ib, II, II and IIIa). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs," ed. H. Bundgaard, Elsevier, 1985.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (preferably with 14C), reaction kinetic studies (with, for example 2H or 3H), detection or imaging techniques [such as positron emission tomography (PET) or single-photon emission computed tomography (SPECT)] including drug or substrate tissue distribution assays, or in radioactive treatment of patients. Further, substitution with heavier isotopes such as deuterium (i.e., 2H) may afford certain therapeutic advantages resulting from greater metabolic stability, for example increased in vivo half-life or reduced dosage requirements. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

EMBODIMENTS

The present disclosure is directed to compositions and methods for treating Human Papillomavirus (HPV) infections. In one embodiment compositions comprising the HPV E6 binding compounds disclosed herein are formulated for topical application to the cervix, anus, or oropharynx. The compounds disclosed herein have be found to bind to amino acid residues of the E6AP binding pocket of HPV E6 protein and interfere with the activities of HPV E6, including its ability to interact with E6AP. Abrogation of HPV E6 activity has been found to lead to growth arrest of HPV-infected cells and/or cell death of HPV cervical cancer cell lines.

In accordance with one embodiment compounds that directly and irreversibly bind to the HPV-16 E6 protein are provided. In one embodiment these compounds are used in methods relating to treatment, such as inhibition or prevention or amelioration, of HPV, such as HPV E6, with one or more compounds comprising Formula I, Ia, Ib, II, III and IIIa and other E6 binding compounds, or mixtures thereof as disclosed herein. In one aspect, the small molecules described herein disrupt the E6 interaction with E6AP and thereby restore p53 functions in HPV-infected cells. In one aspect, the present disclosure is directed to a method for reducing HPV, (e.g., reducing HPV E6 levels, reducing the total number of infectious particles or reducing the number of infected cells) in a subject in need of HPV treatment. In one embodiment the method of reducing HPV includes administering one or more of an E6 binding compound, including compounds comprising the formula of Formula I, Ia, Ib, II, III and IIIa as disclosed herein, or any of the E6 binding compounds disclosed herein or mixtures thereof, to the subject. In another aspect, the present disclosure is directed to a method for ameliorating HPV, e.g., HPV E6, in a subject in need thereof. wherein the method includes administering a compound comprising the formula of one or more of compounds Formula I, Ia, Ib, II, III and IIIa, as disclosed herein, or any of the E6 binding compounds disclosed herein or mixtures thereof, to the subject.

In one aspect, the present disclosure is directed to a method for preventing an HPV infection in a subject in need thereof. The method includes administering a compound comprising the structure of Formula I, Ia, Ib, II, III and IIIa as disclosed herein, or any of the E6 binding compounds disclosed herein or mixtures thereof, to the subject.

Suitable subjects in need of treatment include subjects having (or suspected of having, based on exhibited symptoms or known exposure) an HPV infection. In one embodiment a subject known to be exposed to HPV, is administered a composition comprising an E6 binding compound of the present disclosure even prior to the subject demonstrating any symptoms of infection.

In accordance with one embodiment compounds that specifically bind to HPV E6 are provided wherein the compounds have the general structure of Formula I:

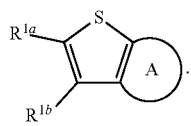

I wherein
ring A is

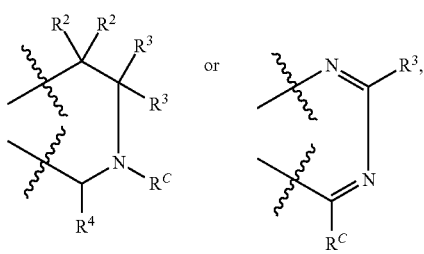

optionally wherein the compound has the structure of the formula Ia or Ib

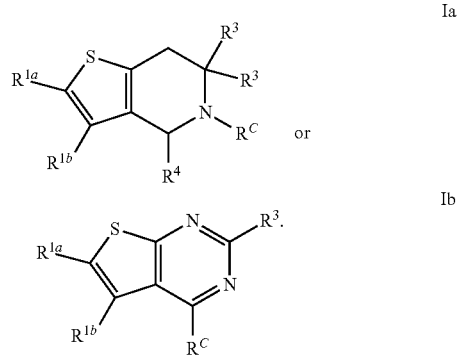

wherein, $R^{1a}$ and $R^{1b}$ are independently H, deuterium, $C_1$-$C_6$ alkyl or substituted $C_1$-$C_6$ alkyl. In some embodiments, each of $R^{1a}$ and $R^{1b}$ are independently optionally substituted. In some embodiments, each hydrogen atom in $C_1$-$C_6$ alkyl is optionally substituted with $R^D$. In some embodiments, $R^{1a}$ and $R^{1b}$ combine to form a $C_3$-$C_8$ cycloalkyl wherein each hydrogen atom in $C_1$-$C_6$ alkyl and $C_3$-$C_8$ cycloalkyl is optionally substituted with $R^D$. In some embodiments, $R^{1a}$ and $R^{1b}$ together with the carbon atoms to which they are attached combine to form a $C_3$-$C_8$ cycloalkyl. In some embodiments, each of $R^{1a}$ and $R^{1b}$ is H.

In some embodiments, $R^2$ is H.

In some embodiments, each $R^3$ is independently H, deuterium, $C_1$-$C_6$ alkyl, $C_3$-$C_6$ cycloalkyl, $C_6$-$C_{10}$ aryl, —NH($R^A$), or —N($R^A$)($R^B$). In some embodiments, each $R^3$ is optionally substituted. In some embodiments, each hydrogen atom in $C_6$-$C_{10}$ aryl is optionally substituted by $R^D$. In some embodiments, each hydrogen atom in $C_1$-$C_6$ alkyl and $C_3$-$C_6$ cycloalkyl is optionally substituted by $C_6$-$C_{10}$ aryl optionally substituted with at least one $R^D$. In some embodiments, each $R^3$ is H. In some embodiments, $R^3$ is $C_1$-$C_6$ alkyl, $C_3$-$C_6$ cycloalkyl, $C_6$-$C_{10}$ aryl, —NH($R^A$), or —N($R^A$)($R^B$), wherein each hydrogen atom in $C_6$-$C_{10}$ aryl is optionally substituted by $R^D$, and wherein each hydrogen atom in $C_1$-$C_6$ alkyl and $C_3$-$C_6$ cycloalkyl is optionally substituted by $C_6$-$C_{10}$ aryl optionally substituted with at least one $R^D$. In some embodiments, $R^3$ is $C_1$-$C_6$ alkyl wherein each hydrogen atom in $C_1$-$C_6$ alkyl is optionally substituted by $C_6$-$C_{10}$ aryl optionally substituted with at least one $R^D$. In some embodiments, $R^3$ is $C_1$-$C_6$ alkyl substituted by $C_6$-$C_{10}$ aryl optionally substituted with halogen or O—$C_1$-$C_6$ alkyl. In some embodiments, $R^3$ is $C_1$-$C_6$ alkyl. In some embodiments, $R^3$ is $C_3$-$C_6$ cycloalkyl.

In some embodiments, $R^4$ is optionally substituted $C_6$-$C_{10}$ aryl. In some embodiments, each hydrogen atom is $C_6$-$C_{10}$ is optionally substituted with $R^D$. In some embodiments, $R^4$ is $C_6$-$C_{10}$ aryl, wherein each hydrogen atom is $C_6$-$C_{10}$ is optionally substituted with halogen, $C_1$-$C_6$ alkyl, or —O$C_1$-$C_6$ alkyl.

In some embodiments, $R^A$ and $R^B$ are independently optionally substituted $C_1$-$C_6$ alkyl. In some embodiments, each hydrogen atom in $C_1$-$C_6$ alkyl is optionally substituted by $C_6$-$C_{10}$ aryl, wherein each hydrogen atom is $C_6$-$C_{10}$ is optionally substituted with $R^D$.

In some embodiments, $R^C$ is $C_1$-$C_6$ alkyl, $C_3$-$C_8$ heterocycloalkyl, or —$C_1$-$C_6$ alkyl-$C_3$-$C_8$ heterocycloalkyl wherein $R^C$ includes at least one $R^E$. In some embodiments, $R^C$ is optionally substituted. In some embodiments, each hydrogen atom in $C_1$-$C_6$ alkyl and $C_3$-$C_8$ heterocycloalkyl is optionally substituted with $C_1$-$C_6$ alkyl, oxo, $C_3$-$C_8$ heterocycloalkyl, or $R^E$. In some embodiments, $R^C$ is —$C_1$-$C_6$ alkyl-$C_3$-$C_8$ heterocycloalkyl, wherein each hydrogen atom in $C_1$-$C_6$ alkyl and $C_3$-$C_8$ heterocycloalkyl is optionally substituted with $C_1$-$C_6$ alkyl, oxo, $C_3$-$C_8$ heterocycloalkyl, or $R^E$. In some embodiments, $R^C$ is —$CH_2C(O)$—$C_3$-$C_8$ heterocycloalkyl-$R^E$ or —$CH(CH_3)C(O)$—$C_3$-$C_8$ heterocycloalkyl-$R^E$. In some embodiments, $R^C$ is $C_3$-$C_8$ heterocycloalkyl, wherein at least one hydrogen atom in $C_3$-$C_8$ heterocycloalkyl is substituted with $C_1$-$C_6$ alkyl, oxo, $C_3$-$C_8$ heterocycloalkyl, or $R^E$. In some embodiments, $R^C$ is $C_3$-$C_8$ heterocycloalkyl, wherein at least one hydrogen atom in $C_3$-$C_8$ heterocycloalkyl is substituted with $R^E$.

In some embodiments, each $R^D$ is independently deuterium, halogen, $C_1$-$C_6$ alkyl, or —$OC_1$-$C_6$ alkyl. In some embodiments, $R^D$ is substituted. In some embodiments, each hydrogen atom in $C_1$-$C_6$ alkyl is optionally substituted with deuterium, halogen, or oxo.

In some embodiments, $R^E$ is a covalent warhead for targeting cysteine residues in a protein. In some embodiments, $R^E$ is $C_1$-$C_6$ alkyl, $C_2$-$C_6$ alkenyl, $C_2$-$C_6$ alkynyl, or $C_3$-$C_6$ alkynyl, wherein at least one hydrogen atom in $C_1$-$C_6$ alkyl, $C_2$-$C_6$ alkenyl, $C_2$-$C_6$ alkynyl, and $C_3$-$C_6$ alkynyl is substituted with deuterium, halogen, oxo, or —$N(C_1$-$C_6$ alkyl$)_2$. In some embodiments, at least two hydrogen atoms in $C_1$-$C_6$ alkyl, $C_2$-$C_6$ alkenyl, $C_2$-$C_6$ alkynyl, and $C_3$-$C_6$ alkynyl is substituted with deuterium, halogen, oxo, or —$N(C_1$-$C_6$ alkyl$)_2$. In some embodiments, at least three hydrogen atoms in $C_1$-$C_6$ alkyl, $C_2$-$C_6$ alkenyl, $C_2$-$C_6$ alkynyl, and $C_3$-$C_6$ alkynyl is substituted with deuterium, halogen, oxo, or —$N(C_1$-$C_6$ alkyl$)_2$. In some embodiments, $R^E$ is —$C(O)C_1$-$C_6$ alkyl, —$C(O)C_2$-$C_6$ alkenyl, or —$C(O)C_2$-$C_6$ alkynyl, wherein each hydrogen atom in $C_1$-$C_6$ alkyl, $C_2$-$C_6$ alkenyl, and $C_2$-$C_6$ alkynyl, is optionally substituted with deuterium, halogen, or —$N(C_1$-$C_6$ alkyl$)_2$. In some embodiments, $R^E$ is

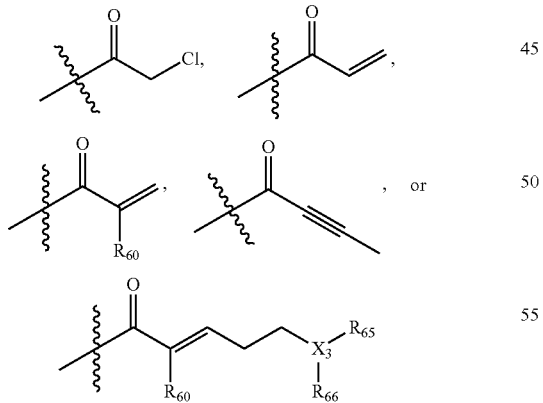

wherein $X_3$ is C or N;

$R_{60}$ is H or F; and $R_{65}$ and $R_{66}$ are methyl or together with the atoms to which they are attached form a 4, 5 or 6 membered cycloalkyl or heterocycloalkyl ring, optionally wherein $R^E$ is

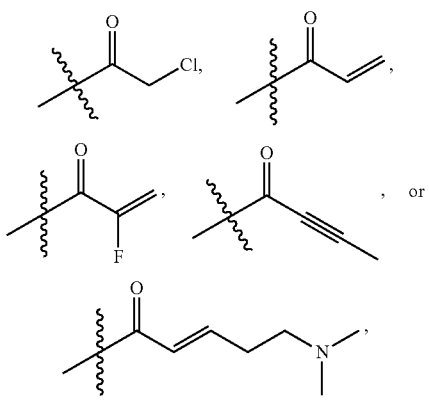

optionally wherein $R^E$ is

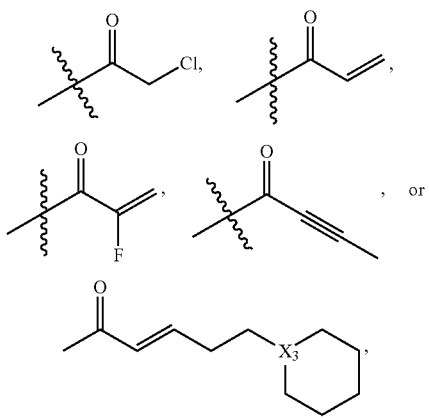

optionally wherein.

$R^E$ is

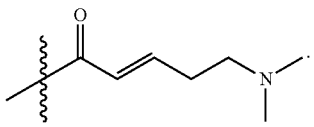

Table I provides illustrative embodiments of compounds of the Formula I, Ia, and Ib.

In one embodiment a compound that specifically binds to HPV E6 is provided wherein the compound has the general structure of

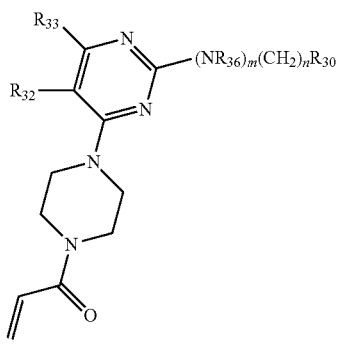

wherein
$R_{30}$ is selected from the group consisting of H, halo, cyclopropyl and

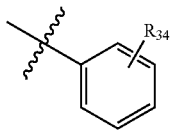

wherein $R_{34}$ is H, halo or —OCH$_3$;
$R_{32}$ and $R_{33}$ together with the atoms to which they are bound form a cyclic or bicyclic ring selected from the group consisting of

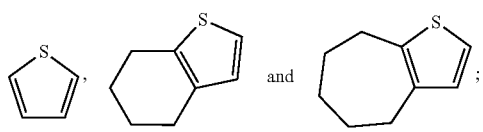

n is an integer selected from 0-4;
m is 0 or 1; and
$R_{36}$ is selected from the group consisting of H and CH$_3$; optionally wherein
m is 0;
n is an integer selected from 0-4; $R_{30}$ is H, and $R_{32}$ and $R_{33}$ together with the atoms to which they are bound form a cyclic or bicyclic ring selected from the group consisting of

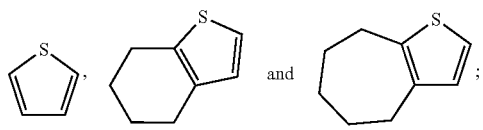

or optionally
wherein $R_{30}$ is

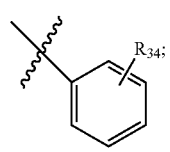

n is 1 or 2, m is 0 or 1 and $R_{34}$ is H, halo or —OCH$_3$ and $R_{32}$ and $R_{33}$ together with the atoms to which they are bound form a cyclic or bicyclic ring selected from the group consisting of

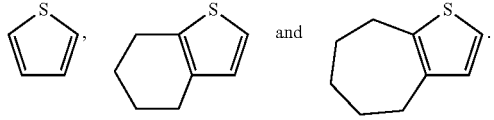

In one embodiment a compound that specifically binds to HPV E6 is provided wherein the compound has the general structure of

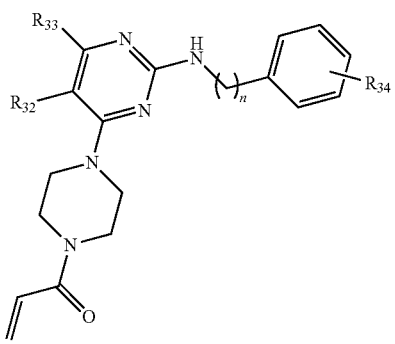

wherein
$R_{32}$ and $R_{33}$ together with the atoms to which they are bound form a cyclic or bicyclic ring selected from the group consisting of

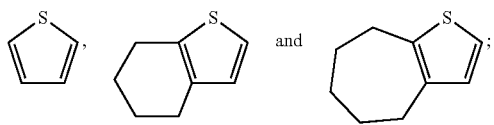

n is 1 or 2; and $R_{34}$ is H, halo or —OCH$_3$.

In one embodiment compounds that specifically bind to HPV E6 are provided wherein the compounds have the general structure of Formula II or IIIa

II

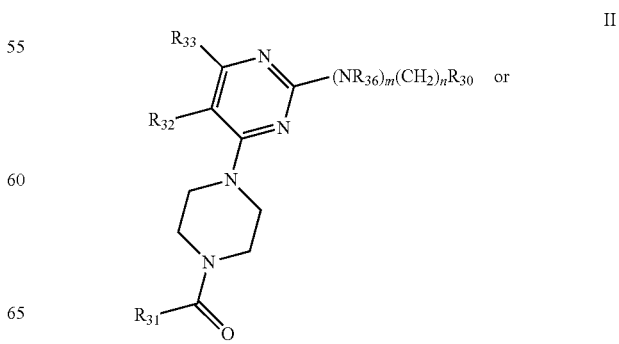

-continued

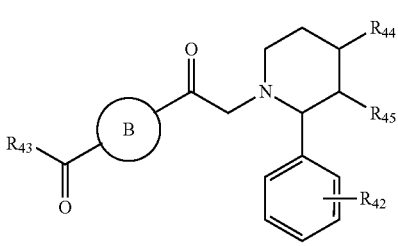

wherein
$R_{30}$ is selected from the group consisting of H, halo, cyclopropyl and

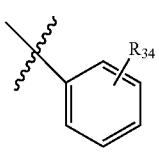

wherein $R_{34}$ is H, halo or —OCH$_3$;
$R_{32}$ and $R_{33}$ together with the atoms to which they are bound form a cyclic or bicyclic ring selected from the group consisting of

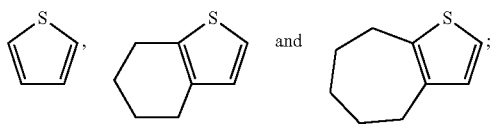

n is an integer selected from 0-4;
m is 0 or 1; and
$R_{36}$ is selected from the group consisting of H and CH$_3$;
optionally wherein
m is 0;
n is an integer selected from 0-4; $R_{30}$ is H, and $R_{32}$ and $R_{33}$ together with the atoms to which they are bound form a cyclic or bicyclic ring selected from the group consisting of

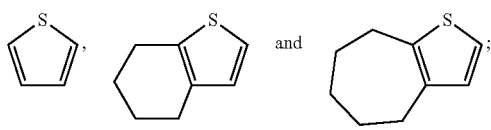

or optionally wherein $R_{30}$ is

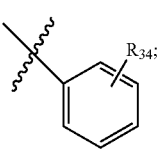

n is 1 or 2, m is 0 or 1 and $R_{34}$ is H, halo or —OCH$_3$ and $R_{32}$ and $R_{33}$ together with the atoms to which they are bound form a cyclic or bicyclic ring selected from the group consisting of

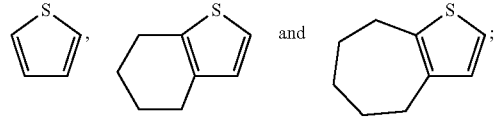

$R_{42}$ is selected from the group consisting of H, —OCH$_3$, —OCF$_3$, halo and CH$_3$;
$R_{43}$ is selected from the group consisting of —CH═CH$_2$, and CH$_2$(halo);
ring B is selected from the group consisting of

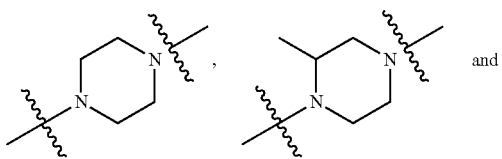

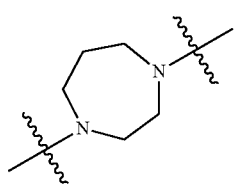

and
$R_{44}$ and $R_{45}$ together with the atoms to which they are bound form a cyclic ring selected from the group consisting of

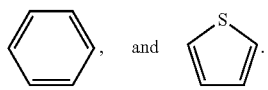

In one embodiment the compound has the structure of Formula II:

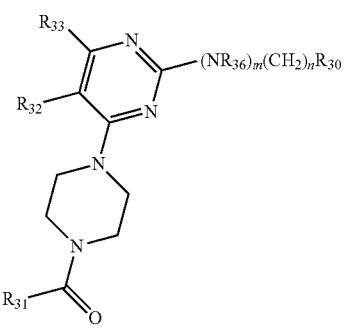

wherein

R$_{30}$ is selected from the group consisting of H, halo, cyclopropyl, and

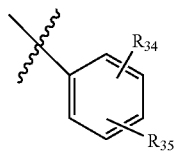

wherein R$_{34}$ is selected from the group consisting of H, —OCH$_3$, —OCF$_3$, and cyclopropyl;

R$_{35}$ is selected from the group consisting of H and —OCH$_3$;

n is an integer selected from 0-4;

m is 0 or 1;

R$_{31}$ is selected from the group consisting of —CH=CH$_2$, —CH=CHCH$_2$N(CH$_3$)$_2$, —CH=CHCH$_3$, CH$_2$(halo) and CH$_3$;

R$_{32}$ and R$_{33}$ together with the atoms to which they are bound form a cyclic or bicyclic ring selected from the group consisting of

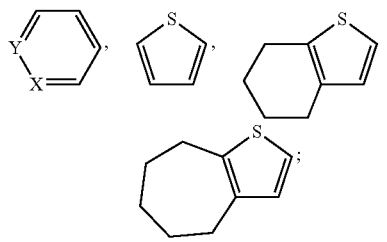

R$_{36}$ is selected from the group consisting of H and CH$_3$;

X and Y are independently N or C.

In one embodiment a compound that specifically binds to HPV E6 is provided wherein the compound has the structure of Formula II is provided wherein R$_{30}$ is

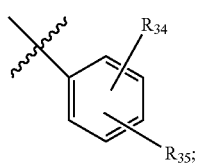

R$_{34}$ is selected from the group consisting of H, —OCH$_3$, and —OCF$_3$;

R$_{35}$ is H;

n is an integer selected from 0-4;

m is 0 or 1;

R$_{31}$ is selected from the group consisting of —CH=CH$_2$, CH$_2$(halo), —CH=CHCH$_2$N(CH$_3$)$_2$ and —CH=CHCH$_3$;

R$_{32}$ and R$_{33}$ together with the atoms to which they are bound form a cyclic or bicyclic ring selected from the group consisting of

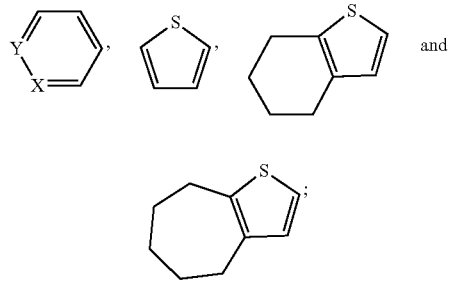

R$_{36}$ is selected from the group consisting of H and CH$_3$, and

X and Y are independently N or C.

In one embodiment a compound that specifically binds to HPV E6 is provided wherein the compound has the structure of Formula II is provided wherein R$_{30}$ is

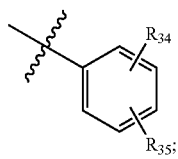

R$_{34}$ is selected from the group consisting of H, —OCH$_3$, and —OCF$_3$;

R$_{35}$ is H;

n is an integer selected from 0-4;

m is 0 or 1;

R$_{31}$ is selected from the group consisting of —CH=CH$_2$, CH$_2$(halo), —CH=CHCH$_2$N(CH$_3$)$_2$ and —CH=CHCH$_3$;

R$_{32}$ and R$_{33}$ together with the atoms to which they are bound form a cyclic or bicyclic ring selected from the group consisting of

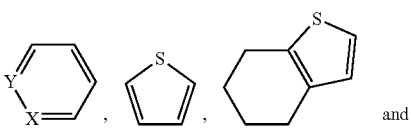

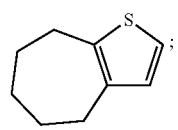

R$_{36}$ is selected from the group consisting of H and CH$_3$, and

X and Y are independently N or C.

In one embodiment a compound that specifically binds to HPV E6 is provided wherein the compound comprises the structure

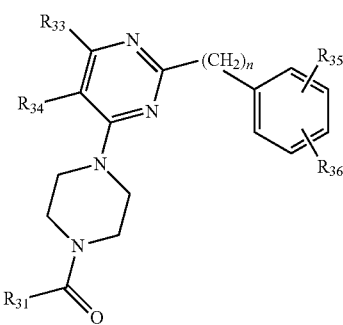

is provided wherein

R₃₃ and R₃₄ together with the atoms to which they are bound form a cyclic or bicyclic ring selected from the group consisting of

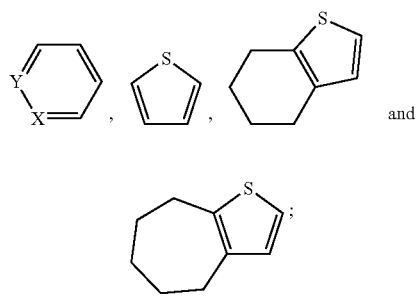

n is an integer selected from 0-4;

X and Y are independently N or C;

$R_{34}$ is selected from the group consisting of H, —OCH₃, and —OCF₃;

$R_{35}$ is H; and $R_{31}$ is selected from the group consisting of —CH=CH₂, CH₂(halo), —CH=CHCH₂N(CH₃)₂ and —CH≡CHCH₃.

In one embodiment a compound that specifically binds to HPV E6 is provided wherein the compound comprises the structure

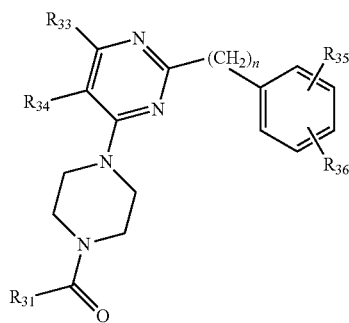

is provided wherein

R₃₃ and R₃₄ together with the atoms to which they are bound form a cyclic or bicyclic ring selected from the group consisting of

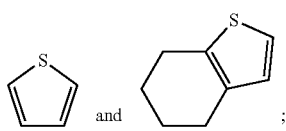 [SMILES: c1ccsc1 ; c1cc2c(s1)CCCC2]

n is an integer selected from 0-4;

$R_{34}$ is selected from the group consisting of H, —OCH₃, and —OCF₃;

$R_{35}$ is H; and $R_{31}$ is selected from the group consisting of —CH=CH₂, CH₂(halo), —CH=CHCH₂N(CH₃)₂ and —CH=CHCH₃.

In one embodiment a compound that specifically binds to HPV E6 is provided wherein the compound has the structure of

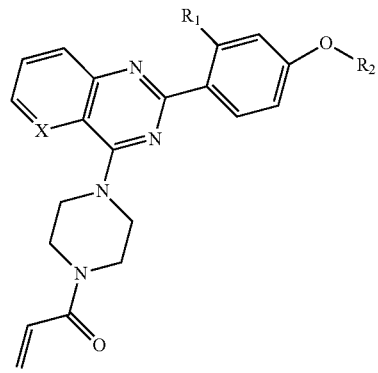

is provided wherein $R_1$ is H or F;

$R_2$ is —CH₃, —CF₃ or cyclopropyl; and

X is N or C.

In one embodiment the present disclosure is directed to a compound that specifically binds to HPV E6 wherein the compound comprises the structure of:

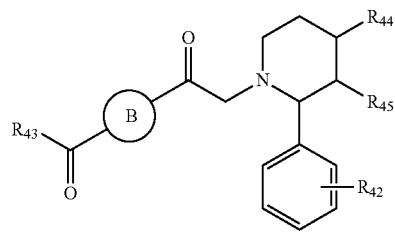

wherein $R_{42}$ is selected from the group consisting of H, —OCH₃, —OCF₃, halo and CH₃;

$R_{43}$ is selected from the group consisting of —CH=CH₂, and CH₂(halo);

ring B is selected from the group consisting of

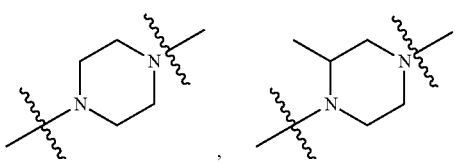

-continued

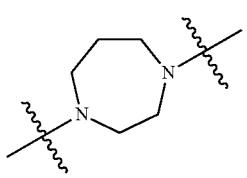

and form a cyclic ring selected from the group consisting of

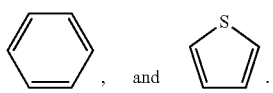

In one embodiment the present disclosure is directed to an HPV E6 binding compound of having the structure of

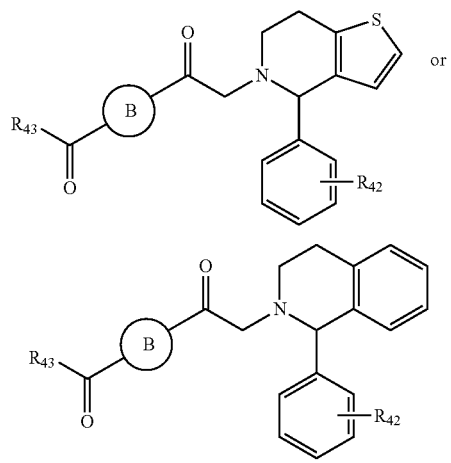

wherein $R_{42}$ is selected from the group consisting of H, —OCH$_3$, —OCF$_3$, halo and CH$_3$;

$R_{43}$ is selected from the group consisting of —CH=CH$_2$, and CH$_2$(halo), optionally wherein $R_{43}$ is —CH=CH$_2$; and ring B is selected from the group consisting of

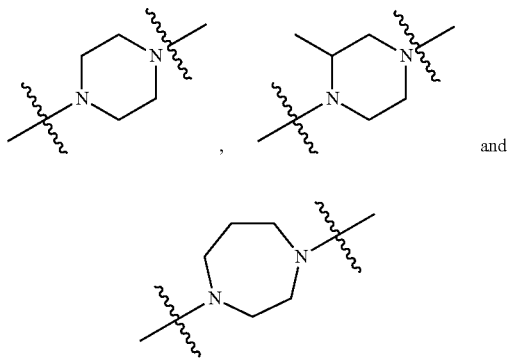

In one embodiment the present disclosure is directed to an HPV E6 binding compound having the structure of

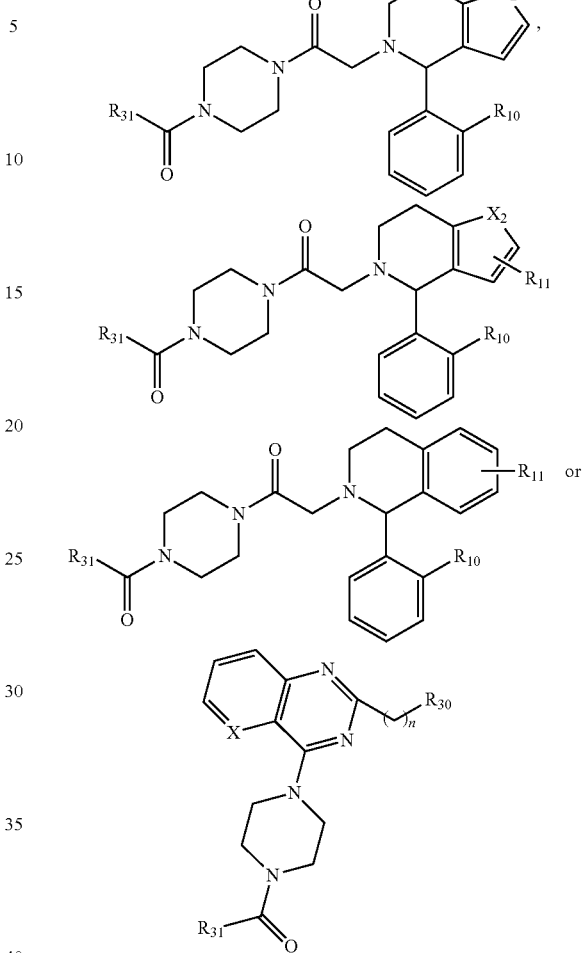

wherein
$R_{10}$ is H, CH$_3$, CF$_3$, OCH$_3$, OCF$_3$, CN or halo;
$R_{11}$ is H or OCH$_3$;
$X_2$ is C, O or S, optionally $X_2$ is C;
$R_{30}$ is selected from the group consisting of H, halo, cyclopropyl, and

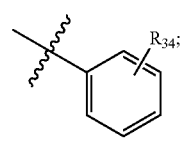

n is an integer selected from 1 to 4;
X is N or C;
$R_{31}$ is selected from the group consisting of —CH=CH$_2$, —CH=CHCH$_2$N(CH$_3$)$_2$, —CH=CHCH$_3$, CH$_2$(halo) and CH$_3$, optionally wherein $R_{31}$ is —CH=CHCH$_2$N(CH$_3$)$_2$, —CH=CH$_2$, or —CH=CHCH$_3$, optionally wherein $R_{31}$ is —CH=CH$_2$; and
$R_{34}$ is selected from the group consisting of H, —OCH$_3$, —OCF$_3$, and cyclopropyl.

Illustrative embodiments of compounds of the Formula I, Ia, Ib, II, III and IIIa are provided in Table 1.

TABLE 1

Illustrative embodiments of compounds of the Formula I, Ia, Ib, II, III and IIIa.

| Compound Number | Structure | Chemical Name |
|---|---|---|
| EIN-116 | 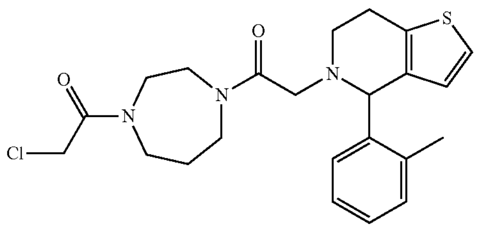 [SMILES: Cc1ccccc1C1c2ccsc2CCN1CC(=O)N1CCCN(C(=O)CCl)CC1] | 2-chloro-1-(4-(2-(4-(o-tolyl)-6,7-dihydrothieno[3,2-c]pyridin-5(4H)-yl)acetyl)-1,4-diazepan-1-yl)ethan-1-one |
| EIN-117 | 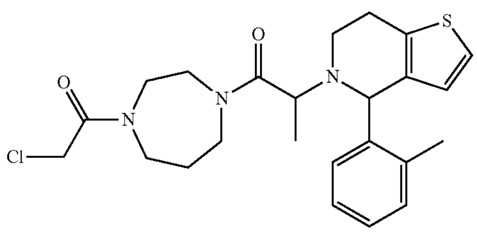 [SMILES: Cc1ccccc1C1c2ccsc2CCN1C(C)C(=O)N1CCCN(C(=O)CCl)CC1] | 1-(4-(2-chloroacetyl)-1,4-diazepan-1-yl)-2-(4-(o-tolyl)-6,7-dihydrothieno[3,2-c]pyridin-5(4H)-yl)propan-1-one |
| EIN-118 | 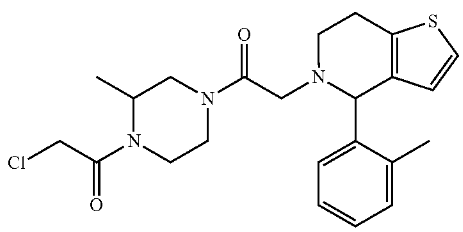 [SMILES: Cc1ccccc1C1c2ccsc2CCN1CC(=O)N1CCN(C(=O)CCl)C(C)C1] | 2-chloro-1-(2-methyl-4-(2-(4-(o-tolyl)-6,7-dihydrothieno[3,2-c]pyridin-5(4H)-yl)acetyl)piperazin-1-yl)ethan-1-one |
| EIN-119 | 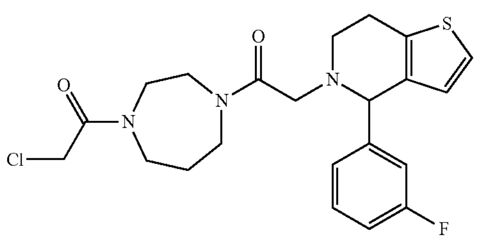 [SMILES: O=C(CCl)N1CCCN(C(=O)CN2CCc3sccc3C2c2cccc(F)c2)CC1] | 2-chloro-1-(4-(2-(4-(3-fluorophenyl)-6,7-dihydrothieno[3,2-c]pyridin-5(4H)-yl)acetyl)-1,4-diazepan-1-yl)ethan-1-one |
| EIN-120 | 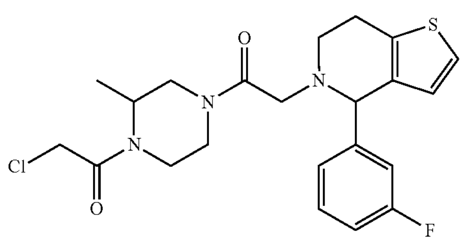 [SMILES: CC1CN(C(=O)CN2CCc3sccc3C2c2cccc(F)c2)CCN1C(=O)CCl] | 2-chloro-1-(4-(2-(4-(3-fluorophenyl)-6,7-dihydrothieno[3,2-c]pyridin-5(4H)-yl)acetyl)-2-methylpiperazin-1-yl)ethan-1-one |
| EIN-121 | 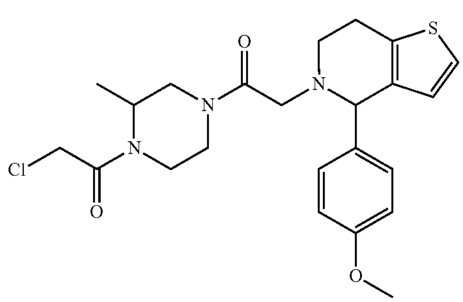 [SMILES: COc1ccc(C2c3ccsc3CCN2CC(=O)N2CCN(C(=O)CCl)C(C)C2)cc1] | 2-chloro-1-(4-(2-(4-(4-methoxyphenyl)-6,7-dihydrothieno[3,2-c]pyridin-5(4H)-yl)acetyl)-2-methylpiperazin-1-yl)ethan-1-one |

TABLE 1-continued

Illustrative embodiments of compounds of the Formula I, Ia, Ib, II, III and IIIa.

| Compound Number | Structure | Chemical Name |
|---|---|---|
| EIN-122 | 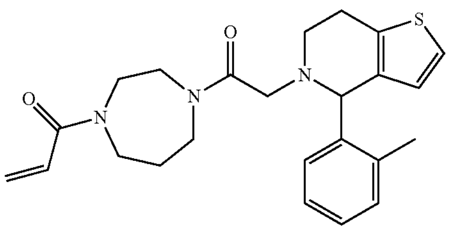 [SMILES: C=CC(=O)N1CCCN(C(=O)CN2CCc3sccc3C2c2ccccc2C)CC1] | 1-(4-(2-(4-(o-tolyl)-6,7-dihydrothieno[3,2-c]pyridin-5(4H)-yl)acetyl)-1,4-diazepan-1-yl)prop-2-en-1-one |
| EIN-123 | 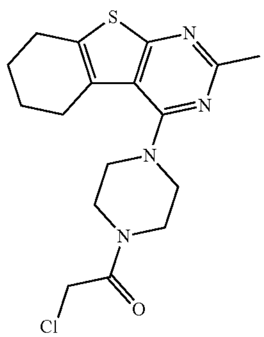 [SMILES: Cc1nc(N2CCN(C(=O)CCl)CC2)c2c3c(sc2n1)CCCC3] | 2-chloro-1-(4-(2-methyl-5,6,7,8-tetrahydrobenzo[4,5]thieno[2,3-d]pyrimidin-4-yl)piperazin-1-yl)ethan-1-one |
| EIN-124 | 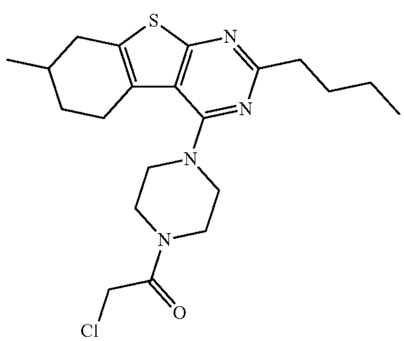 [SMILES: CCCCc1nc(N2CCN(C(=O)CCl)CC2)c2c3c(sc2n1)CC(C)CC3] | 1-(4-(2-butyl-7-methyl-5,6,7,8-tetrahydrobenzo[4,5]thieno[2,3-d]pyrimidin-4-yl)piperazin-1-yl)-2-chloroethan-1-one |
| EIN-125 | 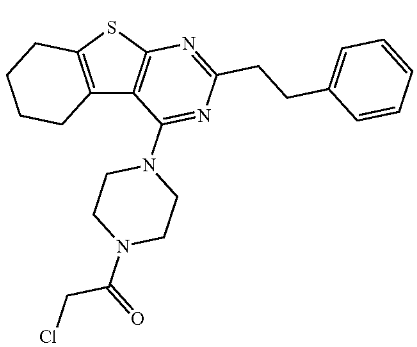 [SMILES: O=C(CCl)N1CCN(c2nc(CCc3ccccc3)nc3sc4c(c23)CCCC4)CC1] | 2-chloro-1-(4-(2-phenethyl-5,6,7,8-tetrahydrobenzo[4,5]thieno[2,3-d]pyrimidin-4-yl)piperazin-1-yl)ethan-1-one |

TABLE 1-continued

Illustrative embodiments of compounds of the Formula I, Ia, Ib, II, III and IIIa.

| Compound Number | Structure | Chemical Name |
|---|---|---|
| EIN-126 | 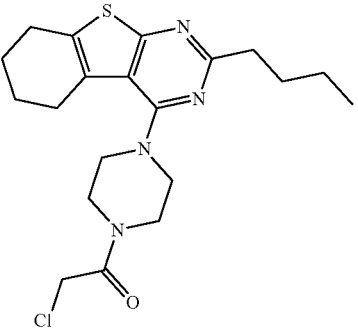 [SMILES: CCCCc1nc(N2CCN(C(=O)CCl)CC2)c2c3c(sc2n1)CCCC3] | 1-(4-(2-butyl-5,6,7,8-tetrahydrobenzo[4,5]thieno[2,3-d]pyrimidin-4-yl)piperazin-1-yl)-2-chloroethan-1-one |
| EIN-127 | 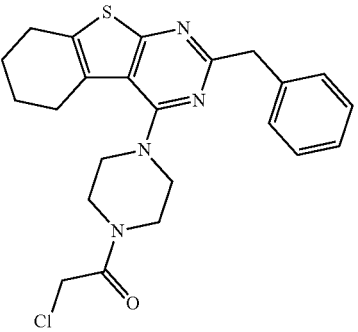 [SMILES: O=C(CCl)N1CCN(c2nc(Cc3ccccc3)nc3sc4c(c23)CCCC4)CC1] | 1-(4-(2-benzyl-5,6,7,8-tetrahydrobenzo[4,5]thieno[2,3-d]pyrimidin-4-yl)piperazin-1-yl)-2-chloroethan-1-one |
| EIN-128 | 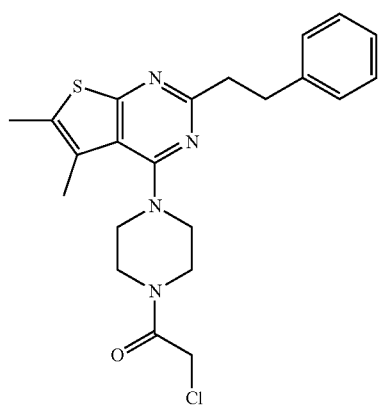 [SMILES: Cc1sc2nc(CCc3ccccc3)nc(N3CCN(C(=O)CCl)CC3)c2c1C] | 2-chloro-1-(4-(5,6-dimethyl-2-phenethylthieno[2,3-d]pyrimidin-4-yl)piperazin-1-yl)ethan-1-one |
| EIN-129 | 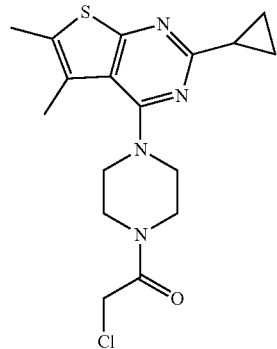 [SMILES: Cc1sc2nc(C3CC3)nc(N3CCN(C(=O)CCl)CC3)c2c1C] | 2-chloro-1-(4-(2-cyclopropyl-5,6-dimethylthieno[2,3-d]pyrimidin-4-yl)piperazin-1-yl)ethan-1-one |

TABLE 1-continued

Illustrative embodiments of compounds of the Formula I, Ia, Ib, II, III and IIIa.

| Compound Number | Structure | Chemical Name |
| --- | --- | --- |
| EIN-130 | 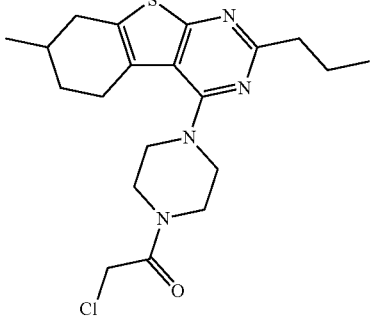 | 2-chloro-1-(4-(7-methyl-2-propyl-5,6,7,8-tetrahydrobenzo[4,5]thieno[2,3-d]pyrimidin-4-yl)piperazin-1-yl)ethan-1-one |
| EIN-131 | 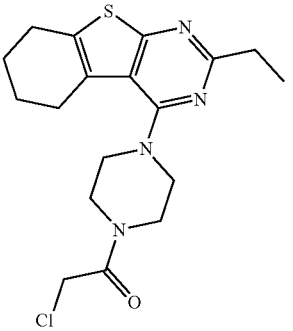 [SMILES: CCc1nc(N2CCN(C(=O)CCl)CC2)c2c3c(sc2n1)CCCC3] | 2-chloro-1-(4-(2-ethyl-5,6,7,8-tetrahydrobenzo[4,5]thieno[2,3-d]pyrimidin-4-yl)piperazin-1-yl)ethan-1-one |
| EIN-132 | 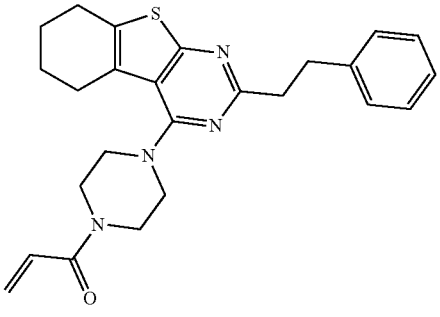 [SMILES: C=CC(=O)N1CCN(c2nc(CCc3ccccc3)nc3sc4c(c23)CCCC4)CC1] | 1-(4-(2-phenethyl-5,6,7,8-tetrahydrobenzo[4,5]thieno[2,3-d]pyrimidin-4-yl)piperazin-1-yl)prop-2-en-1-one |
| EIN-133 | 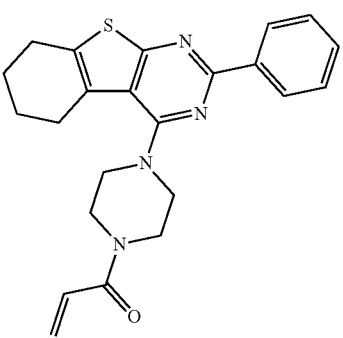 [SMILES: C=CC(=O)N1CCN(c2nc(-c3ccccc3)nc3sc4c(c23)CCCC4)CC1] | 1-(4-(2-phenyl-5,6,7,8-tetrahydrobenzo[4,5]thieno[2,3-d]pyrimidin-4-yl)piperazin-1-yl)prop-2-en-1-one |

TABLE 1-continued

Illustrative embodiments of compounds of the Formula I, Ia, Ib, II, III and IIIa.

| Compound Number | Structure | Chemical Name |
| --- | --- | --- |
| EIN-134 | 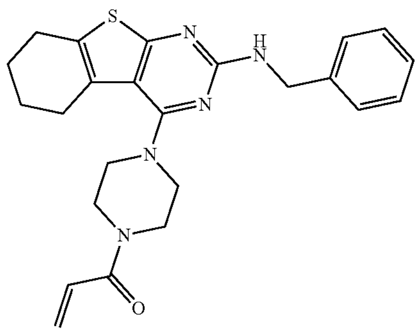 [SMILES: C=CC(=O)N1CCN(c2nc(NCc3ccccc3)nc3sc4c(c23)CCCC4)CC1] | 1-(4-(2-(benzylamino)-5,6,7,8-tetrahydrobenzo[4,5]thieno[2,3-d]pyrimidin-4-yl)piperazin-1-yl)prop-2-en-1-one |
| EIN-135 | 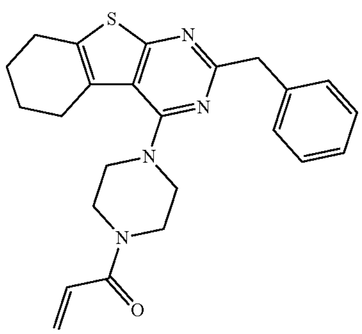 [SMILES: C=CC(=O)N1CCN(c2nc(Cc3ccccc3)nc3sc4c(c23)CCCC4)CC1] | 1-(4-(2-benzyl-5,6,7,8-tetrahydrobenzo[4,5]thieno[2,3-d]pyrimidin-4-yl)piperazin-1-yl)prop-2-en-1-one |
| EIN-136 | 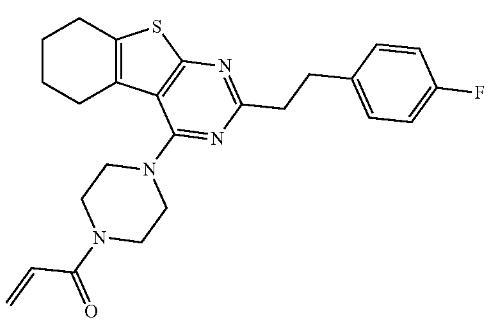 [SMILES: C=CC(=O)N1CCN(c2nc(CCc3ccc(F)cc3)nc3sc4c(c23)CCCC4)CC1] | 1-(4-(2-(4-fluorophenethyl)-5,6,7,8-tetrahydrobenzo[4,5]thieno[2,3-d]pyrimidin-4-yl)piperazin-1-yl)prop-2-en-1-one |
| EIN-137 | 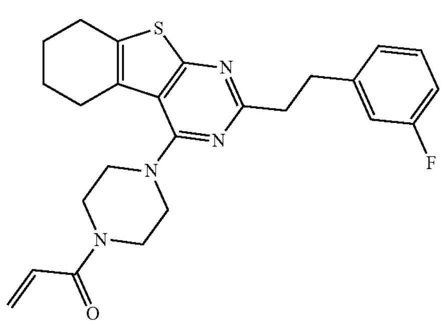 [SMILES: C=CC(=O)N1CCN(c2nc(CCc3cccc(F)c3)nc3sc4c(c23)CCCC4)CC1] | 1-(4-(2-(3-fluorophenethyl)-5,6,7,8-tetrahydrobenzo[4,5]thieno[2,3-d]pyrimidin-4-yl)piperazin-1-yl)prop-2-en-1-one |

TABLE 1-continued

Illustrative embodiments of compounds of the Formula I, Ia, Ib, II, III and IIIa.

| Compound Number | Structure | Chemical Name |
|---|---|---|
| EIN-138 | 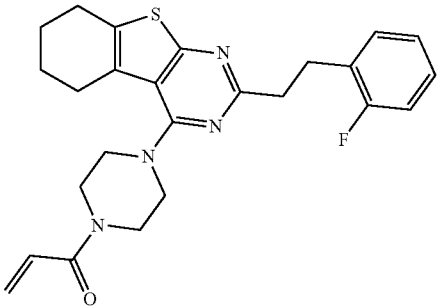 [SMILES: C=CC(=O)N1CCN(c2nc(CCc3ccccc3F)nc3sc4c(c23)CCCC4)CC1] | 1-(4-(2-(2-fluorophenethyl)-5,6,7,8-tetrahydrobenzo[4,5]thieno[2,3-d]pyrimidin-4-yl)piperazin-1-yl)prop-2-en-1-one |
| EIN-139 | 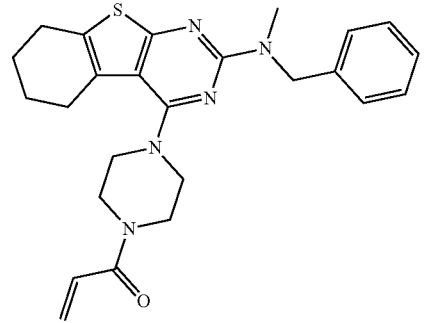 [SMILES: C=CC(=O)N1CCN(c2nc(N(C)Cc3ccccc3)nc3sc4c(c23)CCCC4)CC1] | 1-(4-(2-(benzyl(methyl)amino)-5,6,7,8-tetrahydrobenzo[4,5]thieno[2,3-d]pyrimidin-4-yl)piperazin-1-yl)prop-2-en-1-one |
| EIN-140 | 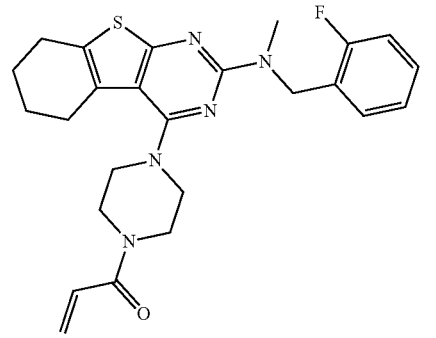 [SMILES: C=CC(=O)N1CCN(c2nc(N(C)Cc3ccccc3F)nc3sc4c(c23)CCCC4)CC1] | 1-(4-(2-((2-fluorobenzyl)(methyl)amino)-5,6,7,8-tetrahydrobenzo[4,5]thieno[2,3-d]pyrimidin-4-yl)piperazin-1-yl)prop-2-en-1-one |
| EIN-141 | 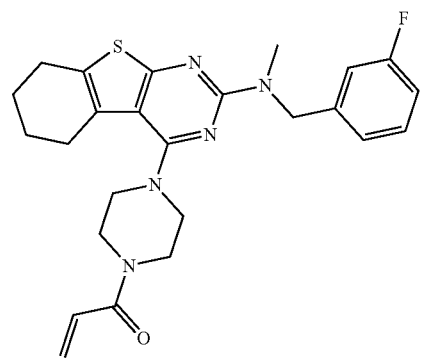 [SMILES: C=CC(=O)N1CCN(c2nc(N(C)Cc3cccc(F)c3)nc3sc4c(c23)CCCC4)CC1] | 1-(4-(2-((3-fluorobenzyl)(methyl)amino)-5,6,7,8-tetrahydrobenzo[4,5]thieno[2,3-d]pyrimidin-4-yl)piperazin-1-yl)prop-2-en-1-one |

TABLE 1-continued

Illustrative embodiments of compounds of the Formula I, Ia, Ib, II, III and IIIa.

| Compound Number | Structure | Chemical Name |
|---|---|---|
| EIN-142 | 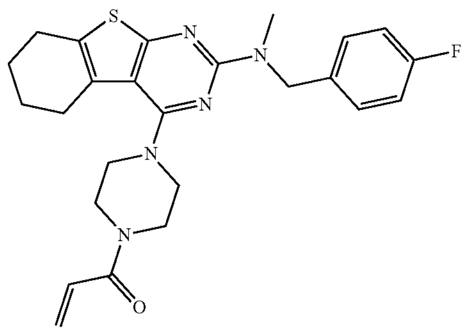 [SMILES: C=CC(=O)N1CCN(c2nc(N(C)Cc3ccc(F)cc3)nc3sc4c(c23)CCCC4)CC1] | 1-(4-(2-((4-fluorobenzyl)(methyl)amino)-5,6,7,8-tetrahydrobenzo[4,5]thieno[2,3-d]pyrimidin-4-yl)piperazin-1-yl)prop-2-en-1-one |
| EIN-143 | 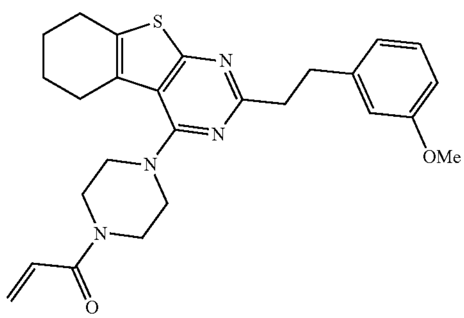 [SMILES: C=CC(=O)N1CCN(c2nc(CCc3cccc(OC)c3)nc3sc4c(c23)CCCC4)CC1] | 1-(4-(2-(3-methoxyphenethyl)-5,6,7,8-tetrahydrobenzo[4,5]thieno[2,3-d]pyrimidin-4-yl)piperazin-1-yl)prop-2-en-1-one |
| EIN-144 | 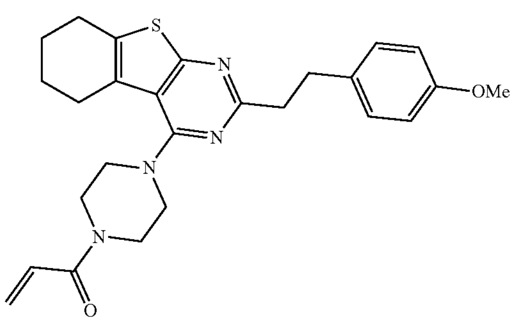 [SMILES: C=CC(=O)N1CCN(c2nc(CCc3ccc(OC)cc3)nc3sc4c(c23)CCCC4)CC1] | 1-(4-(2-(4-methoxyphenethyl)-5,6,7,8-tetrahydrobenzo[4,5]thieno[2,3-d]pyrimidin-4-yl)piperazin-1-yl)prop-2-en-1-one |
| EIN-145 | 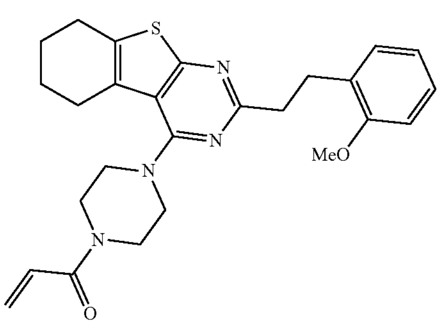 [SMILES: C=CC(=O)N1CCN(c2nc(CCc3ccccc3OC)nc3sc4c(c23)CCCC4)CC1] | 1-(4-(2-(2-methoxyphenethyl)-5,6,7,8-tetrahydrobenzo[4,5]thieno[2,3-d]pyrimidin-4-yl)piperazin-1-yl)prop-2-en-1-one |

TABLE 1-continued

Illustrative embodiments of compounds of the Formula I, Ia, Ib, II, III and IIIa.

| Compound Number | Structure | Chemical Name |
| --- | --- | --- |
| EIN-146 | 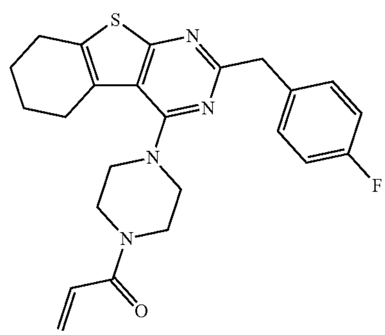 [SMILES: C=CC(=O)N1CCN(c2nc(Cc3ccc(F)cc3)nc3sc4c(c23)CCCC4)CC1] | 1-(4-(2-(4-fluorobenzyl)-5,6,7,8-tetrahydrobenzo[4,5]thieno[2,3-d]pyrimidin-4-yl)piperazin-1-yl)prop-2-en-1-one |
| EIN-147 | 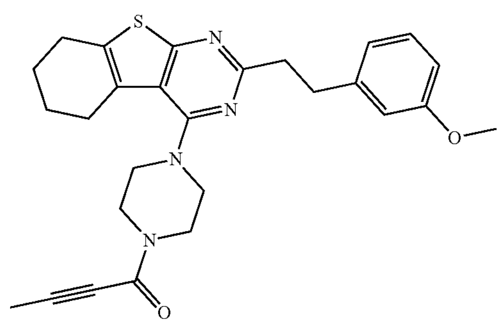 [SMILES: CC#CC(=O)N1CCN(c2nc(CCc3cccc(OC)c3)nc3sc4c(c23)CCCC4)CC1] | 1-(4-(2-(3-methoxyphenethyl)-5,6,7,8-tetrahydrobenzo[4,5]thieno[2,3-d]pyrimidin-4-yl)piperazin-1-yl)but-2-yn-1-one |
| EIN-148 | 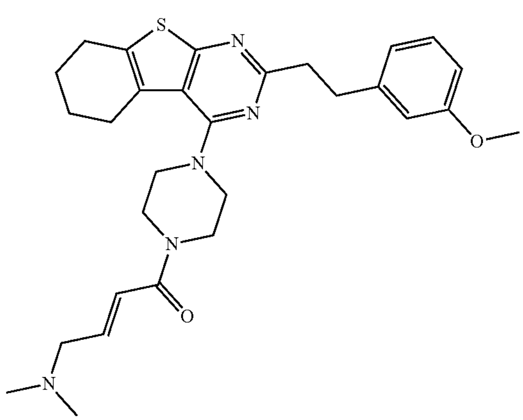 | (E)-4-(dimethylamino)-1-(4-(2-(3-methoxyphenethyl)-5,6,7,8-tetrahydrobenzo[4,5]thieno[2,3-d]pyrimidin-4-yl)piperazin-1-yl)but-2-en-1-one |
| EIN-150 | 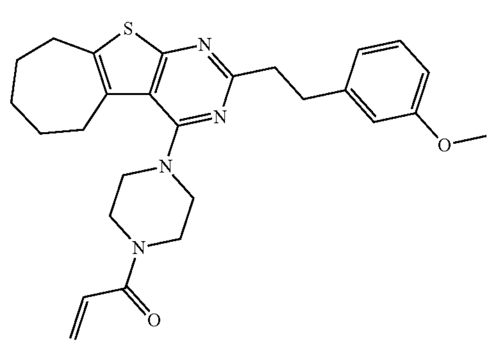 [SMILES: C=CC(=O)N1CCN(c2nc(CCc3cccc(OC)c3)nc3sc4c(c23)CCCCC4)CC1] | 1-(4-(2-(3-methoxyphenethyl)-6,7,8,9-tetrahydro-5H-cyclohepta[4,5]thieno[2,3-d]pyrimidin-4-yl)piperazin-1-yl)prop-2-en-1-one |

TABLE 1-continued

Illustrative embodiments of compounds of the Formula I, Ia, Ib, II, III and IIIa.

| Compound Number | Structure | Chemical Name |
|---|---|---|
| EIN-151 | 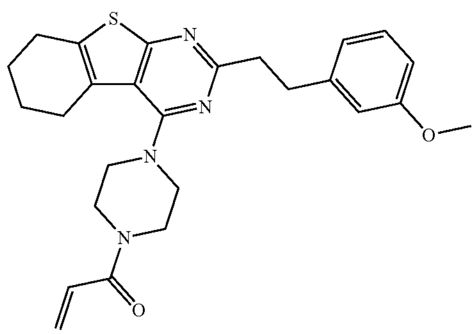 [SMILES: C=CC(=O)N1CCN(c2nc(CCc3cccc(OC)c3)nc3sc4c(c23)CCCC4)CC1] | 1-(4-(2-(3-methoxyphenethyl)-5,6,7,8-tetrahydrobenzo[4,5]thieno[2,3-d]pyrimidin-4-yl)piperazin-1-yl)prop-2-en-1-one |
| EIN-152 | 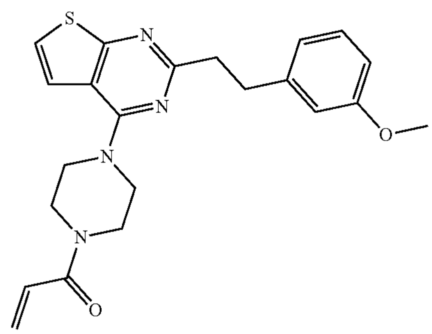 [SMILES: C=CC(=O)N1CCN(c2nc(CCc3cccc(OC)c3)nc3sccc23)CC1] | 1-(4-(2-(3-methoxyphenethyl)thieno[2,3-d]pyrimidin-4-yl)piperazin-1-yl)prop-2-en-1-one |
| EIN-153 | 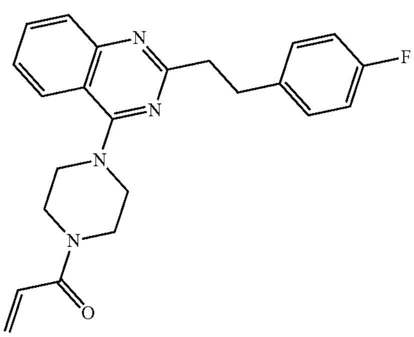 [SMILES: C=CC(=O)N1CCN(c2nc(CCc3ccc(F)cc3)nc3ccccc23)CC1] | 1-(4-(2-(4-fluorophenethyl)quinazolin-4-yl)piperazin-1-yl)prop-2-en-1-one |
| EIN-154 | 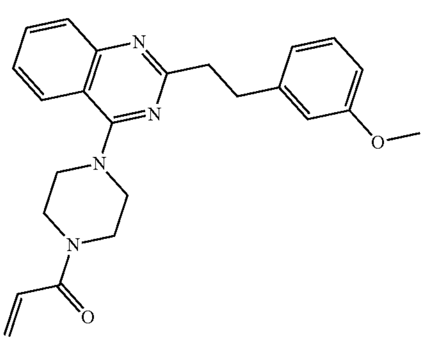 [SMILES: C=CC(=O)N1CCN(c2nc(CCc3cccc(OC)c3)nc3ccccc23)CC1] | 1-(4-(2-(3-methoxyphenethyl)quinazolin-4-yl)piperazin-1-yl)prop-2-en-1-one |

TABLE 1-continued

Illustrative embodiments of compounds of the Formula I, Ia, Ib, II, III and IIIa.

| Compound Number | Structure | Chemical Name |
| --- | --- | --- |
| EIN-155 | 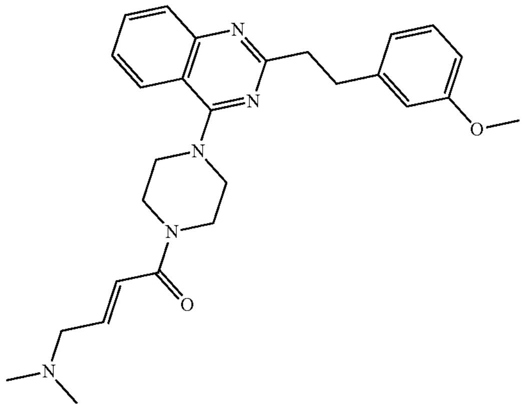 | (E)-4-(dimethylamino)-1-(4-(2-(3-methoxyphenethyl)quinazolin-4-yl)piperazin-1-yl)but-2-en-1-one |
| EIN-156 | 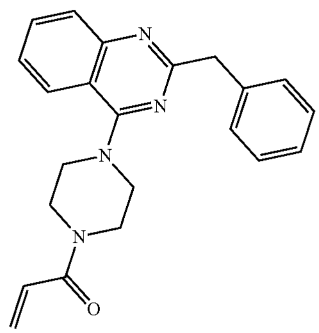 [SMILES: C=CC(=O)N1CCN(c2nc(Cc3ccccc3)nc3ccccc23)CC1] | 1-(4-(2-benzylquinazolin-4-yl)piperazin-1-yl)prop-2-en-1-one |
| EIN-157 | 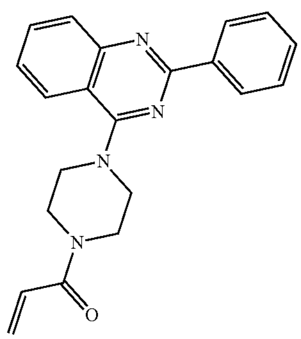 [SMILES: C=CC(=O)N1CCN(c2nc(-c3ccccc3)nc3ccccc23)CC1] | 1-(4-(2-phenylquinazolin-4-yl)piperazin-1-yl)prop-2-en-1-one |
| EIN-158 | 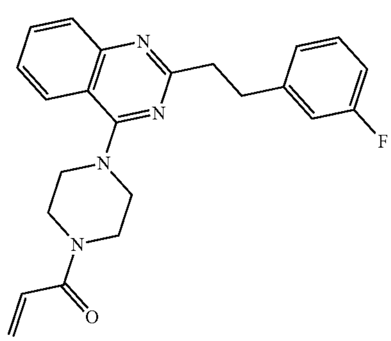 [SMILES: C=CC(=O)N1CCN(c2nc(CCc3cccc(F)c3)nc3ccccc23)CC1] | 1-(4-(2-(3-fluorophenethyl)quinazolin-4-yl)piperazin-1-yl)prop-2-en-1-one |

TABLE 1-continued

Illustrative embodiments of compounds of the Formula I, Ia, Ib, II, III and IIIa.

| Compound Number | Structure | Chemical Name |
|---|---|---|
| EIN-159 | 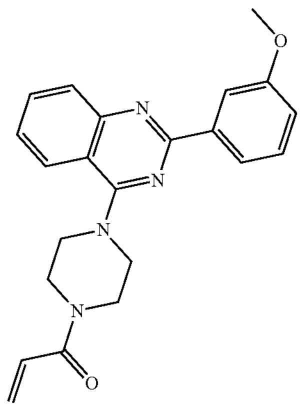 [SMILES: C=CC(=O)N1CCN(c2nc(-c3cccc(OC)c3)nc3ccccc23)CC1] | 1-(4-(2-(3-methoxyphenyl)quinazolin-4-yl)piperazin-1-yl)prop-2-en-1-one |
| EIN-160 | 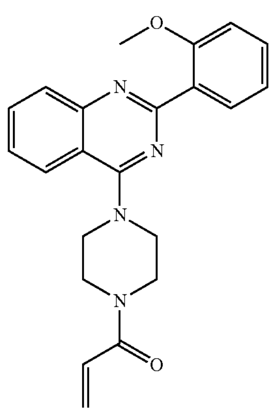 [SMILES: C=CC(=O)N1CCN(c2nc(-c3ccccc3OC)nc3ccccc23)CC1] | 1-(4-(2-(2-methoxyphenyl)quinazolin-4-yl)piperazin-1-yl)prop-2-en-1-one |
| EIN-161 | 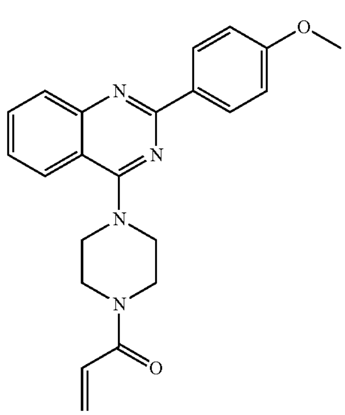 [SMILES: C=CC(=O)N1CCN(c2nc(-c3ccc(OC)cc3)nc3ccccc23)CC1] | 1-(4-(2-(4-methoxyphenyl)quinazolin-4-yl)piperazin-1-yl)prop-2-en-1-one |

TABLE 1-continued

Illustrative embodiments of compounds of the Formula I, Ia, Ib, II, III and IIIa.

| Compound Number | Structure | Chemical Name |
|---|---|---|
| EIN-162 | 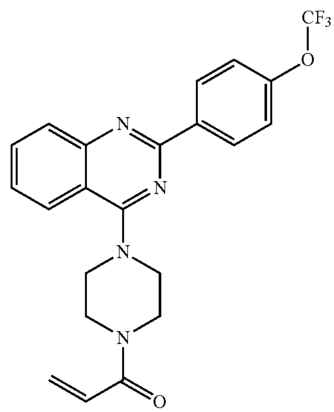 [SMILES: C=CC(=O)N1CCN(c2nc(-c3ccc(OC(F)(F)F)cc3)nc3ccccc23)CC1] | 1-(4-(2-(4-(trifluoromethoxy)phenyl)quinazolin-4-yl)piperazin-1-yl)prop-2-en-1-one |
| EIN-163 | 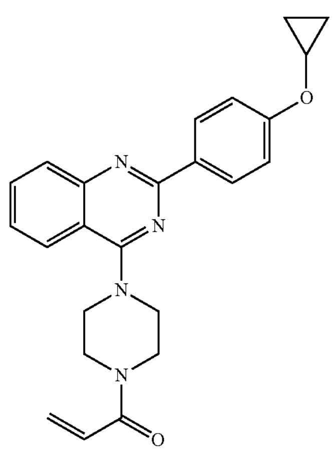 [SMILES: C=CC(=O)N1CCN(c2nc(-c3ccc(OC4CC4)cc3)nc3ccccc23)CC1] | 1-(4-(2-(4-cyclopropoxyphenyl)quinazolin-4-yl)piperazin-1-yl)prop-2-en-1-one |
| EIN-164 | 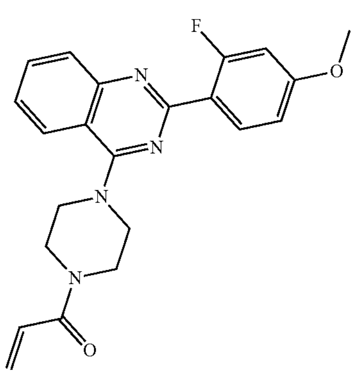 [SMILES: C=CC(=O)N1CCN(c2nc(-c3ccc(OC)cc3F)nc3ccccc23)CC1] | 1-(4-(2-(2-fluoro-4-methoxyphenyl)quinazolin-4-yl)piperazin-1-yl)prop-2-en-1-one |

TABLE 1-continued

Illustrative embodiments of compounds of the Formula I, Ia, Ib, II, III and IIIa.

| Compound Number | Structure | Chemical Name |
|---|---|---|
| EIN-165 | 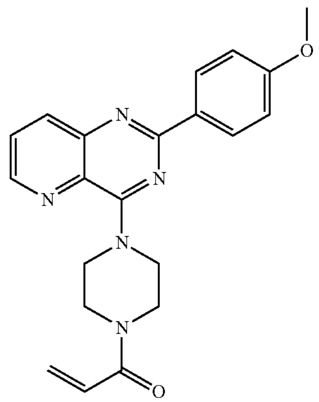 [SMILES: C=CC(=O)N1CCN(c2nc(-c3ccc(OC)cc3)nc3cccnc23)CC1] | 1-(4-(2-(4-methoxyphenyl)pyrido[3,2-d]pyrimidin-4-yl)piperazin-1-yl)prop-2-en-1-one |
| EIN-166 | 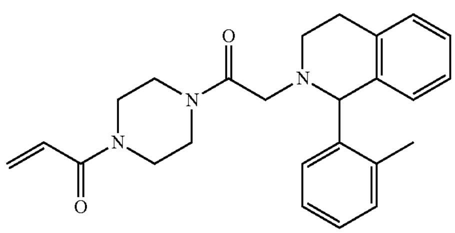 [SMILES: C=CC(=O)N1CCN(C(=O)CN2CCc3ccccc3C2c2ccccc2C)CC1] | 1-(4-(2-(1-(o-tolyl)-3,4-dihydroisoquinolin-2(1H)-yl)acetyl)piperazin-1-yl)prop-2-en-1-one |

Other representative structures of the present disclose include, but are not limited to, the following:

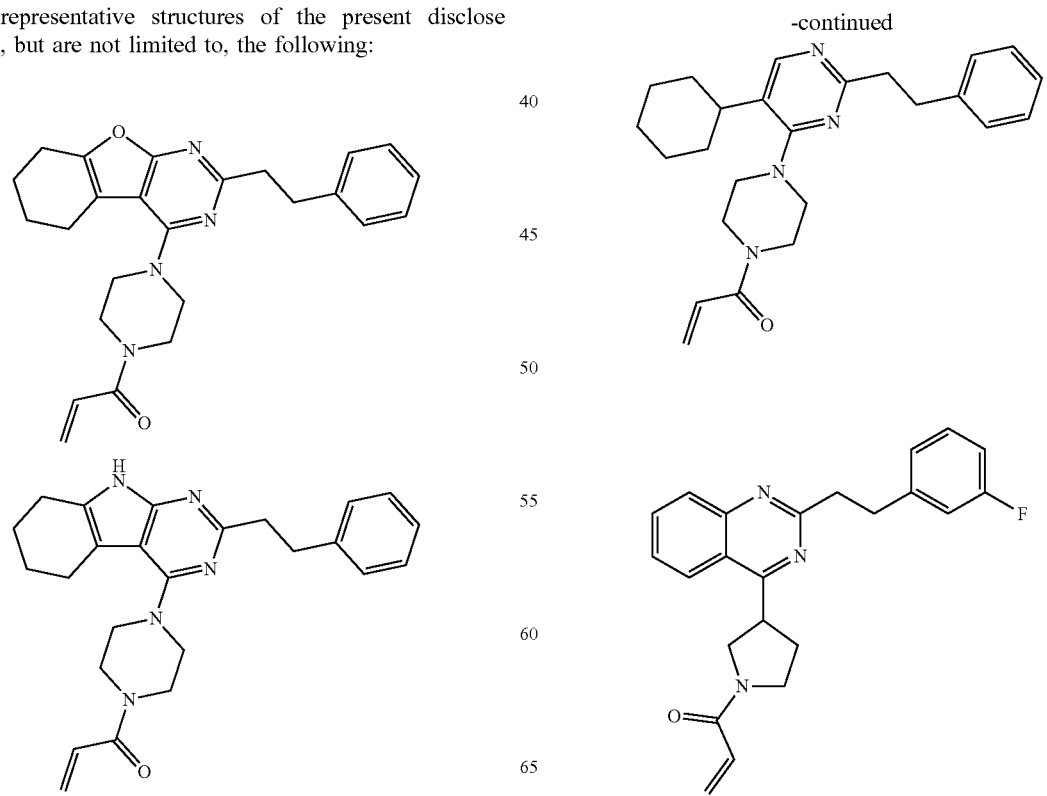

57
-continued
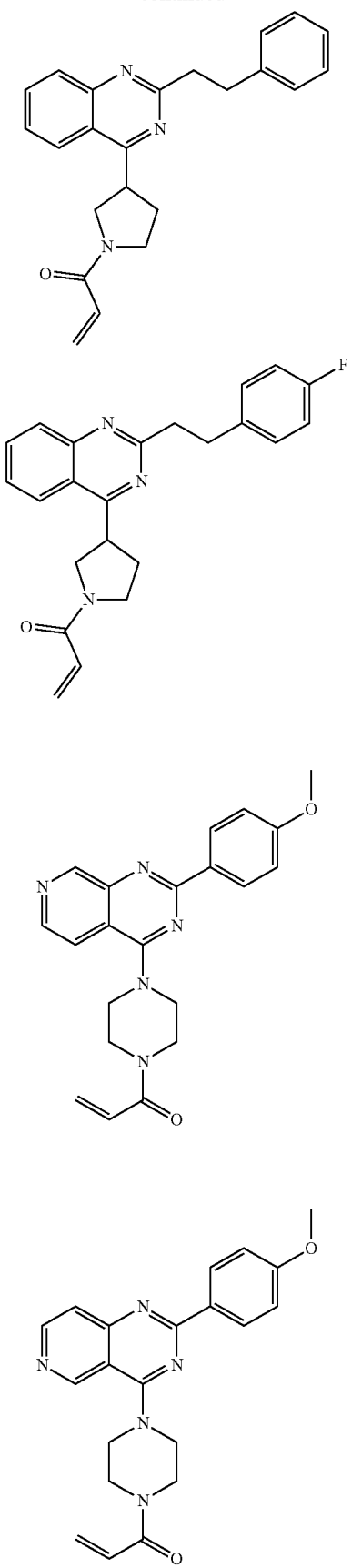
58
-continued
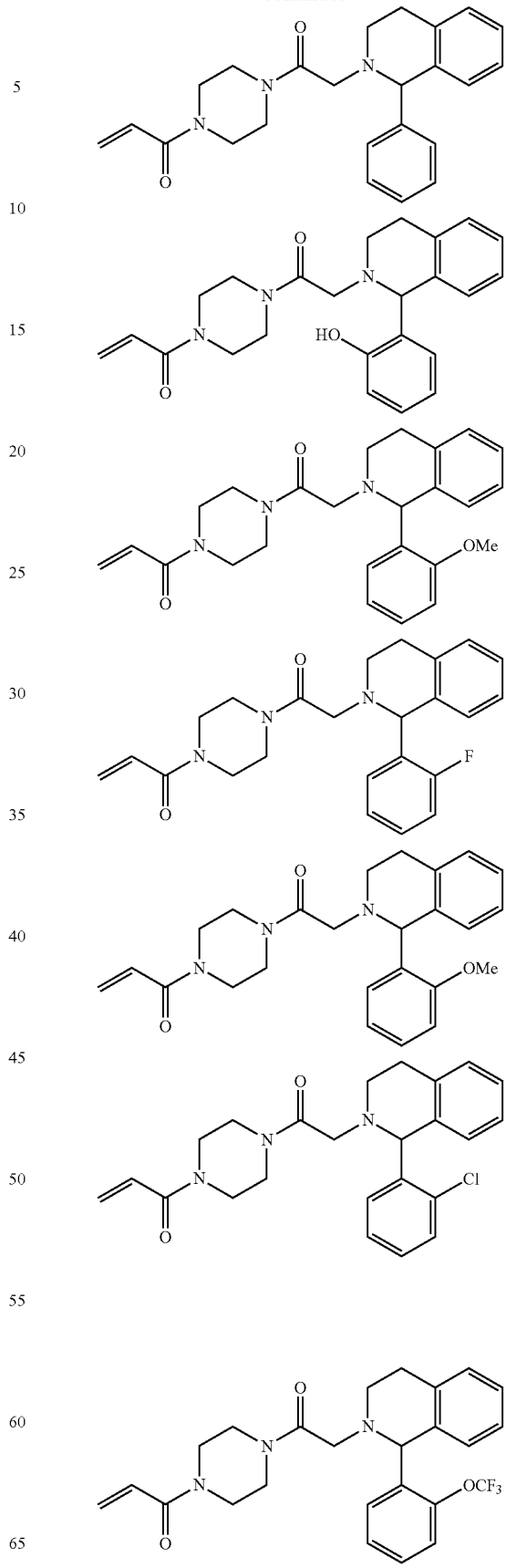

-continued

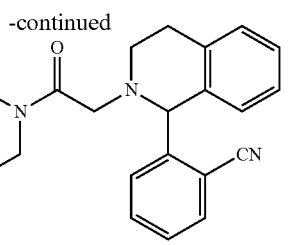

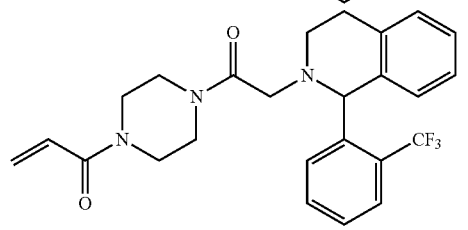

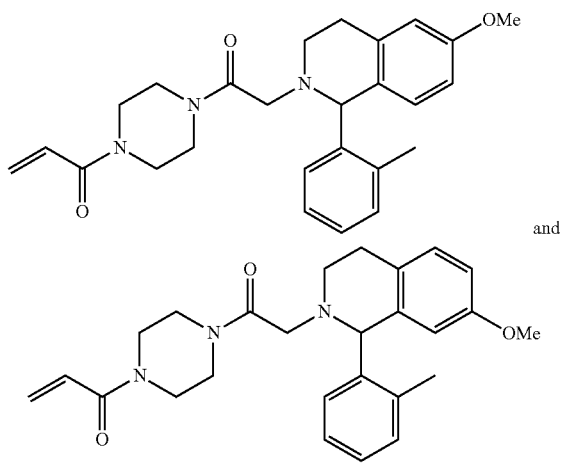

and

Those skilled in the art will recognize that the species listed or illustrated herein are not exhaustive, and that additional species within the scope of these defined terms may be selected.

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the invention are sterile compositions. Pharmaceutical compositions may be prepared using compounding techniques known or that become available to those skilled in the art.

Sterile compositions are also contemplated by the invention, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the invention may be administered by a suitable route of delivery, such as oral, parenteral, intravenous, subcutaneous injection, rectal, nasal, topical, or ocular routes, or by inhalation.

In one embodiment, the compositions are formulated for topical administration. For topical applications, the compounds of the present invention are preferably formulated as creams, ointments, lotions, gels, or a similar vehicle suitable for topical administration. For topical administration, the inventive compounds may be mixed with a pharmaceutical carrier at a concentration of about 0.1% to about 10% of drug to vehicle. Another mode of administering the agents of the invention may utilize a patch formulation to effect transdermal delivery.

The pharmaceutical composition of the present disclosure can be used to ameliorating or preventing the worsening of existing HPV disease symptoms, preventing additional symptoms from occurring, ameliorating or preventing the underlying systemic causes of symptoms, inhibiting the disorder or disease, e.g., arresting the development of HPV infection and/or associated symptoms, relieving the disorder or disease, causing regression of the disorder or disease, relieving a condition caused by the disease or disorder, or stopping the symptoms of the disease or disorder.

Exemplary diseases include but are not limited to HPV infections of the vagina, cervix, perineum, rectum, anus, penis, vulva, vagina, skin, and oropharynx. These may be subclinical and detected by ultrasensitive molecular diagnostic tests. Diseases includes histologically benign infected epithelium, pre-malignant and dysplastic lesions, carcinoma-in-situ, invasive cancer, and metastatic cancers induced by HPV.

In one embodiment of the methods of the invention, an effective amount of the HPV E6 binding compounds disclosed herein is provided to inhibit the target protein. Measuring such target modulation may be performed by routine analytical methods such as those described below. Such modulation is useful in a variety of settings, including in vitro assays. In such methods, the cell is infected with HPV.

In one embodiment the treatment methods provide an effective amount of one or more of the active compounds disclosed herein sufficient to generally bring about the desired therapeutic benefit in subjects needing such treatment. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about from about 0.1 mg to 1 g daily, or about 1 mg to 50 mg daily, or about 50 to 250 mg daily, or about 250 mg to 1 g daily. The total dosage may be given in single or divided dosage units (e.g., BID, TID, QID). An exemplary dose for topical administration may be in a formulation with 0.01%-10% of the E6 inhibitory compound.

In accordance with clause 1 a compound is provided comprising a structure of formula I

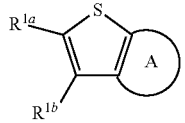      I wherein ring A is

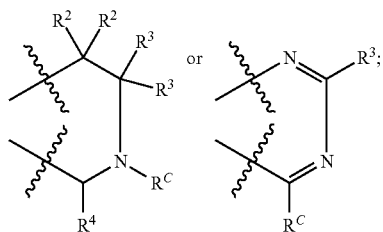

- $R^{1a}$ and $R^{1b}$ are independently H, deuterium, or $C_1$-$C_6$ alkyl, or $R^{1a}$ and $R^{1b}$ together with the carbon atoms to which they are attached combine to form a $C_3$-$C_8$ cycloalkyl, wherein each hydrogen atom in $C_1$-$C_6$ alkyl and $C_3$-$C_8$ cycloalkyl is optionally substituted with $R^D$;
- each $R^2$ is H;
- each $R^3$ is independently H, deuterium, $C_1$-$C_6$ alkyl, $C_3$-$C_6$ cycloalkyl, $C_6$-$C_{10}$ aryl, —NH($R^A$), or —N($R^A$)($R^B$), wherein each hydrogen atom in $C_6$-$C_{10}$ aryl is optionally substituted by $R^D$, and wherein each hydrogen atom in $C_1$-$C_6$ alkyl and $C_3$-$C_6$ cycloalkyl is optionally substituted by $C_6$-$C_{10}$ aryl optionally substituted with at least one $R^D$;
- $R^4$ is $C_6$-$C_{10}$ aryl, wherein each hydrogen atom is $C_6$-$C_{10}$ is optionally substituted with $R^D$;
- $R^A$ and $R^B$ are independently $C_1$-$C_6$ alkyl, wherein each hydrogen atom in $C_1$-$C_6$ alkyl is optionally substituted by $C_6$-$C_{10}$ aryl, wherein each hydrogen atom is $C_6$-$C_{10}$ aryl is optionally substituted with $R^D$;
- $R^C$ is $C_1$-$C_6$ alkyl, $C_3$-$C_8$ heterocycloalkyl, or —$C_1$-$C_6$ alkyl-$C_3$-$C_8$ heterocycloalkyl, wherein each hydrogen atom in $C_1$-$C_6$ alkyl and $C_3$-$C_8$ heterocycloalkyl is optionally substituted with $C_1$-$C_6$ alkyl, oxo, $C_3$-$C_8$ heterocycloalkyl, or $R^E$, provided $R^C$ includes at least one $R^E$;
- each $R^D$ is independently deuterium, halogen, $C_1$-$C_6$ alkyl, or —O$C_1$-$C_6$ alkyl, wherein each hydrogen atom in $C_1$-$C_6$ alkyl is optionally substituted with deuterium, halogen, or oxo;
- $R^E$ is $C_1$-$C_6$ alkyl, $C_2$-$C_6$ alkenyl, or $C_3$-$C_6$ alkynyl, wherein each hydrogen atom in $C_1$-$C_6$ alkyl, $C_2$-$C_6$ alkenyl, and $C_3$-$C_6$ alkynyl is optionally substituted with halogen, oxo, or —N($C_1$-$C_6$ alkyl)$_2$, provided at least one hydrogen atom in $C_1$-$C_6$ alkyl, $C_2$-$C_6$ alkenyl, and $C_3$-$C_6$ alkynyl is substituted with halogen, oxo, or —N($C_1$-$C_6$ alkyl)$_2$;

or a pharmaceutically acceptable salt thereof;

optionally provided the compound is not

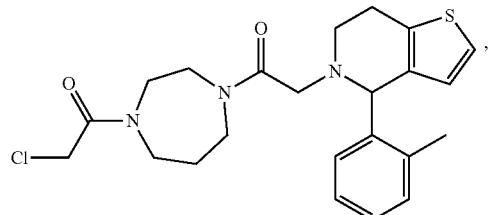,

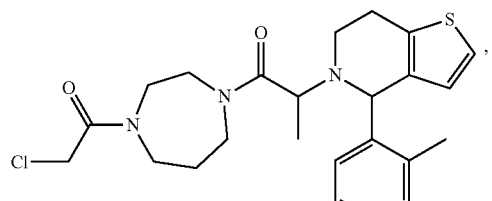,

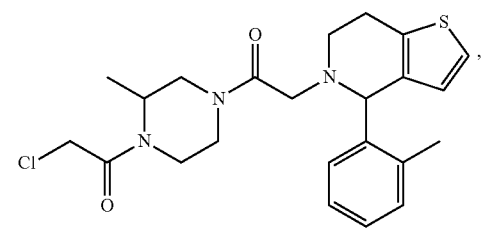,

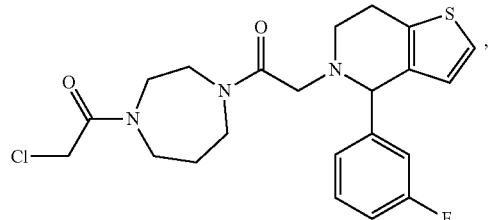,

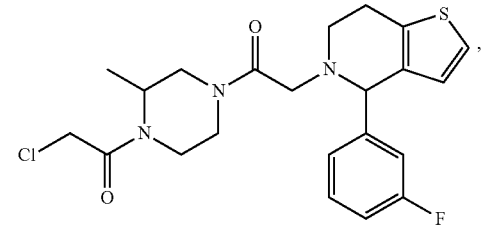,

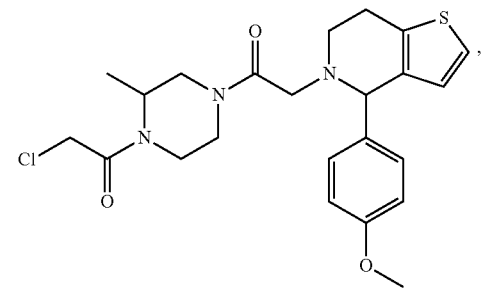,

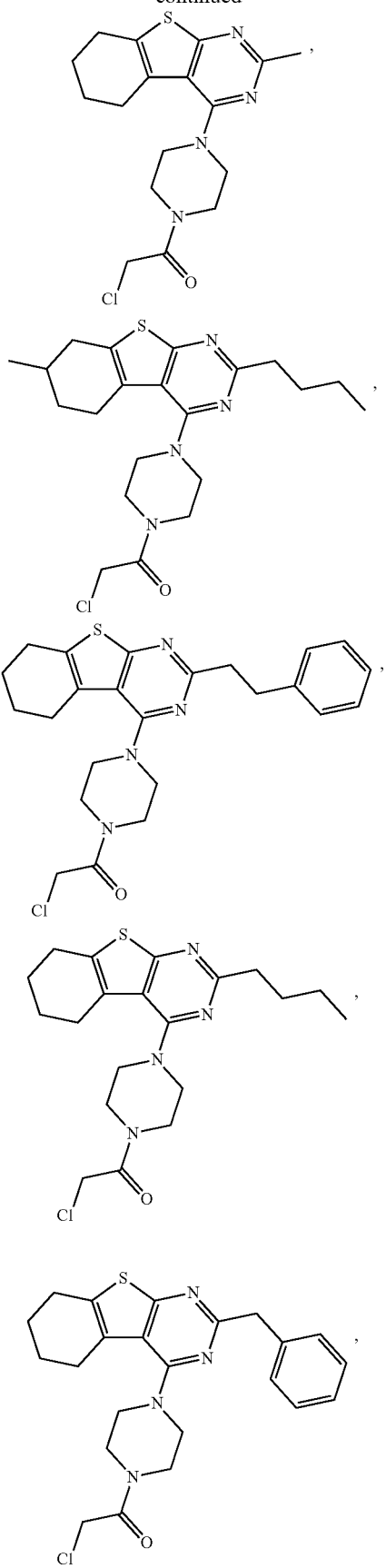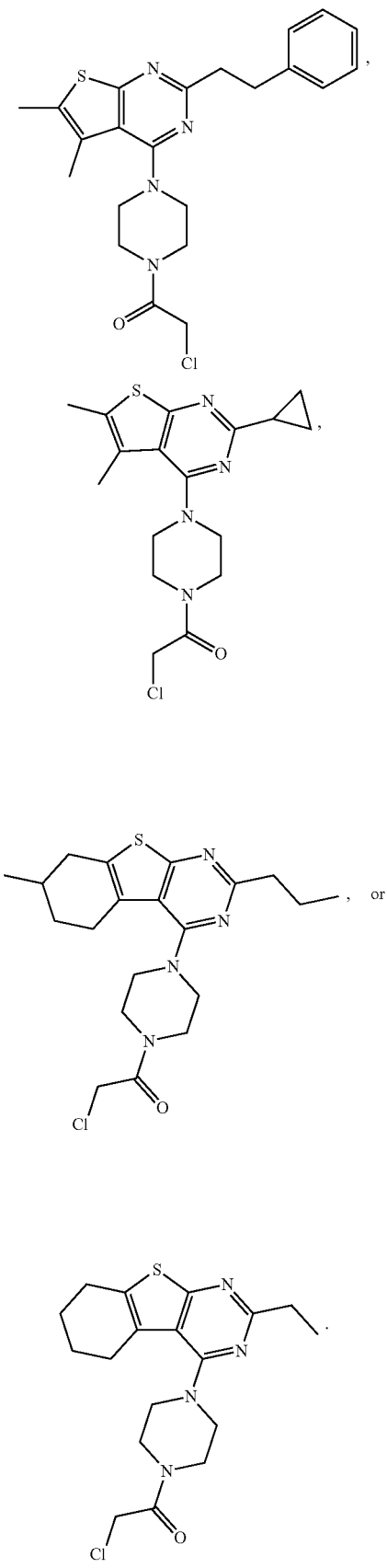

In accordance with clause 2 a compound or salt thereof of clause 1 is provided, wherein the compound is of the formula Ia

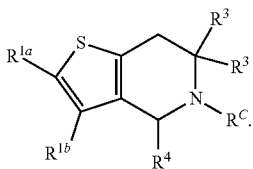

In accordance with clause 3 a compound or salt thereof of clause 1 or 2 is provided, wherein each $R^3$ is H.

In accordance with clause 4 a compound or salt thereof of any one of clauses 1-3 is provided, wherein $R^4$ is $C_6$-$C_{10}$ aryl, wherein each hydrogen atom is $C_6$-$C_{10}$ is optionally substituted with halogen, $C_1$-$C_6$ alkyl, or —$OC_1$-$C_6$ alkyl.

In accordance with clause 5 a compound or salt thereof of any one of the clauses 1-4 is provided, wherein $R^C$ is —$C_1$-$C_6$ alkyl-$C_3$-$C_8$ heterocycloalkyl, wherein each hydrogen atom in $C_1$-$C_6$ alkyl and $C_3$-$C_8$ heterocycloalkyl is optionally substituted with $C_1$-$C_6$ alkyl, oxo, $C_3$-$C_8$ heterocycloalkyl, or $R^E$, provided $R^C$ includes at least one $R^E$.

In accordance with clause 6 a compound or salt thereof of any one of the clauses 1-5 is provided, wherein $R^C$ is —$CH_2C(O)$—$C_3$-$C_8$ heterocycloalkyl-$R^E$ or —$CH(CH_3)C(O)$—$C_3$-$C_8$ heterocycloalkyl-$R^E$.

In accordance with clause 7 a compound or salt thereof of clause 1 is provided, wherein the compound is of the formula Ib

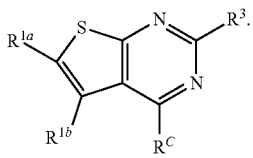

In accordance with clause 8 a compound or salt thereof of clause 1 or 7 is provided, wherein $R^3$ is $C_1$-$C_6$ alkyl, $C_3$-$C_6$ cycloalkyl, $C_6$-$C_{10}$ aryl, —$NH(R^A)$, or —$N(R^A)(R^B)$, wherein each hydrogen atom in $C_6$-$C_{10}$ aryl is optionally substituted by $R^D$, and wherein each hydrogen atom in $C_1$-$C_6$ alkyl and $C_3$-$C_6$ cycloalkyl is optionally substituted by $C_6$-$C_{10}$ aryl optionally substituted with at least one $R^D$.

In accordance with clause 9 a compound or salt thereof of any one of clauses 1, 7 or 8 is provided, wherein $R^3$ is $C_1$-$C_6$ alkyl wherein each hydrogen atom in $C_1$-$C_6$ alkyl is optionally substituted by $C_6$-$C_{10}$ aryl, optionally substituted with at least one $R^D$.

In accordance with clause 10 a compound or salt thereof of any one of clauses 1 or 7-9 is provided, wherein $R^3$ is $C_1$-$C_6$ alkyl substituted by $C_6$-$C_{10}$ aryl optionally substituted with halogen or O—$C_1$-$C_6$ alkyl.

In accordance with clause 11 a compound or salt thereof of any one of clauses 1 or 7-9 is provided, wherein $R^3$ is $C_1$-$C_6$ alkyl.

In accordance with clause 12 a compound or salt thereof of any one of clauses 1 or 7-8 is provided, wherein $R^3$ is $C_3$-$C_6$ cycloalkyl.

In accordance with clause 13 a compound or salt thereof of any one of clauses 1 or 7-12 is provided, wherein $R^C$ is $C_3$-$C_8$ heterocycloalkyl, wherein at least one hydrogen atom in $C_3$-$C_8$ heterocycloalkyl is substituted with $C_1$-$C_6$ alkyl, oxo, $C_3$-$C_8$ heterocycloalkyl, or $R^E$, provided $R^C$ includes at least one $R^E$.

In accordance with clause 14 a compound or salt thereof of any of clauses 1 or 7-13 is provided, wherein $R^C$ is $C_3$-$C_8$ heterocycloalkyl, wherein at least one hydrogen atom in $C_3$-$C_8$ heterocycloalkyl is substituted with $R^E$.

In accordance with clause 15 a compound or salt thereof of any one of clauses 14 is provided, wherein $R^{1a}$ and $R^{1b}$ combine to form a $C_3$-$C_8$ cycloalkyl.

In accordance with clause 16 a compound or salt thereof of any one of clauses 1-15 is provided, wherein $R^{1a}$ and $R^{1b}$ are H.

In accordance with clause 17 a compound or salt thereof of any one of clauses 1-16 is provided, wherein $R^E$ is —$C(O)C_1$-$C_6$ alkyl, —$C(O)C_2$-$C_6$ alkenyl, or —$C(O)C_2$-$C_6$ alkynyl, wherein each hydrogen atom in $C_1$-$C_6$ alkyl, $C_2$-$C_6$ alkenyl, and $C_2$-$C_6$ alkynyl, is optionally substituted with deuterium, halogen, or —$N(C_1$-$C_6$ alkyl$)_2$.

In accordance with clause 18 a compound or salt thereof of any one of clauses 1-17 is provided, wherein $R^E$ is

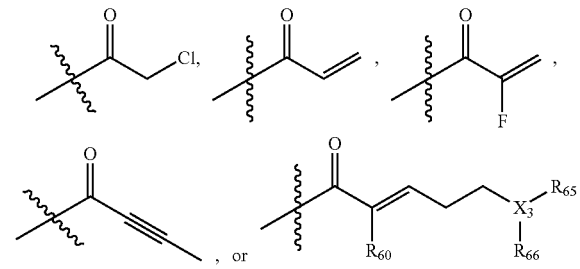

wherein $X_3$ is C or N, $R_{60}$ is H or F and $R_{65}$ and $R_{66}$ are methyl or together with the atoms to which they are attached form a 5 or 6 membered cycloalkyl or heterocycloalkyl ring, optionally wherein $R^E$ is

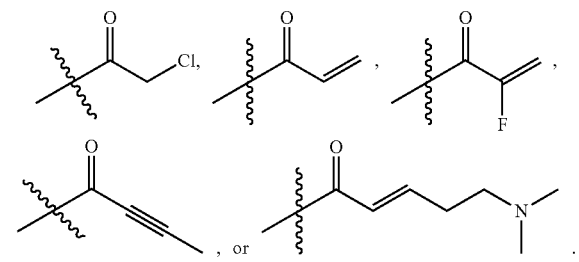

In accordance with clause 19, a compound is provided comprising a a compound that specifically binds to HPV E6 wherein the compound has the general structure of

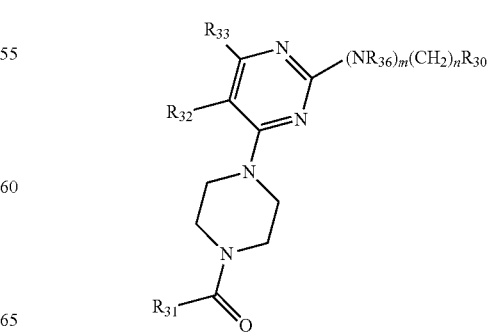

wherein

R$_{30}$ is selected from the group consisting of H, halo, cyclopropyl, and

[structure: phenyl with R$_{34}$ and R$_{35}$];

wherein R$_{34}$ is selected from the group consisting of H, —OCH$_3$, —OCF$_3$, F, —O— cyclopropyl and cyclopropyl;

R$_{35}$ is selected from the group consisting of H and —OCH$_3$;

n is an integer selected from 0-4;

m is 0 or 1;

R$_{31}$ is selected from the group consisting of —CH=CH$_2$, —CR$_{60}$=CH$_2$—CH=CHCH$_2$N(CH$_3$)$_2$, —CR$_{60}$=CH$_2$—N(CH$_3$)$_2$, —CH≡CHCH$_3$, CH$_2$(halo) and CH$_3$;

R$_{32}$ and R$_{33}$ together with the atoms to which they are bound form a cyclic or bicyclic ring fused to the existing ring of the general structure, wherein R$_{32}$ and R$_{33}$ together form a structure selected from the group consisting of

[structures: pyridine with X, Y; thiophene with R$_{38}$, R$_{39}$; benzothiophene with R$_{38}$; and cycloheptathiophene]

optionally wherein R$_{32}$ and R$_{33}$ together with the atoms to which they are bound form

[structures: dimethylthiophene; thiophene; tetrahydrobenzothiophene];

R$_{36}$ is selected from the group consisting of H and CH$_3$;

R$_{38}$ and R$_{39}$ are independently H, halo or CH$_3$; and

X and Y are independently N or C.

In accordance with clause 20 a compound or salt thereof of clause 19 is provided wherein R$_{30}$ is selected from the group consisting of H, halo, cyclopropyl and

[structure: phenyl with R$_{34}$]

wherein R$_{34}$ is H, halo or —OCH$_3$;

R$_{32}$ and R$_{33}$ together with the atoms to which they are bound form a cyclic or bicyclic ring selected from the group consisting of

[structures: thiophene; tetrahydrobenzothiophene; cycloheptathiophene];

n is an integer selected from 0-4;

m is 0 or 1;

R$_{36}$ is selected from the group consisting of H and CH$_3$;

optionally wherein m is 0;

n is an integer selected from 0-4; R$_{30}$ is H, and R$_{32}$ and R$_{33}$ together with the atoms to which they are bound form a cyclic or bicyclic ring selected from the group consisting of

[structures: thiophene; tetrahydrobenzothiophene; cycloheptathiophene];

or optionally wherein R$_{30}$ is

[structure: phenyl with R$_{34}$];

n is 1 or 2, m is 0 or 1 and R$_{34}$ is H, halo or —OCH$_3$ and R$_{32}$ and R$_{33}$ together with the atoms to which they are bound form a cyclic or bicyclic ring selected from the group consisting of

[structures: thiophene; tetrahydrobenzothiophene; cycloheptathiophene];

In accordance with clause 21 a compound is provided comprising a compound that specifically binds to HPV E6 wherein the compound has the general structure of

[structure: pyrimidine with R$_{33}$, R$_{32}$, NH linker, phenyl with R$_{34}$, piperazine with acryloyl group]

wherein $R_{32}$ and $R_{33}$ together with the atoms to which they are bound form a cyclic or bicyclic ring selected from the group consisting of

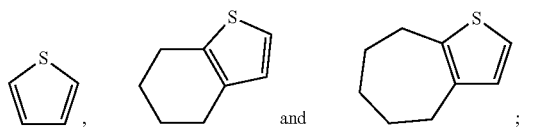 [SMILES: c1ccsc1 ; c1cc2c(s1)CCCC2 ; c1cc2c(s1)CCCCC2]

n is 1 or 2; and $R_{34}$ is H, halo or —OCH$_3$.

In accordance with clause 22 a compound is provided comprising a compound that specifically binds to HPV E6 wherein the compounds have the general structure of Formula II or IIIa

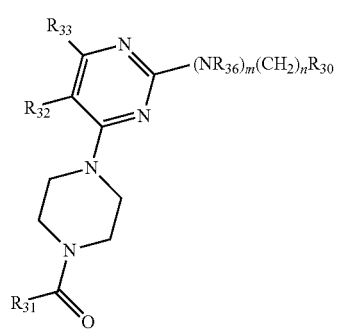

II or

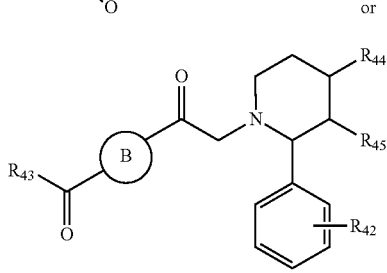

IIIa $R_{30}$ is selected from the group consisting of H, halo, cyclopropyl and

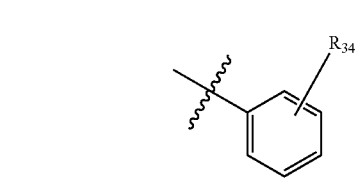

wherein $R_{34}$ is H, halo or —OCH$_3$;

$R_{32}$ and $R_{33}$ together with the atoms to which they are bound form a cyclic or bicyclic ring selected from the group consisting of

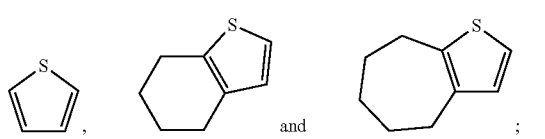

n is an integer selected from 0-4;

m is 0 or 1; and $R_{36}$ is selected from the group consisting of H and CH$_3$;

optionally wherein m is 0;

n is an integer selected from 0-4; $R_{30}$ is H, and $R_{32}$ and $R_{33}$ together with the atoms to which they are bound form a cyclic or bicyclic ring selected from the group consisting of

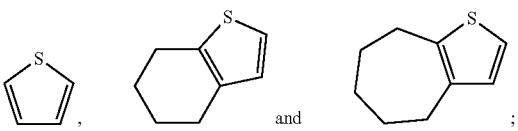

or optionally wherein $R_{30}$ is

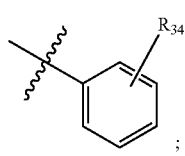

;

n is 1 or 2, m is 0 or 1 and $R_{34}$ is H, halo or —OCH$_3$ and $R_{32}$ and $R_{33}$ together with the atoms to which they are bound form a cyclic or bicyclic ring selected from the group consisting of

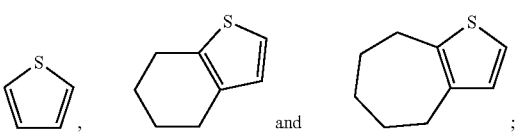 [SMILES: c1ccsc1 ; c1cc2c(s1)CCCC2 ; c1cc2c(s1)CCCCC2]

$R_{42}$ is selected from the group consisting of H, —OCH$_3$, —OCF$_3$, halo and CH$_3$;

$R_{43}$ is selected from the group consisting of —CH=CH$_2$, and CH$_2$(halo);

ring B is selected from the group consisting of

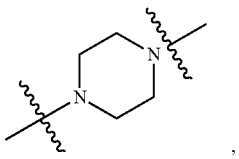

,

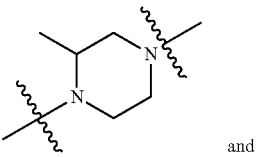

and

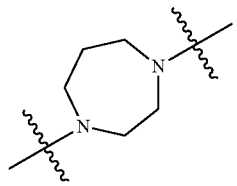

and $R_{44}$ and $R_{45}$ together with the atoms to which they are bound form a cyclic ring selected from the group consisting of

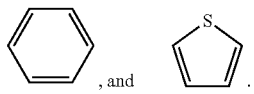

In accordance with clause 23 a compound is provided comprising a compound that specifically binds to HPV E6 and has the structure of Formula II:

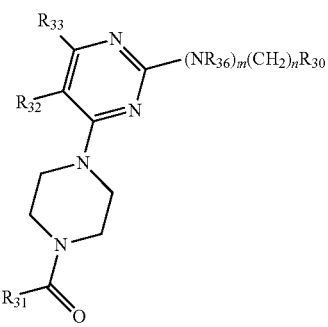

wherein $R_{30}$ is selected from the group consisting of H, halo, cyclopropyl, and

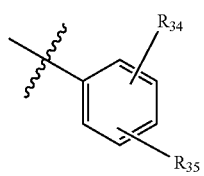

wherein $R_{34}$ is selected from the group consisting of H, —OCH$_3$, —OCF$_3$, and cyclopropyl;

$R_{35}$ is selected from the group consisting of H and —OCH$_3$;

n is an integer selected from 0-4;

m is 0 or 1;

$R_{31}$ is selected from the group consisting of —CH=CH$_2$, —CH=CHCH$_2$N(CH$_3$)$_2$, —CH≡CHCH$_3$, CH$_2$(halo) and CH$_3$;

$R_{32}$ and $R_{33}$ together with the atoms to which they are bound form a cyclic or bicyclic ring selected from the group consisting of

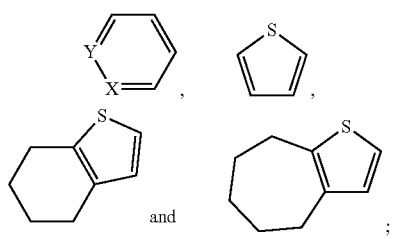

$R_{36}$ is selected from the group consisting of H and CH$_3$; X and Y are independently N or C.

In accordance with clause 24 a compound or salt thereof of any one of clauses 19-23 is provided that specifically binds to HPV E6 and has the structure of Formula II, further wherein $R_{30}$ is

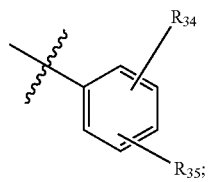

$R_{34}$ is selected from the group consisting of H, —OCH$_3$, and —OCF$_3$;

$R_{35}$ is H;

n is an integer selected from 0-4;

m is 0 or 1;

$R_{31}$ is selected from the group consisting of —CH=CH$_2$, CH$_2$(halo), —CH=CHCH$_2$N(CH$_3$)$_2$ and —CH≡CHCH$_3$;

$R_{32}$ and $R_{33}$ together with the atoms to which they are bound form a cyclic or bicyclic ring selected from the group consisting of

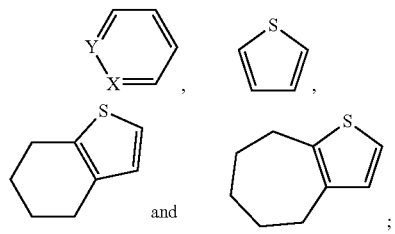

$R_{36}$ is selected from the group consisting of H and CH$_3$, and

X and Y are independently N or C.

In accordance with clause 25 a compound or salt thereof of any one of clauses 19-24 is provided wherein the compound that specifically binds to HPV E6 has the structure of

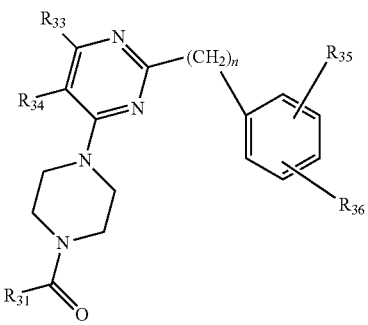

wherein $R_{33}$ and $R_{34}$ together with the atoms to which they are bound form a cyclic or bicyclic ring selected from the group consisting of

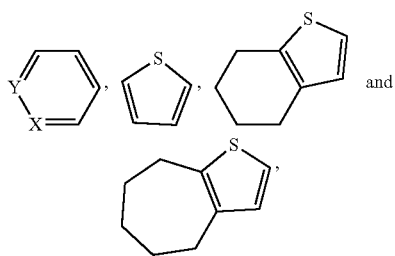 and

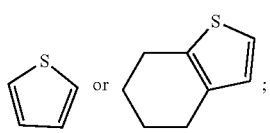, optionally wherein $R_{33}$ and $R_{34}$ together with the atoms to which they are bound form

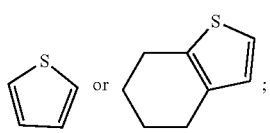 or 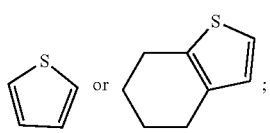;

n is an integer selected from 0-4;
X and Y are independently N or C;
$R_{34}$ is selected from the group consisting of H, —OCH$_3$, and —OCF$_3$;
$R_{35}$ is H; and
$R_{31}$ is selected from the group consisting of —CH=CH$_2$, CH$_2$(halo), —CH=CHCH$_2$N(CH$_3$)$_2$ and —CH≡CHCH$_3$.

In accordance with clause 26 a compound or salt thereof of any one of clauses 19-25 is provided wherein the compound that specifically binds to HPV E6 has the structure of

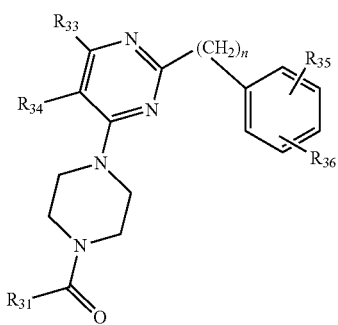

wherein
$R_{33}$ and $R_{34}$ together with the atoms to which they are bound form a cyclic or bicyclic ring selected from the group consisting of

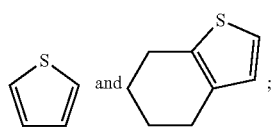;

n is an integer selected from 0-4;
$R_{34}$ is selected from the group consisting of H, —OCH$_3$, and —OCF$_3$;
$R_{35}$ is H; and
$R_{31}$ is selected from the group consisting of —CH=CH$_2$, CH$_2$(halo), —CH=CHCH$_2$N(CH$_3$)$_2$ and —CH≡CHCH$_3$.

In accordance with clause 27 a compound or salt thereof of any one of clauses 19-26 is provided wherein the compound that specifically binds to HPV E6 has the structure of

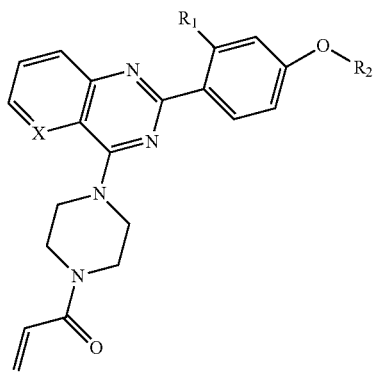

wherein
$R_1$ is H or F;
$R_2$ is —CH$_3$, —CF$_3$ or cyclopropyl; and
X is N or C.

In accordance with clause 28 a compound or salt thereof of clause 21 is provided wherein the compound that specifically binds to HPV E6 and has the structure of:

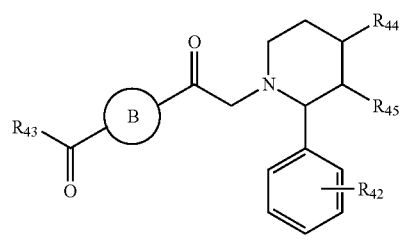

wherein
$R_{42}$ is selected from the group consisting of H, —OCH$_3$, —OCF$_3$, halo and CH$_3$;
$R_{43}$ is selected from the group consisting of —CH=CH$_2$, and CH$_2$(halo);
ring B is selected from the group consisting of

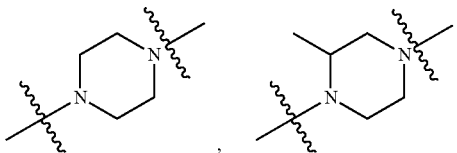,

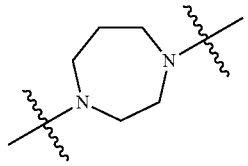 and and
$R_{44}$ and $R_{45}$ together with the atoms to which they are bound form a cyclic ring selected from the group consisting of

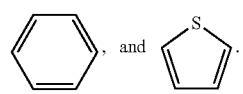.

In accordance with clause 29 a compound or salt thereof of claim 28 is provided wherein the compound that specifically binds to HPV E6 has the structure of

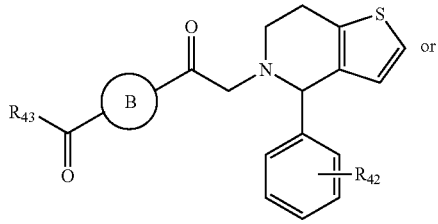

or

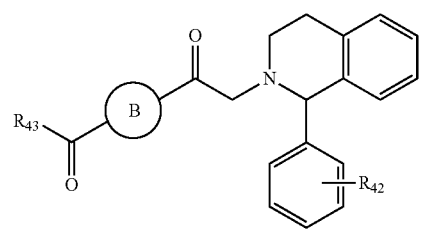

wherein $R_{42}$ is selected from the group consisting of H, —OCH$_3$, —OCF$_3$, halo and CH$_3$;

$R_{43}$ is selected from the group consisting of —CH=CH$_2$, and CH$_2$(halo), optionally wherein $R_{43}$ is —CH=CH$_2$; and ring B is selected from the group consisting of

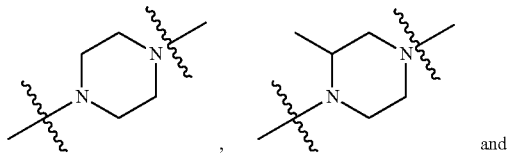

, and

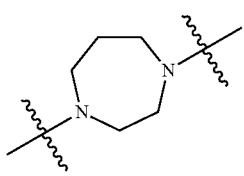

In accordance with clause 30 a compound or salt thereof of any one of clauses 28 or 29 is provided wherein the compound that specifically binds to HPV E6 has the structure of

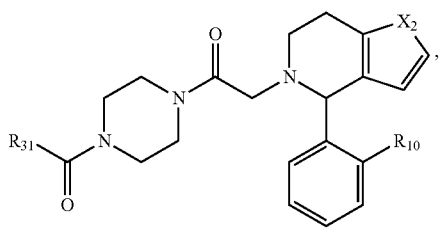

,

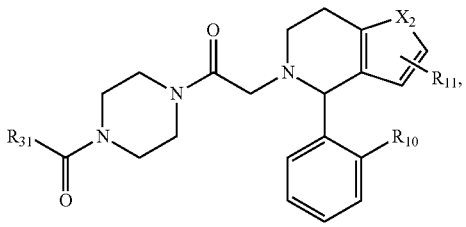

,

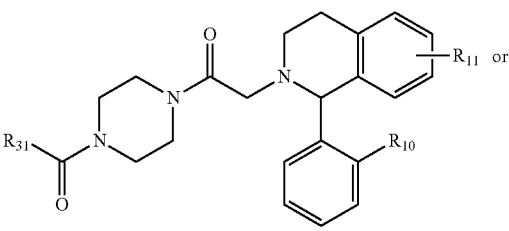

or

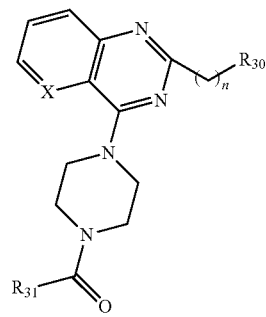

wherein $R_{10}$ is H, CH$_3$, CF$_3$, OCH$_3$, OCF$_3$, CN or halo;

$R_{11}$ is H or OCH$_3$;

$X_2$ is C, O or S, optionally wherein $X_2$ is S $R_{30}$ is selected from the group consisting of H, halo, cyclopropyl, and

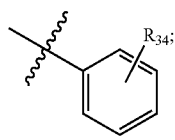

n is an integer selected from 1 to 4;

X is N or C;

$R_{31}$ is selected from the group consisting of —CH=CH$_2$, —CH=CHCH$_2$N(CH$_3$)$_2$, —CH≡CHCH$_3$, CH$_2$(halo) and CH$_3$, optionally wherein $R_{31}$ is —CH=CHCH$_2$N(CH$_3$)$_2$, —CH=CH$_2$, or —CH≡CHCH$_3$, optionally wherein $R_{31}$ is —CH=CH$_2$; and $R_{34}$ is selected from the group consisting of H, —OCH$_3$, —OCF$_3$, and cyclopropyl.

In accordance with clause 31 a compound or salt thereof of clause 30 is provided wherein said compound has the structure of

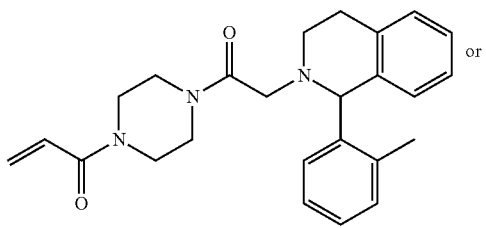

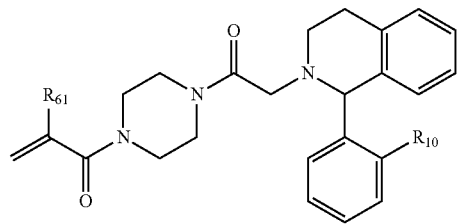

wherein R$_{61}$ is H or F; and R$_{10}$ is H, CH$_3$, CF$_3$, OCH$_3$, OCF$_3$, CN or halo, optionally wherein R$_{61}$ is H and R$_{10}$ is H, OCH$_3$ or CH$_3$;

In accordance with clause 32 a pharmaceutical composition is provided comprising a compound of any one of clauses 1-31, or a pharmaceutically acceptable salt thereof, and optionally at least one diluent, carrier or excipient.

In accordance with clause 33 a method of treating HPV is provided comprising administering to a subject in need of such treatment an effective amount of at least one compound of any one of clauses 1 to 29, or a pharmaceutically acceptable salt thereof.

In accordance with clause 34 a use of a compound of any one of clauses 1 to 31, or a pharmaceutically acceptable salt thereof, is provided in the preparation of a medicament for the treatment of HPV.

In accordance with clause 35 a compound of any one of clauses 1 to 31, or a pharmaceutically acceptable salt thereof, is provided for treating HPV.

In accordance with clause 36, a method of inhibiting HPV E6 is provided, comprising contacting a cell comprising HPV E6 with an effective amount of at least one compound of any one of clauses 1 to 31, or a pharmaceutically acceptable salt thereof, and/or with at least one pharmaceutical composition of the disclosure, wherein the contacting is in vitro, ex vivo, or in vivo.

In accordance with clause 37 a compound of any one of clauses 1 to 31 is provided, for use in treating HPV in a patient.

In accordance with clause 38, a method of treating HPV is provided comprising administering to a subject in need of such treatment an effective amount of at least one compound of the formula I

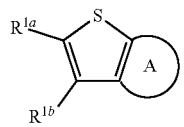

I wherein ring A is

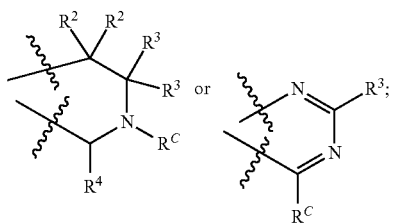

R$^{1a}$ and R$^{1b}$ are independently H, deuterium, or C$_1$-C$_6$ alkyl, or R$^{1a}$ and R$^{1b}$ together with the carbon atoms to which they are attached combine to form a C$_3$-C$_8$ cycloalkyl, wherein each hydrogen atom in C$_1$-C$_6$ alkyl and C$_3$-C$_8$ cycloalkyl is optionally substituted with R$^D$;

each R$^2$ is H;

each R$^3$ is independently H, deuterium, C$_1$-C$_6$ alkyl, C$_3$-C$_6$ cycloalkyl, C$_6$-C$_{10}$ aryl, —NH(R$^A$), or —N(R$^A$)(R$^B$), wherein each hydrogen atom in C$_6$-C$_{10}$ aryl is optionally substituted by R$^D$, and wherein each hydrogen atom in C$_1$-C$_6$ alkyl and C$_3$-C$_6$ cycloalkyl is optionally substituted by C$_6$-C$_{10}$ aryl optionally substituted with at least one R$^D$;

R$^4$ is C$_6$-C$_{10}$ aryl, wherein each hydrogen atom is C$_6$-C$_{10}$ is optionally substituted with R$^D$;

R$^A$ and R$^B$ are independently C$_1$-C$_6$ alkyl, wherein each hydrogen atom in C$_1$-C$_6$ alkyl is optionally substituted by C$_6$-C$_{10}$ aryl, wherein each hydrogen atom is C$_6$-C$_{10}$ aryl is optionally substituted with R$^D$;

R$^C$ is C$_1$-C$_6$ alkyl, C$_3$-C$_8$ heterocycloalkyl, or —C$_1$-C$_6$ alkyl-C$_3$-C$_8$ heterocycloalkyl, wherein each hydrogen atom in C$_1$-C$_6$ alkyl and C$_3$-C$_8$ heterocycloalkyl is optionally substituted with C$_1$-C$_6$ alkyl, oxo, C$_3$-C$_8$ heterocycloalkyl, or R$^E$, provided R$^C$ includes at least one R$^E$;

each R$^D$ is independently deuterium, halogen, C$_1$-C$_6$ alkyl, or —OC$_1$-C$_6$ alkyl, wherein each hydrogen atom in C$_1$-C$_6$ alkyl is optionally substituted with deuterium, halogen, or oxo;

R$^E$ is C$_1$-C$_6$ alkyl, C$_2$-C$_6$ alkenyl, or C$_3$-C$_6$ alkynyl, wherein each hydrogen atom in C$_1$-C$_6$ alkyl, C$_2$-C$_6$ alkenyl, and C$_3$-C$_6$ alkynyl is optionally substituted with halogen, oxo, or —N(C$_1$-C$_6$ alkyl)$_2$, provided at least one hydrogen atom in C$_1$-C$_6$ alkyl, C$_2$-C$_6$ alkenyl, and C$_3$-C$_6$ alkynyl is substituted with halogen, oxo, or —N(C$_1$-C$_6$ alkyl)$_2$;

or a pharmaceutically acceptable salt thereof.

In accordance with clause 39 a method of inhibiting HPV E6 activity is provided, comprising contacting a cell comprising HPV E6 with an effective amount of at least one compound of any one of those disclosed in clauses 1-31, or a pharmaceutically acceptable salt thereof.

In accordance with clause 40 a compound selected from Table 1, or a salt thereof, is provided, with the proviso that the compound is not EIN-116, EIN-117, EIN-118, EIN-119, EIN-120, EIN-121, EIN-123, EIN-124, EIN-125, EIN-126, EIN-127, EIN-128, EIN-129, EIN-130, or EIN-131, optionally for use in treating an HPV infection and/or inhibiting the activity of HPV E6.

In accordance with clause 40 a method of drug design is provided wherein the binding of a compound of any one of clauses 1-31, or a pharmaceutically acceptable salt thereof is used to form a bound structure with HPV E6 and the bound structure is used for drug design.

In accordance with clause 41 a method of clause 40 is provided, wherein the bound structure is analyzed using crystallography, nuclear magnetic resonance, or cryo-electron microscopy.

In accordance with clause 42 a composition is provided comprising the bound structure of clause 40.

EXAMPLES

Chemical Synthesis

Exemplary chemical entities useful in methods of the description will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

EIN-116(cat #V008-7329), EIN-117(cat #V008-7342), EIN-118(cat #V009-0689), EIN-119(cat #V009-0721), EIN-120(cat #V009-8145), EIN-121(cat #V013-5084), EIN-123 (cat #V009-3346), EIN-124(cat #V001-3096), EIN-125(cat #V001-3172), EIN-126(cat #V002-4119), EIN-127(cat #V002-4126), EIN-128(cat #V002-4718), EIN-129(cat #V012-2359), EIN-130(cat #V031-2694), and EIN-131(cat #V031-2717) were each purchased from ChemDiv.

The compounds described herein, for example in Table 1, can generally be made according to General Method A or General Method B with suitable modifications understood by those skilled in the art. For example, changes in starting materials or reagents in General Methods A or B understood by those in the art can lead to the different substituents or modifications in the final compound.

Abbreviations The examples described herein use materials, including but not limited to, those described by the following abbreviations known to those skilled in the art:

| | |
|---|---|
| MS | molecular sieves |
| TFA | trifluoroacetic acid |
| DCM | dichloromethane |
| HATU | hexafluorophosphate azabenzotriazole tetramethyl uronium |
| TEA | triethylamine |
| dppf | 1,1'-bis(diphenylphosphino)ferrocene |
| rt | room temperature |
| DCM | dichloromethane |
| EA | ethyl acetate |
| TEA | triethylamine |
| PE | petroleum ether |
| dppf | 1,1'-Bis(diphenylphosphino)ferrocene |
| RT | room temperature |
| DMSO | Dimethyl sulfoxide |

General Method A

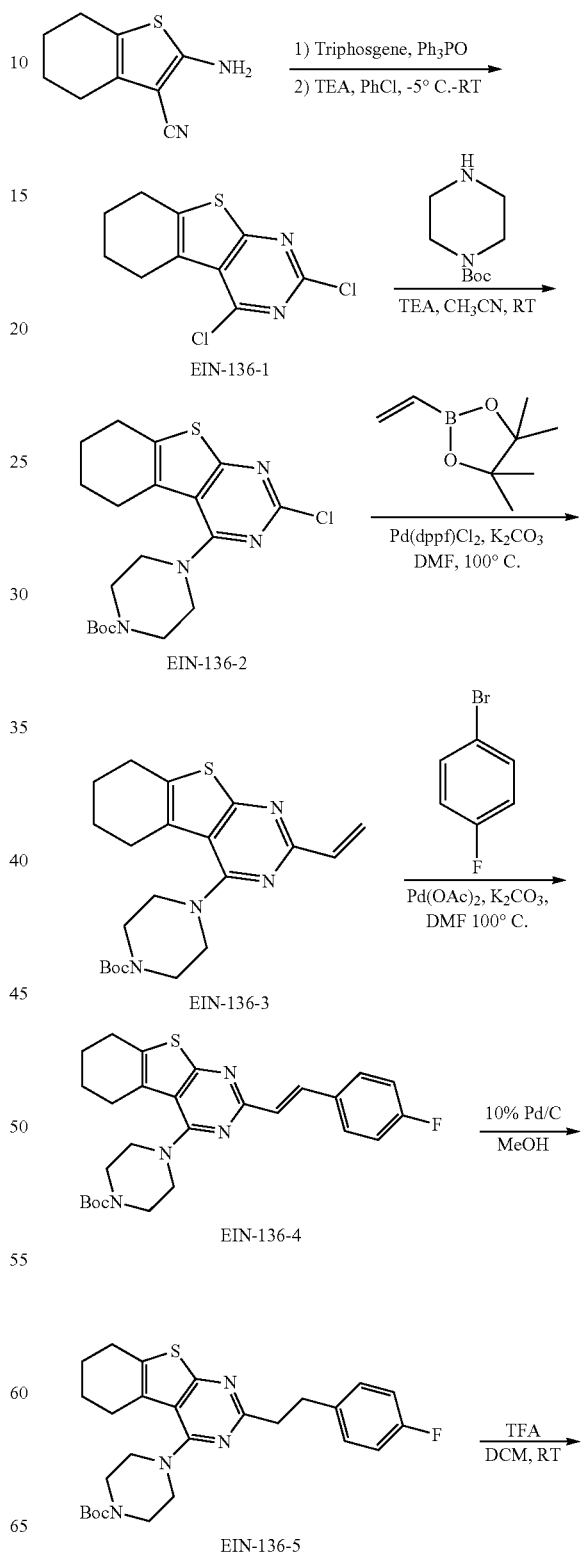

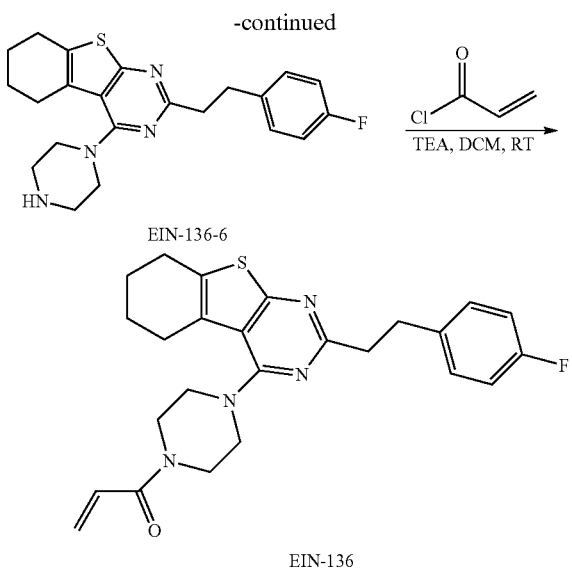

Step 1: 2,4-Dichloro-5,6,7,8-tetrahydrobenzo[4,5]thieno[2,3-d]pyrimidine (EIN-136-1)

To a solution of triphenylphosphine oxide (167 mg, 0.6 mmol, 0.2 eq) in chlorobenzene (5 mL) was added four drops of triethylamine at 0° C. Then, triphosgene (640 mg, 2.1 mmol, 0.7 eq) in chlorobenzene (5 mL) was added dropwise. After the mixture was stirred at RT for 0.5 h, 2-amino-4,5,6,7-tetrahydrobenzo[b]thiophene-3-carbonitrile (534 mg, 3 mmol, 1 eq) was added. The mixture was stirred at 120° C. for 6 h. NaHCO$_3$ was added to adjust to pH=7, and the mixture was reduced in volume and extracted with EA. The organic layer was washed with water, brine, and dried over anhydrous Na$_2$SO$_4$. The solvent was removed via reduced pressure, and the residue was purified with flash chromatography on silica gel (PE:EA=10:1-5:1) to give EIN-136-1 (343 mg, yield 44%). $^1$H NMR (400 MHz, CDCl$_3$): δ 3.07 (d, J=2.0 Hz, 2H), 2.88 (d, J=1.9 Hz, 2H), 2.02-1.79 (m, 4H). LCMS: m/z=259 [M+H]$^+$.

Step 2: Tert-Butyl 4-(2-chloro-5,6,7,8-tetrahydrobenzo[4,5]thieno[2,3-d]pyrimidin-4-yl)piperazine-1-carboxylate (EIN-136-2)

To a solution of EIN-136-1 (317 mg, 1.23 mmol, 1.0 eq) in CH$_3$CN (10 mL) was added triethylamine (124 mg, 1.23 mmol, 1.0 eq), and tert-butyl piperazine-1-carboxylate (229 mg, 1.23 mmol, 1.0 eq). The mixture was stirred at room temperature for 5 h, and then water was added and the mixture was extracted with EA. The organic layer was washed with water, brine, and dried over anhydrous Na$_2$SO$_4$. The mixture was filtered and the solvent was concentrated. The residue was purified with flash chromatography on silica gel (PE:EA=10:1-5:1) to give EIN-136-2 (420 mg, yield 84%). $^1$H NMR (400 MHz, CDCl$_3$): δ 3.66-3.51 (m, 4H), 3.48-3.32 (m, 4H), 2.86 (d, J=5.2 Hz, 4H), 1.93 (d, J=5.6 Hz, 2H), 1.81 (d, J=5.2 Hz, 2H), 1.48 (s, 9H). LCMS: m/z=409 [M+H]$^+$.

Step 3: Tert-Butyl 4-(2-vinyl-5,6,7,8-tetrahydrobenzo[4,5]thieno[2,3-d]pyrimidin-4-yl)piperazine-1-carboxylate (EIN-136-3)

To a solution of EIN-136-2 (300 mg, 0.74 mmol, 1.0 eq) and 4,4,5,5-tetramethyl-2-vinyl-1,3,2-dioxaborolane (342 mg, 2.22 mmol, 3 eq) in dioxane (15 mL) and water (3 mL) was added K$_2$CO$_3$ (204 mg, 1.48 mmol, 2.0 eq) and Pd(dppf)Cl$_2$ (54 mg, 0.08 mmol, 0.1 eq) under N$_2$ with stirring. The mixture was refluxed for 6 h until the solution became clear. The reaction mixture was cooled to room temperature. The solvent was removed by rotary evaporation. The residue was poured into water and extracted with EA. The organic layer was dried over Na$_2$SO$_4$, and filtered. The solvent was removed by rotary evaporation. The product was purified with flash chromatography on silica gel (PE:EA=10:1-5:1) to give EIN-136-3 (178 mg, yield 60%). $^1$H NMR (400 MHz, CDCl$_3$): δ 6.80 (dd, J=17.2, 10.4 Hz, 1H), 6.55 (dd, J=17.2, 1.9 Hz, 1H), 5.62 (dd, J=10.4, 1.9 Hz, 1H), 3.68-3.51 (m, 4H), 3.45-3.29 (m, 4H), 3.07-2.75 (m, 4H), 1.93 (dd, J=7.4, 3.8 Hz, 2H), 1.81 (dd, J=7.4, 3.6 Hz, 2H), 1.50 (d, J=6.3 Hz, 9H). LCMS: m/z=401 [M+H]+

Step 4: Tert-Butyl(E)-4-(2-(4-fluorostyryl)-5,6,7,8-tetrahydrobenzo[4,5]thieno[2,3-d]pyrimidin-4-yl)piperazine-1-carboxylate: (EIN-136-4)

To a solution of EIN-136-3 (120 mg, 0.3 mmol, 1.0 eq) and 1-bromo-4-fluorobenzene (263 mg, 1.5 mmol, 5 eq) in DMF (15 mL) was added K$_2$CO$_3$ (84 mg, 0.6 mmol, 2.0 eq) and Pd(OAc)$_2$ (36 mg, 0.15 mmol, 0.5 eq) under N$_2$ with stirring. The mixture was stirred at 100° C. for 6 h. The reaction mixture was cooled to room temperature. The mixture was poured into water and extracted with EA. The organic layer was dried over Na$_2$SO$_4$, filtered and the solvent was removed by rotary evaporation. The product was purified with flash chromatography on silica gel (PE:EA=10:1-5:1) to give EIN-136-4 (89 mg, yield 60%). $^1$H NMR (400 MHz, CDCl$_3$): δ 7.86 (d, J=15.9 Hz, 1H), 7.58 (dd, J=8.2, 5.6 Hz, 2H), 7.16-6.97 (m, 3H), 3.64 (s, 4H), 3.40 (s, 4H), 3.00-2.80 (m, 4H), 1.94 (d, J=5.1 Hz, 2H), 1.82 (d, J=4.1 Hz, 2H), 1.50 (s, 9H). LCMS: m/z=495 [M+H]$^+$.

Step 5: Tert-Butyl 4-(2-(4-Fluorophenethyl)-5,6,7,8-tetrahydrobenzo[4,5]thieno[2,3-d]pyrimidin-4-yl)piperazine-1-carboxylate: (EIN-136-5)

To a solution of EIN-136-4 (89 mg, 0.18 mmol, 1.0 eq) in MeOH (5 mL) was added 10% Pd/C (40 mg) under H$_2$ with stirring. The mixture was stirred for 1 h. The mixture was filtered, and concentrated to give the crude product EIN-136-5 (87 mg, yield 96%). $^1$H NMR (400 MHz, CDCl$_3$): δ 7.18 (dd, J=8.0, 5.7 Hz, 2H), 6.93 (t, J=8.6 Hz, 2H), 3.58 (s, 4H), 3.33 (s, 4H), 3.14 (d, J=1.7 Hz, 4H), 2.87 (dd, J=12.5, 5.8 Hz, 4H), 1.92 (d, J=4.1 Hz, 2H), 1.80 (d, J=3.9 Hz, 2H), 1.49 (s, 9H). LCMS: m/z=497 [M+H]$^+$.

Step 6: 2-(4-Fluorophenethyl)-4-(piperazin-1-yl)-5,6,7,8-tetrahydrobenzo[4,5]thieno[2,3-d]pyrimidine: (EIN-136-6)

To a solution of EIN-136-5 (87 mg, 0.17 mmol, 1.0 eq) in DCM (4 mL) was added TFA (1 mL). The mixture was stirred for 1 h at RT. The mixture was concentrated to give the crude product EIN-136-6 (crude). LCMS: m/z=397 [M+H]$^+$.

Step 7: 1-(4-(2-(4-Fluorophenethyl)-5,6,7,8-tetrahydrobenzo[4,5]thieno[2,3-d]pyrimidin-4-yl)piperazin-1-yl)prop-2-en-1-one: (EIN-136)

The crude product EIN-136-6 was dissolved in DCM (4 mL), and TEA was added to the solution until pH=8.0. Then, acryloyl chloride (16 mg, 0.17 mmol, 1.0 eq) in DCM (1.0 mL) was added dropwise to the solution. The reaction mixture was stirred at RT for 0.5 h, and poured into water. The mixture was extracted with DCM. The organic layer was dried over anhydrous Na$_2$SO$_4$, and the solution was filtered and concentrated. The residue was purified with column chromatography on silica gel (DCM/MeOH=50:1-20:1) to give the title product EIN-136 (30 mg, yield 40%). $^1$H NMR (400 MHz, CDCl$_3$): δ 7.18 (dd, J=8.2, 5.6 Hz, 2H), 6.93 (t, J=8.7 Hz, 2H), 6.61 (dd, J=16.8, 10.5 Hz, 1H), 6.33 (dd, J=16.8, 1.5 Hz, 1H), 5.74 (dd, J=10.6, 1.5 Hz, 1H), 3.82 (s, 2H), 3.71 (s, 2H), 3.40 (s, 4H), 3.25-3.05 (m, 4H), 2.88 (dd, J=10.9, 5.4 Hz, 4H), 2.01-1.87 (m, 2H), 1.89-1.76 (m, 2H). LCMS: m/z=463 [M+H]$^+$ General Method A

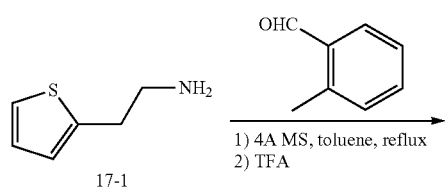

17-1

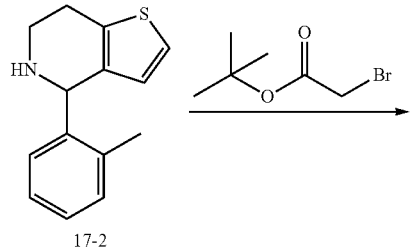

17-2

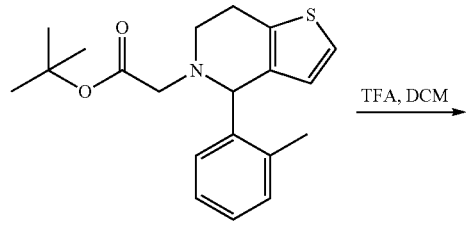

17-3

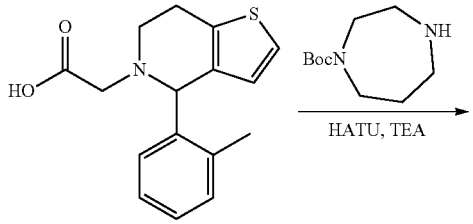

17-4

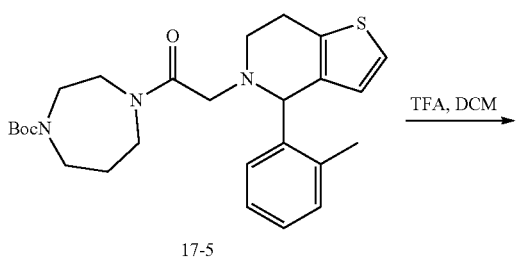

17-5

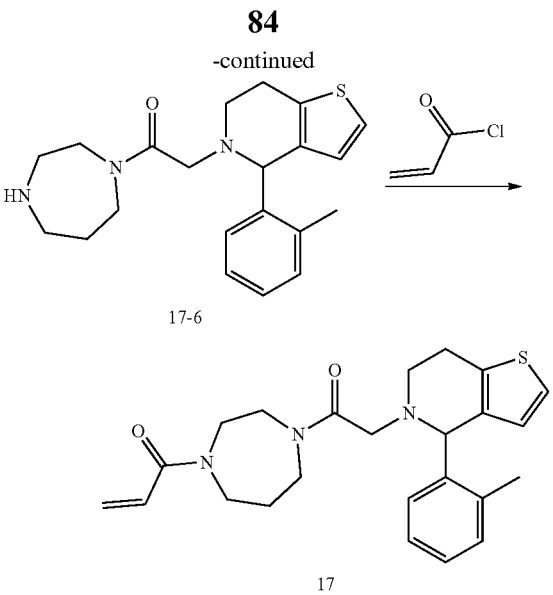

17-6

17

General Method B

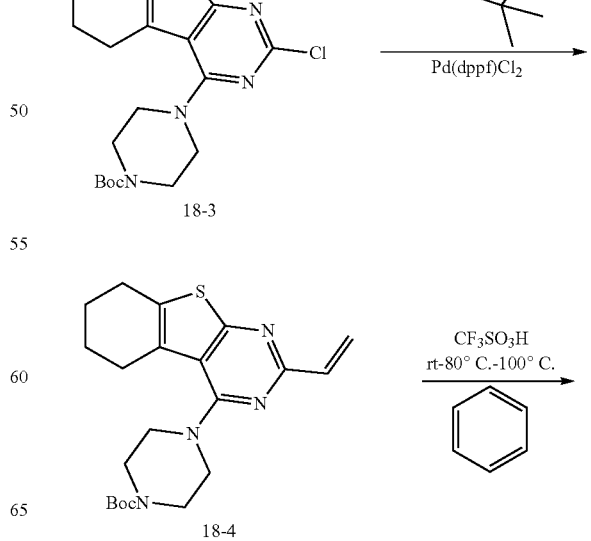

18-1

18-2

18-3

18-4

85
-continued
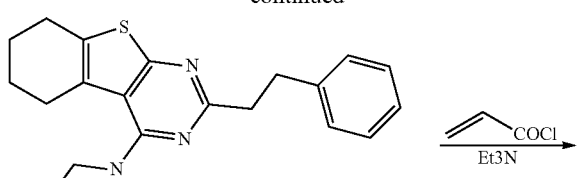
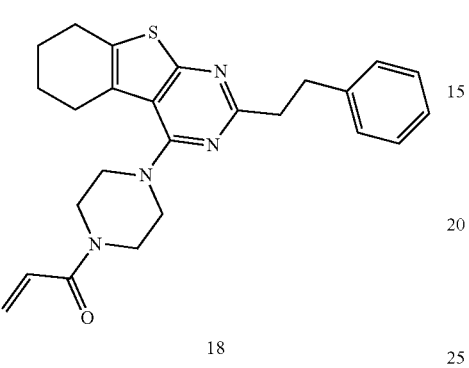
18
General Method B
1-(4-(2-(1-(o-tolyl)-3,4-dihydroisoquinolin-2(1H)-yl)acetyl)piperazin-1-yl)prop-2-en-1-one
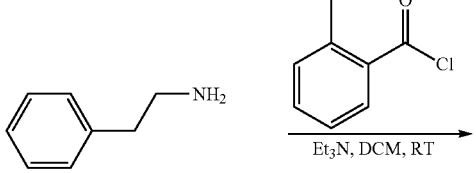
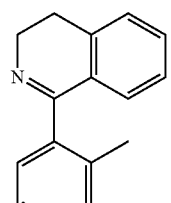
14-1
14-2
86
-continued
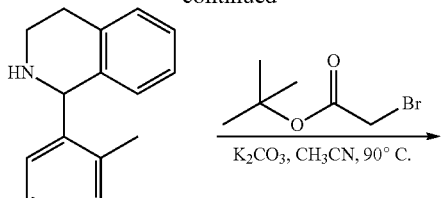
14-3
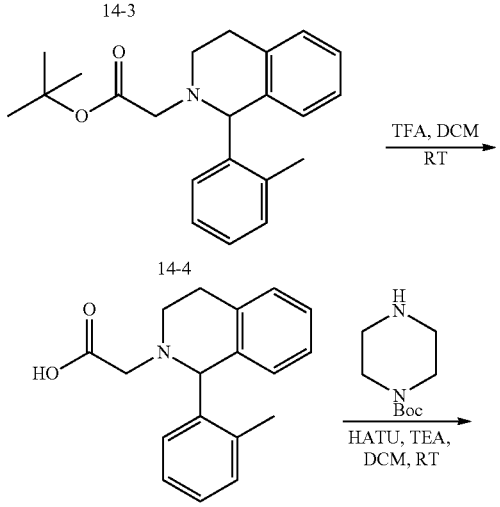
14-4
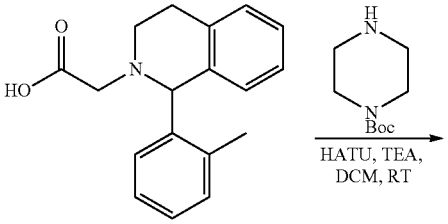
14-5
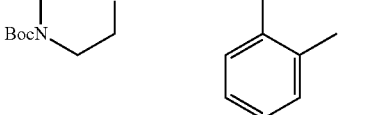
14-6
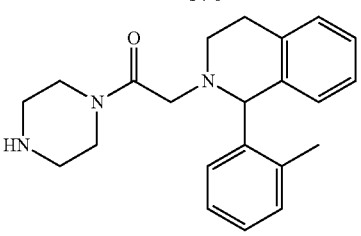
14-7
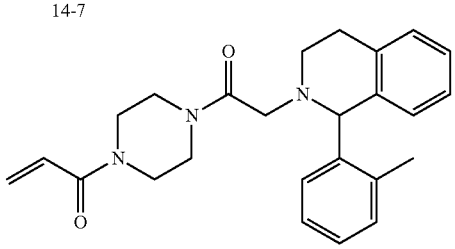
14
Step 1: 2-Methyl-N-phenethylbenzamide (14-1)
To a solution of 2-phenylethan-1-amine (3.63 g, 30 mmol, 1 eq) in DCM (100 mL) was added triethylamine (9.09 g, 90 mmol, 3 eq), and 2-methylbenzoyl chloride (5.12 g, 33 mmol, 1.1 eq) dropwise. The mixture was stirred at room temperature for 5 h, and then water was added and the mixture was extracted with EA. The organic layer was washed with water, brine, and dried over anhydrous $Na_2SO_4$. The mixture was filtered and the solvent was concentrated to give the crude product 14-1 (6.45 g, yield 90%).

LCMS: m/z=240 [M+H]$^+$.

Step 2: 1-(o-Tolyl)-3,4-dihydroisoquinoline (14-2)

The crude product 14-1 (6.45 g, yield 90%) was dissolved in PPA (10 mL) and was stirred at 150° C. overnight. Then the reaction was cooled to room temperature and was added the saturated $NaHCO_3$ solution to adjust pH to basic. The residue was poured into water and extracted with EA. The organic layer was dried over $Na_2SO_4$, and filtered. The solvent was removed by rotary evaporation. The crude product was purified with flash chromatography on silica gel (PE:EA=5:1-1:1) to give 1-(5.07 g, yield 85%).

$^1$H NMR (400 MHz, CDCl$_3$): δ 7.29 (ddt, J=20.4, 17.1, 7.7 Hz, 8H), 3.89 (s, 2H), 2.84 (t, J=7.4 Hz, 2H), 2.12 (s, 3H).

LCMS: m/z=222 [M+H]+

Step 3: 1-(o-Tolyl)-1,2,3,4-tetrahydroisoquinoline: (14-3)

To a solution of 14-2 (2.21 g, 10 mmol, 1.0 eq) in MeOH (40 mL) was added $NaBH_4$ (380 mg, 10 mmol, 1.0 eq). The mixture was stirred at RT for 3 h. The mixture was poured into water and extracted with EA. The organic layer was dried over $Na_2SO_4$, filtered and the solvent was concentrated to give the crude product 14-3 (2.12 g, yield 95%).

LCMS: m/z=224 [M+H]$^+$.

Step 4: Tert-Butyl 2-(1-(o-tolyl)-3,4-dihydroisoquinolin-2(1H)-yl)acetate: (14-4)

To a solution of 14-3 (1.12 g, 5 mmol, 1.0 eq) in $CH_3CN$ (100 mL) was added $K_2CO_3$ (2.07 g, 15 mmol, 3 eq). The mixture was stirred at 90° C. overnight. The mixture was filtered and the solvent was removed by rotary evaporation. The product was purified with flash chromatography on silica gel (PE:EA=10:1-5:1) to give 14-4 (1.6 g, yield 95%).

$^1$H NMR (400 MHz, CDCl$_3$): δ 7.25 (s, 1H), 7.21-7.01 (m, 5H), 6.95 (t, J=7.3 Hz, 1H), 6.57 (d, J=7.8 Hz, 1H), 5.14 (s, 1H), 3.32-3.13 (m, 3H), 3.15-2.96 (m, 2H), 2.78 (dd, J=16.7, 4.0 Hz, 1H), 2.26 (s, 3H), 1.43 (s, 9H).

LCMS: m/z=338 [M+H]$^+$.

Step 5 2-(1-(o-Tolyl)-3,4-dihydroisoquinolin-2(1H)-yl)acetic Acid: (14-5)

To a solution of 14-4 (337 mg, 1 mmol, 1 eq) in DCM (20 mL) was added TFA (8 mL). The mixture was stirred at RT for 3 h. The mixture was concentrated to give the crude product 14-5 (crude).

LCMS: m/z=282 [M+H]$^+$.

Step 6 Tert-Butyl 4-(2-(1-(o-tolyl)-3,4-dihydroisoquinolin-2(1H)-yl)acetyl)piperazine-1-carboxylate: (14-6)

The crude product 14-5 was dissolved in DCM (15 mL), and to the solution was added triethylamine (0.5 mL), tert-butyl piperazine-1-carboxylate (223 mg, 1.2 mmol, 1.2 eq) and HATU (456 mg, 1.2 mmol, 1.2 eq). The reaction mixture was stirred at RT for 1 h, and poured into water. The mixture was extracted with DCM. The organic layer was dried over anhydrous $Na_2SO_4$, and the solution was filtered and concentrated. The residue was purified with column chromatography on silica gel (PE:EA=5:1-1:1) to give the title product 14-6 (338 mg, yield 75%).

$^1$H NMR (400 MHz, CDCl$_3$): δ 7.24-7.03 (m, 6H), 7.04-6.85 (m, 1H), 6.55 (d, J=7.8 Hz, 1H), 4.66 (s, 1H), 3.86 (d, J=10.3 Hz, 1H), 3.58 (s, 1H), 3.44 (dd, J=16.2, 9.3 Hz, 3H), 3.32-3.00 (m, 5H), 3.01-2.62 (m, 4H), 2.23 (s, 3H), 1.46 (s, 9H).

LCMS: m/z=450 [M+H]$^+$.

Step 7 1-(Piperazin-1-yl)-2-(1-(o-tolyl)-3,4-dihydroisoquinolin-2(1H)-yl)ethan-1-one: (14-7)

To a solution of 14-6 (64 mg, 0.14 mmol, 1 eq) in DCM (4 mL) was added TFA (1 mL). The mixture was stirred at RT for 1 h. The mixture was concentrated to give the crude product 4-7 (crude).

LCMS: m/z=350 [M+H]$^+$.

Step 8 1-(4-(2-(1-(o-Tolyl)-3,4-dihydroisoquinolin-2(1H)-yl)acetyl)piperazin-1-yl)prop-2-en-1-one: (14)

The crude product 14-7 was dissolved in DCM (4 mL), and TEA was added to the solution until pH=8.0. Then, acryloyl chloride (13 mg, 0.14 mmol, 1.0 eq) in DCM (4.0 mL) was added dropwise to the solution. The reaction mixture was stirred at RT for 0.5 h, and poured into water. The mixture was extracted with DCM. The organic layer was dried over anhydrous $Na_2SO_4$, and the solution was filtered and concentrated. The residue was purified with column chromatography on silica gel (PE:EA=5:1-1:1) to give the title product 14 (25 mg, yield 45%).

$^1$H NMR (400 MHz, CDCl$_3$): δ 7.25-7.06 (m, 6H), 7.00 (d, J=7.5 Hz, 1H), 6.52 (dd, J=30.1, 10.6 Hz, 2H), 6.30 (d, J=16.7 Hz, 1H), 5.73 (d, J=10.5 Hz, 1H), 4.68 (s, 1H), 3.90 (d, J=13.4 Hz, 1H), 3.77 (s, 1H), 3.65 (d, J=23.1 Hz, 1H), 3.49 (d, J=13.0 Hz, 3H), 3.20 (dd, J=26.8, 13.6 Hz, 5H), 2.98 (dd, J=20.8, 11.4 Hz, 2H), 2.81 (dt, J=23.1, 11.0 Hz, 2H), 2.24 (s, 3H).

LCMS: m/z=404 [M+H]$^+$.

In Vitro Assays

Compounds were screened in a modified competitive E6AP binding assay. Briefly, maltose binding protein (MBP) HPV-16 E6 fusion is purified from *E. coli* and captured on amylose beads and incubated in buffer that includes 0.1% milk. For comparison, MBP-E6 with cysteine 51 replaced with serine (Cys51Ser) fusion protein is expressed and tested side by side. Test compounds are added and incubated for 16 hours at 4° C. and then washed out. The washed MBP-E6 protein bound beads are incubated with FLAG-tagged E6AP peptide fused to bacterial alkaline phosphatase (BAP). After extensive washing, the captured BAP activity is measured. In this format, E6AP is not directly exposed to free test compound. In addition, specificity was evaluated in counter screens at the same concentrations using FLAG antibody beads to collect the FLAG-E6AP-BAP, which should not be inhibited by compounds. These experiments showed several compounds inhibited E6AP binding to WT MBP-E6 and less inhibition with the E6 Cys51Ser mutant protein (Table 2).

Figure 1B:
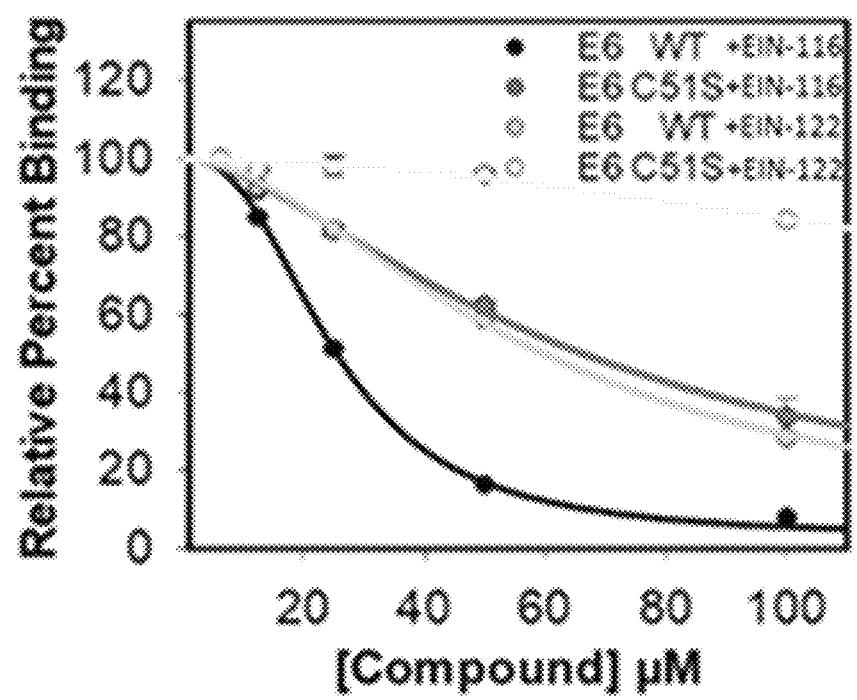
FIG. 1B is a depiction of Biolayer Interferometry binding data for the interaction between captured E6AP and 2 μM E6 WT or C51S in which the wild-type (WT) cysteine 51 was mutated to serine in the HPV-16 E6 encoded protein (see FIG. 7), incubated with varying concentrations of EIN-116 or EIN-122 for 16 hr at 4° C.
Figure 2A:
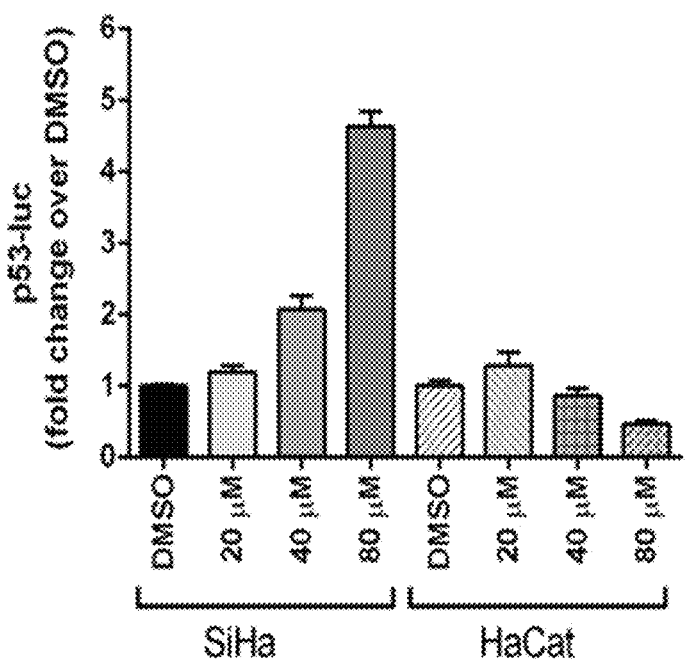
FIG. 2A depicts p53-luciferase (p53-Luc) activity in cell lysates from the SiHa and HaCat reporter cells after drug exposure with EIN-132 at the indicated concentrations for 48 hrs.
Figure 2B:
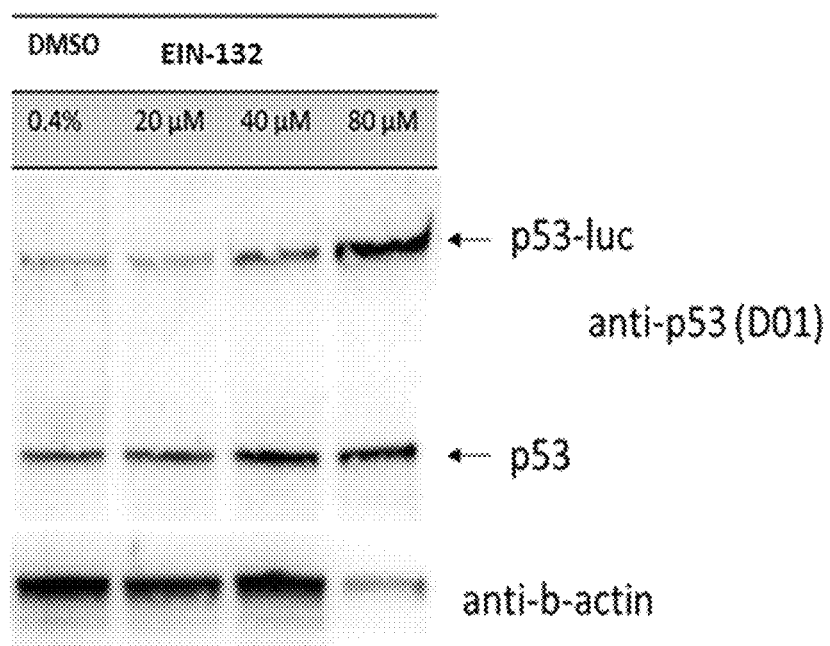
FIG. 2B depicts p53-luc and endogenous p53 protein levels in HPV-16 expressing human cervical cancer derived SiHa p53-Luc reporter cells treated with the indicated doses of EIN-132 for 48 hrs. Proteins were separated and detected by Western blotting with p53 and actin antibodies.
Figure 3:
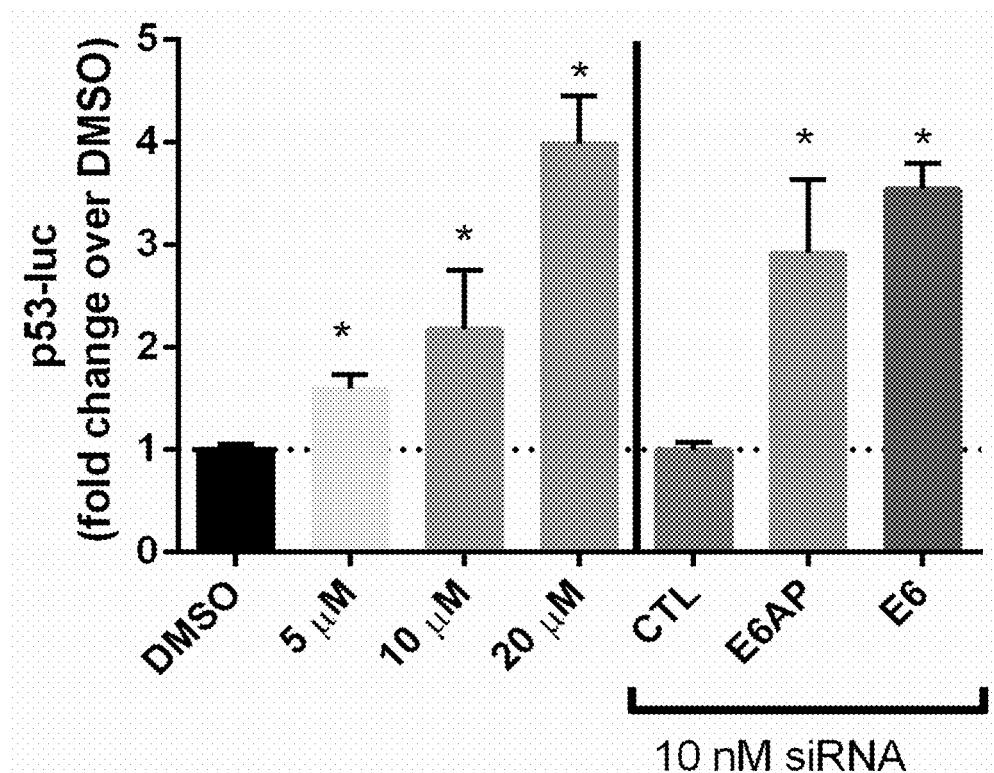
FIG. 3 depicts SiHa p53-Luc cells treated with DMSO or EIN-166 for 48 hrs. Right: Cells transfected with 10 nM siRNA each consisting of: scrambled negative control, directed against E6AP, or against HPV-16 E6. p53-Luc activity was normalized to DMSO or siRNA control. Data expressed as S.E.M *P<0.05 (n=3). Data expressed as S.E.M and *P<0.0.5 (n=3).
Figure 4:
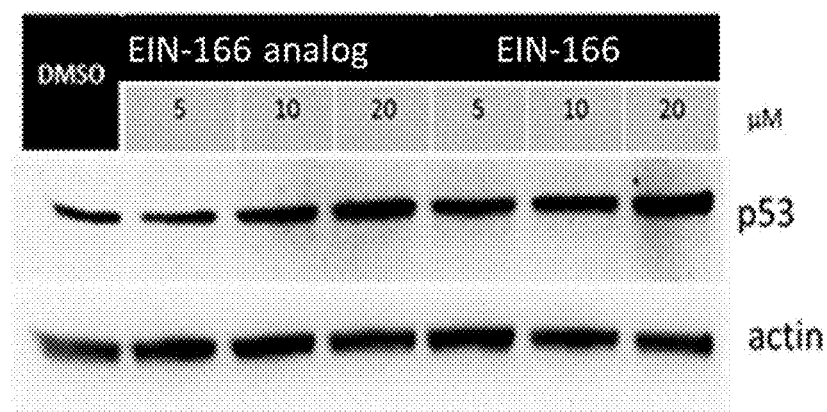
FIG. 4 depicts endogenous p53 protein levels in SiHa cells treated with the indicated concentrations of EIN-166 or one of its analogs for 48 hrs. Proteins were separated and detected by Western blotting with p53 and actin antibodies.
Figure 5A:
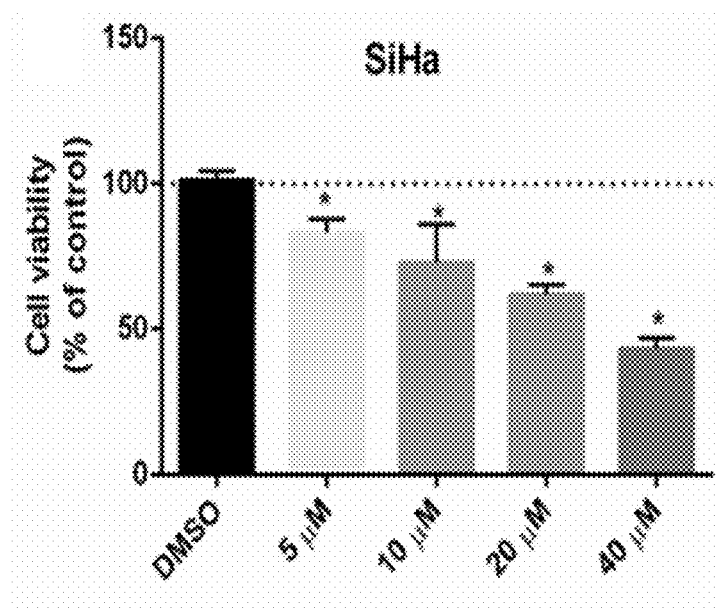
FIG. 5A depicts cell viability of SiHa cells after exposure to the indicated concentrations of EIN-166 for 48 hrs. Treatments were normalized to DMSO. Data expressed as S.E.M and *P<0.05 (n=4).
Figure 5B:
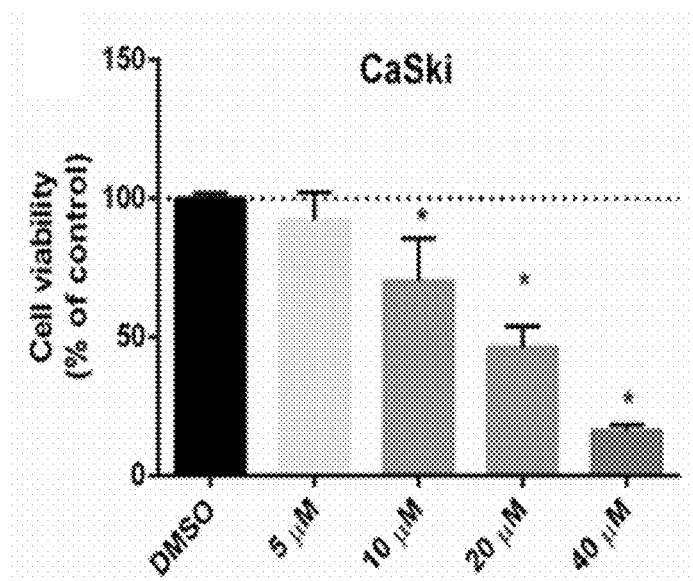
FIG. 5B depicts cell viability of CaSki cells after exposure to the indicated concentrations of EIN-166 for 48 hrs. Treatments were normalized to DMSO. Data expressed as S.E.M and *P<0.05 (n=4).
Figure 5C:
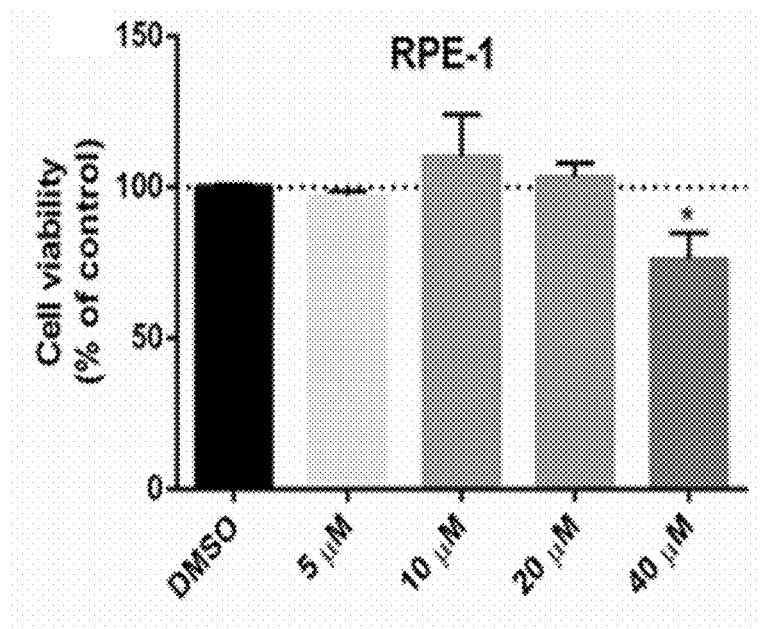
FIG. 5C depicts cell viability of RPE-1 cells (no HPV) after exposure to the indicated concentrations of EIN-166 for 48 hrs. Treatments were normalized to DMSO. Data expressed as S.E.M and *P<0.05 (n=4).
Figure 6:
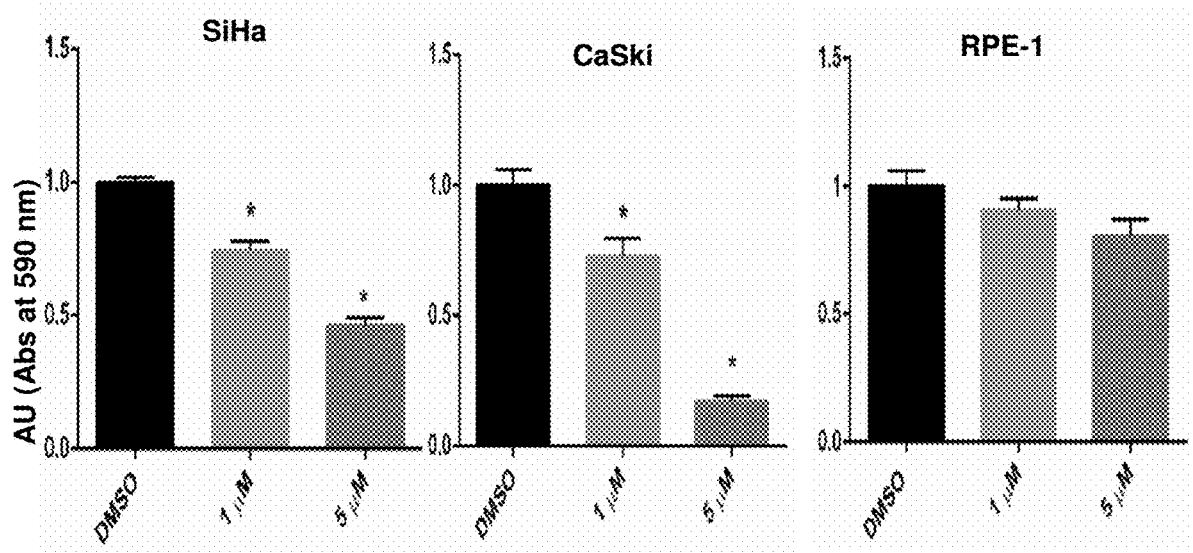
FIG. 6 depicts colony formation capabilities of SiHa, CaSki or RPE-1 cells in the presence of the indicated concentrations of EIN-166. Fifty cells were seeded and incubated with DMSO or EIN-166. After 14 days, cells were fixed and stained with crystal violet. Stained colonies were dissolved and absorbance at 590 nm was measured. Treatments were normalized to DMSO. Data expressed as S.E.M and *P<0.05 (n=3). RPE-1—no significant changes.

These hits were then studied by whole protein mass spectrometry. EIN-116 formed an adduct with wild-type E6 (FIG. 1A top) but not with E6 Cys51Ser mutant (FIG. 1A bottom). To determine if the compound inhibited E6 binding to E6AP, biolayer interferometry (BLI) was used. E6AP protein was captured on a sensor, and dipped into wells containing E6 WT with increasing concentration of EIN-116. The results showed that EIN-116 inhibited E6 binding to E6AP in a concentration-dependent manner. EIN-116 partly and EIN-122 nearly completely lost their ability to inhibit mutant form E6-Cys51Ser in which cysteine 51 was mutated to serine in the HPV-16 E6 encoded protein, consistent with covalent bond formation at Cys51 (FIG. 1B).

Table 2 summarizes the inhibitory activities of compounds screened with the E6/E6AP binding assay in columns 2 and 3. Amylose bound MBP-16E6 protein is incubated with compounds on filter plates. Solutions containing compounds are then removed by vacuum filtration and E6AP-BAP protein is added and incubated for 2 hours. Unbound E6AP is removed by vacuum filtrations and plates are washed prior to measuring of BAP activity. Compounds were screened at 10 and 100 µM with WT and C51S 16E6 protein. Inhibition of E6 to E6AP is expressed at the percentage of remaining BAP activity over DMSO control treated. In column 4 the inhibitory activities (IC50) of compounds screened with the BLI-assay are summarized. Biotin-labeled E6AP protein that was captured onto Super Streptavidin (SSA) biolayer interferometry (BLI) sensors (ForteBio, Cat #18-5057) were dipped into solutions containing 2 µM E6 WT or E6 C51S, which were pre-incubated with varying concentrations of compound. Allowing the determination of IC50 (µM) and maximal Inhibition (%). In column 5 the IC50s of compounds screened with the Fluoresence Polarization (FP) assay are summarized. The assay procedure is summarized as follows: varying concentrations of each MBP-E6 protein was tested for binding to fluorescently labeled pep11 peptide (TMR-KEKEEYNSNCSCI-ACIGLI; SEQ ID NO: 2). MBP-E6 (5 nM-2.5 µM) in assay buffer (400 mM NaCl, 50 mM Tris pH 6.8) was dispensed into a 384-well black polystyrene plate (Nunc, Roskilde, Denmark) and 625 nM pep11 in assay buffer was added. The fluorescence polarization was measured on a Neo2 plate reader (Biotek, Winooski, Vt.) using a filter set with excitation and emission wavelengths of 530 nm and 590 nm, respectively. Final concentration of MBP-E6 was used for all further experiments as it provided the highest assay window while staying in the linear portion of the binding profile.

Biologic Assays

The cervical cancer derived SiHa cell reporter line, which constitutively expresses HPV-16 E6 and E7, was created. SiHa cells with this p53-RLuc fusion gene have low basal levels of luciferase due to E6•E6AP-mediated degradation. HaCat, a human keratinocyte cell line stably expressing stably expressing p53 luciferase are used to assess off-target effects. SiHa-p53-Luc reporter cells, HaCat cells or SiHa cells are incubated with DMSO (0.1-0.4%) or increasing concentration of compound for 48 hours. Cells are lysed, luciferase activity is measured (Promega E2920) and p53 protein levels are determined via western blot.

Cell viability (metabolic activity) is measured by MTT assay after 48 hours of drug exposure. The HPV-16 expressing cervical cancer cell lines SiHa and CaSki and the HPV-negative epithelial RPE-1 cell line are used. Cells are incubated with DMSO (0.1-0.2%) or increasing concentration of compound for 48 hours.

TABLE 2

In vitro E6/E6AP Binding assay with WT 16E6 and C51S 16E6 protein at 10 and 100 µM (columns 2 and 3). In vitro BLI binding assay and FP measuring 16E6 WT and C51S binding to E6AP or E6AP peptide, respectively (columns 4 and 5).

| Reference | % Inhibition @10 µM | | % Inhibition @100 µM | | BLI IC50 at 24 h (µM) | | FP IC50 at 24 h (µM) | |
|---|---|---|---|---|---|---|---|---|
| | E6 WT/ E6AP | E6C51S/ E6AP | E6 WT/ E6AP | E6C51S/ E6AP | E6 WT/ E6AP | E6C51S/ E6AP | E6 WT/ E6AP | E6C51S/ E6AP |
| EIN-116 | 29 ± 8 | 5 ± 5 | 74 ± 3 | 36 ± 11 | 24.3 ± 1.1 (max 100%) | 61.9 ± 3.2 (max 100%) | | |
| EIN-117 | 17 ± 1 | | 33 ± 7 | | | | | |
| EIN-118 | 49 ± 5 | 12 ± 11 | 98 ± 2 | 79 ± 5 | | | | |
| EIN-119 | 33 ± 6 | 9 ± 7 | 61 ± 1 | 34 ± 7 | | | | |
| EIN-120 | 18 ± 5 | 12 ± 5 | 63 ± 1 | 34 ± 2 | | | | |
| EIN-121 | 24 ± 2 | | 52 ± 1 | | | | | |
| EIN-122 | 0 | | 97 ± 1 | | 62.7 ± 12.1 (max 100%) | NI | | |
| EIN-123 | 58 ± 12 | 44 ± 10 | 114 ± 11 | 90 ± 6 | | | | |
| EIN-124 | 71 ± 13 | 49 ± 11 | 113 ± 13 | 90 ± 5 | | | | |
| EIN-125 | 54 ± 13 | 32 ± 11 | 102 ± 10 | 62 ± 1 | 16.7 ± 0.6 (max 100%) | 35.3 ± 2.1 (max 100%) | | |
| EIN-126 | 18 ± 5 | 12 ± 5 | 63 ± 1 | 34 ± 2 | | | | |
| EIN-127 | 57 ± 14 | 41 ± 5 | 106 ± 11 | 79 ± 4 | | | | |
| EIN-128 | 47 ± 14 | 19 ± 8 | 106 ± 11 | 60 ± 3 | | | | |
| EIN-129 | 81 ± 16 | 57 ± 12 | 119 ± 13 | 103 ± 5 | | | | |
| EIN-130 | 46 ± 9 | 52 ± 12 | 100 ± 9 | 85 ± 6 | | | | |
| EIN-131 | 24 ± 3 | | 65 ± 3 | | | | | |
| EIN-132 | 3.5 ± 2 | 0 | 61 ± 2 | 19 ± 5 | 19.5 ± 1.2 (max 100%) | 51.4 ± 4.1 (max 100%) | | |
| EIN-133 | 26 ± 7 | 0 | 41 ± 5 | 0 | 14.9 ± 6.6 (max 60%) | NI | 10.4 ± 0.7 (max 9%) | NI |

TABLE 2-continued

In vitro E6/E6AP Binding assay with WT 16E6 and C51S 16E6 protein at 10 and 100 µM (columns 2 and 3). In vitro BLI binding assay and FP measuring 16E6 WT and C51S binding to E6AP or E6AP peptide, respectively (columns 4 and 5).

| Reference | % Inhibition @10 µM | | % Inhibition @100 µM | | BLI IC50 at 24 h (µM) | | FP IC50 at 24 h (µM) | |
|---|---|---|---|---|---|---|---|---|
| | E6 WT/E6AP | E6C51S/E6AP | E6 WT/E6AP | E6C51S/E6AP | E6 WT/E6AP | E6C51S/E6AP | E6 WT/E6AP | E6C51S/E6AP |
| EIN-134 | 18 ± 6 | 0 | 35 ± 4 | 0 | 32.6 ± 19.2 (max 100%) | NI | 12.1 ± 0.7 (max 11%) | NI |
| EIN-135 | 0 | 12 ± 3 | 52 ± 5 | 25 ± 4 | 10.9 ± 3.4 (max 85%) | NI | 15.4 ± 0.4 (max 27%) | NI |
| EIN-136 | 41 ± 7 | 0 | 69 ± 2 | 0 | 2.7 ± 0.3 (max 100%) | NI | 12.0 ± 0.9 (max 55%) | NI |
| EIN-137 | 35 ± 4 | 15 ± 3 | 56 ± 4 | 16 ± 5 | 4.9 ± 0.6 (max 90%) | NI | | |
| EIN-138 | 20 ± 6 | 16 ± 6 | 57 ± 3 | 19 ± 7 | 4.1 ± 0.5 (max 90%) | NI | | |
| EIN-139 | 13 ± 7 | 0 | 21 ± 4 | 6 ± 3 | NI | NI | 33.1 ± 1.3 (max 8%) | NI |
| EIN-140 | 6 ± 6 | 0 | 17 ± 4 | 0 | NI | NI | | |
| EIN-141 | 0 | 0 | 18 ± 5 | 0 | NI | NI | | |
| EIN-142 | 17 ± 4 | 0 | 28 ± 3 | 0 | NI | NI | | |
| EIN-143 | 44 ± 9 | 19 ± 7 | 78 ± 3 | 23 ± 10 | 2.5 ± 0.5 (max 100%) | NI | 7.1 ± 0.5 (max 93%) | NI |
| EIN-144 | 12 ± 6 | 9 ± 9 | 45 ± 4 | 17 ± 5 | 1.6 ± 0.5 (max 62%) | NI | 14.8 ± 1.2 (max 63%) | NI |
| EIN-145 | 32 ± 4 | 20 ± 6 | 51 ± 2 | 23 ± 7 | 2.0 ± 0.9 (max 65%) | NI | 15.0 ± 1.2 (max 59%) | NI |
| EIN-146 | 16 ± 4 | 11 ± 7 | 30 ± 3 | 15 ± 8 | 37 (max 100%) | 34.9 (max 100%) | 15.0 ± 0.5 (max 20%) | NI |
| EIN-147 | | | | | 31.9 (max 100%) | 25.4 (max 100%) | NI | NI |
| EIN-148 | | | | | 3.3 ± 0.3 (max 100%) | NI | 20.4 ± 3.0 (max 100%) | NI |
| EIN-149 | | | | | | | | |
| EIN-150 | | | | | 11.3 (max 100%) | 70.8 (max 100%) | 10.1 ± 1.1 (max 57%) | NI |
| EIN-151 | | | | | ND | ND | 24.5 ± 3.0 (max 71%) | NI |
| EIN-152 | | | | | 2.5 (max 100%) | 6.3 (max 60%) | 8.0 ± 2.3 (max 98%) | 229 ± 153 (max 100%) |
| EIN-153 | | | | | | | 27.7 ± 1.3 (max 100%) | |
| EIN-154 | | | | | 2.4 (max 100%) | 5.9 (max 75%) | 7.9 ± 0.8 (max 93%) | NI |
| EIN-155 | | | | | 8.7 ± 1.4 (max 100%) | 223 ± 210 (max 100%) | 32.8 ± 5.2 (max 100%) | NI |
| EIN-156 | | | | | 13.5 ± 1.3 (max 100%) | 133 ± 139 (max 100%) | | |
| EIN-157 | | | | | 16.0 ± 1.6 (max 100%) | 206 ± 197 (max 100%) | | |
| EIN-158 | | | | | | | 52.8 ± 2.8 (max 100%) | |
| EIN-159 | | | | | | | 14.5 ± 1.3 (max 91%) | NI |

TABLE 2-continued

In vitro E6/E6AP Binding assay with WT 16E6 and C51S 16E6 protein at 10 and 100 μM (columns 2 and 3). In vitro BLI binding assay and FP measuring 16E6 WT and C51S binding to E6AP or E6AP peptide, respectively (columns 4 and 5).

| Reference | % Inhibition @10 μM | | % Inhibition @100 μM | | BLI IC50 at 24 h (μM) | | FP IC50 at 24 h (μM) | |
|---|---|---|---|---|---|---|---|---|
| | E6 WT/ E6AP | E6C51S/ E6AP | E6 WT/ E6AP | E6C51S/ E6AP | E6 WT/ E6AP | E6C51S/ E6AP | E6 WT/ E6AP | E6C51S/ E6AP |
| EIN-160 | | | | | | | 128 ± 2.3 (max 100%) | NI |
| EIN-161 | | | | | | | 13.3 ± 1.9 (max 91%) | NI |
| EIN-162 | | | | | | | 105 ± 13.7 (max 100%) | NI |
| EIN-163 | | | | | | | 41.6 ± 2.8 (max 100%) | NI |
| EIN-164 | | | | | | | 22.9 ± 1.3 (max 100%) | NI |
| EIN-165 | | | | | | | 38.2 ± 2.1 (max 100%) | NI |
| EIN-166 | | | | | | | 73.4 ± 3.7 (max 100%) | NI |

NI: No Inhibition

---

The invention claimed is:

1. A compound that covalently attaches to an HPV E6 protein within an alpha helix binding pocket in the HPV E6 protein, thereby preventing binding of another protein in said binding pocket, wherein said compound has the structure of:

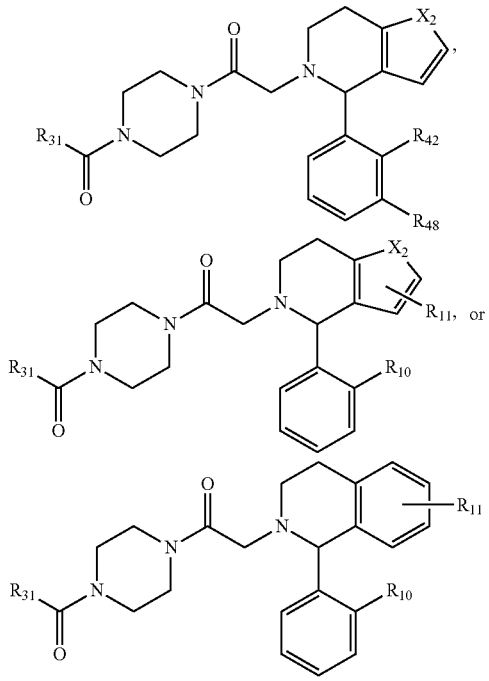

wherein
- $X_2$ is N, S or C;
- $R_{10}$ is H, $CH_3$, $CF_3$, $OCH_3$, $OCF_3$, CN or halo;
- $R_{11}$ is H or $OCH_3$;
- $R_{42}$ and $R_{48}$ together with the atoms to which they are bound form a 10 membered heteroaryl; and
- $R_{31}$ is selected from the group consisting of —$CR_{51}$=$CH_2$, —CH=$CHCH_2N(CH_3)_2$ and —CH=$CHCH_3$, wherein $R_{51}$ is H or F.

2. A formulation comprising the compound of claim 1 and a pharmaceutically-acceptable adjuvant, diluent or carrier.

3. The formulation of claim 2 provided in a nanoparticle for targeted delivery.

4. A method for treating an HPV infection, the method comprising the step of administering a formulation according to claim 2 to a subject in need of treating the HPV infection.

5. The method of claim 4, wherein said formulation is administered orally, transdermally, topically, subcutaneously, intramuscularly, or intravenously.

6. The method of claim 4, wherein the formulation is formulated for topical application to the cervix, anus, or pharynx.

7. The method of claim 5, wherein said formulation is administered transdermally.

8. The method of claim 4, wherein said formulation is a time-release formulation.

9. The formulation of claim 2, wherein the formulation further comprises a compound selected from the group consisting of fatty acids, glucose, amino acids, cholesterol, lipids, glycosides, alkaloids, and natural phenols.

10. The compound of claim 1 having the structure of

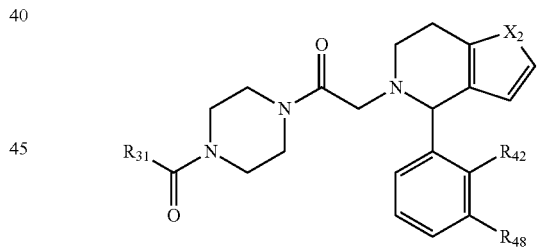

wherein
- $R_{31}$ is —CH=$CH_2$,
- $X_2$ is S; and
- $R_{42}$ and $R_{48}$ together with the atoms to which they are bound form a 10 membered heteroaryl.

* * * * *